US012564643B2

(12) United States Patent
Satchi-Fainaro et al.

(10) Patent No.: US 12,564,643 B2
(45) Date of Patent: Mar. 3, 2026

(54) POLYMERIC NANOVACCINES AND USES THEREOF

(71) Applicant: Ramot at Tel-Aviv University Ltd., Tel-Aviv (IL)

(72) Inventors: Ronit Satchi-Fainaro, Tel-Aviv (IL); Helena Florindo, Tel-Aviv (IL); Joao Conniot, Tel-Aviv (IL); Anna Scomparin, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1119 days.

(21) Appl. No.: 17/418,977

(22) PCT Filed: Dec. 27, 2019

(86) PCT No.: PCT/IL2019/051420
§ 371 (c)(1),
(2) Date: Jun. 28, 2021

(87) PCT Pub. No.: WO2020/136657
PCT Pub. Date: Jul. 2, 2020

(65) Prior Publication Data
US 2022/0111029 A1     Apr. 14, 2022

Related U.S. Application Data

(60) Provisional application No. 62/869,591, filed on Jul. 2, 2019, provisional application No. 62/785,715, filed on Dec. 28, 2018.

(51) Int. Cl.
*A61K 45/00* (2006.01)
*A61K 31/7105* (2006.01)
(Continued)

(52) U.S. Cl.
CPC ...... *A61K 47/6937* (2017.08); *A61K 31/7105* (2013.01); *A61K 31/711* (2013.01);
(Continued)

(58) Field of Classification Search
None
See application file for complete search history.

(56) References Cited

U.S. PATENT DOCUMENTS

| | | | |
|---|---|---|---|
| 7,517,520 | B2 | 4/2009 | Manolova et al. |
| 8,518,410 | B2 | 8/2013 | Zurawski et al. |

(Continued)

FOREIGN PATENT DOCUMENTS

| | | |
|---|---|---|
| WO | WO 2008/149230 | 12/2008 |
| WO | WO 2010/042555 | 4/2010 |

(Continued)

OTHER PUBLICATIONS

Vyas, "The dendritic cell: The general of the army," Virulence 3:7: 601-602 (Year: 2012).*

(Continued)

*Primary Examiner* — M Franco G Salvoza

(57) ABSTRACT

A polymeric nanoparticle is disclosed which comprises:
(i) at least one disease-associated antigen which is capable of producing a T-cell response, wherein the disease-associated antigen is encapsulated in the nanoparticle;
(ii) at least one adjuvant; and
(iii) a dendritic cell targeting moiety which is attached to the outer surface of the nanoparticle.
Use of the nanoparticle for treating diseases associated with abnormal cell growth or an infection is also disclosed.

3 Claims, 48 Drawing Sheets

Specification includes a Sequence Listing.

Schematic representation of man-NP

(51) Int. Cl.

| | |
|---|---|
| *A61K 31/711* | (2006.01) |
| *A61K 39/00* | (2006.01) |
| *A61K 39/39* | (2006.01) |
| *A61K 39/395* | (2006.01) |
| *A61K 45/06* | (2006.01) |
| *A61K 47/69* | (2017.01) |
| *A61P 35/00* | (2006.01) |

(52) U.S. Cl.
CPC .. *A61K 39/0011* (2013.01); *A61K 39/001151* (2018.08); *A61K 39/001182* (2018.08); *A61K 39/001191* (2018.08); *A61K 39/001192* (2018.08); *A61K 39/39* (2013.01); *A61K 39/3955* (2013.01); *A61K 45/06* (2013.01); *A61P 35/00* (2018.01); *A61K 2039/505* (2013.01); *A61K 2039/55511* (2013.01); *A61K 2039/55516* (2013.01); *A61K 2039/55561* (2013.01); *A61K 2039/55572* (2013.01); *A61K 2039/55583* (2013.01); *A61K 2039/6093* (2013.01)

(56) References Cited

U.S. PATENT DOCUMENTS

| | | | |
|---|---|---|---|
| 9,539,217 B2 * | 1/2017 | Sosin | ............... A61K 39/025 |
| 2010/0278919 A1 | 11/2010 | Denes et al. | |
| 2016/0051698 A1 | 2/2016 | Schneck et al. | |
| 2018/0200196 A1 | 7/2018 | Fahmy et al. | |

FOREIGN PATENT DOCUMENTS

| | | |
|---|---|---|
| WO | WO 2016/154544 | 9/2016 |
| WO | WO 2018/039332 | 3/2018 |
| WO | WO 2020/136657 | 7/2020 |
| WO | WO 2020/136657 A9 | 8/2020 |

OTHER PUBLICATIONS

Huang et al., "Processing and Presentation of Exogenous HLA Class I Peptides by Dendritic Cells from Human Immunodeficiency Virus Type 1-Infected Persons," Journal of Virology, vol. 79, No. 5: 3052-3062 (Year: 2005).*

Hamdy et al., "Activation of Antigen-Specific T Cell-Responses by Mannan-Decorated PLGA Nanoparticles," Pharm Res 28:2288-2301 (Year: 2011).*

Esmaeili et al., "Preparation of PLGA nanoparticles using TPGS in the spontaneous emulsification solvent diffusion method," Journal of Experimental Nanoscience, 2:3, 183-192 (Year: 2007).*

International Search Report and the Written Opinion Dated Feb. 24, 2020 From the International Searching Authority Re. Application No. PCT/IL2019/051420.

Gutjahr et al. "Biodegradable Polymeric Nanoparticles-Based Vaccine Adjuvants for Lymph Nodes Targeting", Vaccines, 4(4): 34-1-34-16, Published Online Oct. 12, 2016.

Keselowsky et al. "Multifunctional Dendritic Cell-Targeting Polymeric Microparticles. Engineering New Vaccines for Type 1 Diabetes", Human Vaccines, 7(1): 37-44, Published Online Jan. 1, 2011.

Silva et al. "Nanoparticle Impact on Innate Immune Cell Pattern-Recognition Receptors and Inflammasomes Activation", Seminars in Immunology, 34: 3-24, Available Online Sep. 21, 2017.

Supplementary European Search Report and the European Search Opinion Dated Jan. 2, 2023 From the European Patent Office Re. Application No. 19901899.5. (9 Pages).

Xu et al. "Nanoparticle-Delivered Transforming Growth Factor-β siRNA Enhances Vaccination against Advanced Melanoma by Modifying Tumor Microenvironment", ACS Nano 2014, 8(4): 3636-3645, Mar. 10, 2014.

* cited by examiner

Schematic representation of man-NP

Melan A/MART-1 peptide

MPLA (immune potentiator)

D-α-tochoperyl PEG1000 succinate (immune potentiator)

CpG (immune potentiator)

Mannose

PLGA/PLA matrix

FIG. 1B　TEM　　　　FIG. 1C　SEM 500 nm

2 µm

FIG. 1D
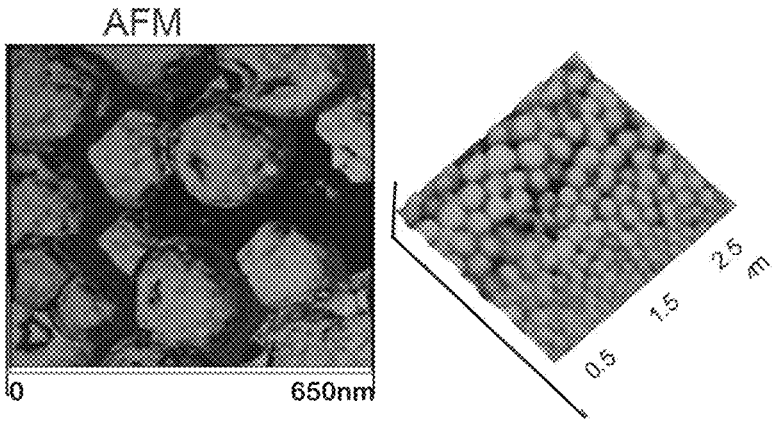
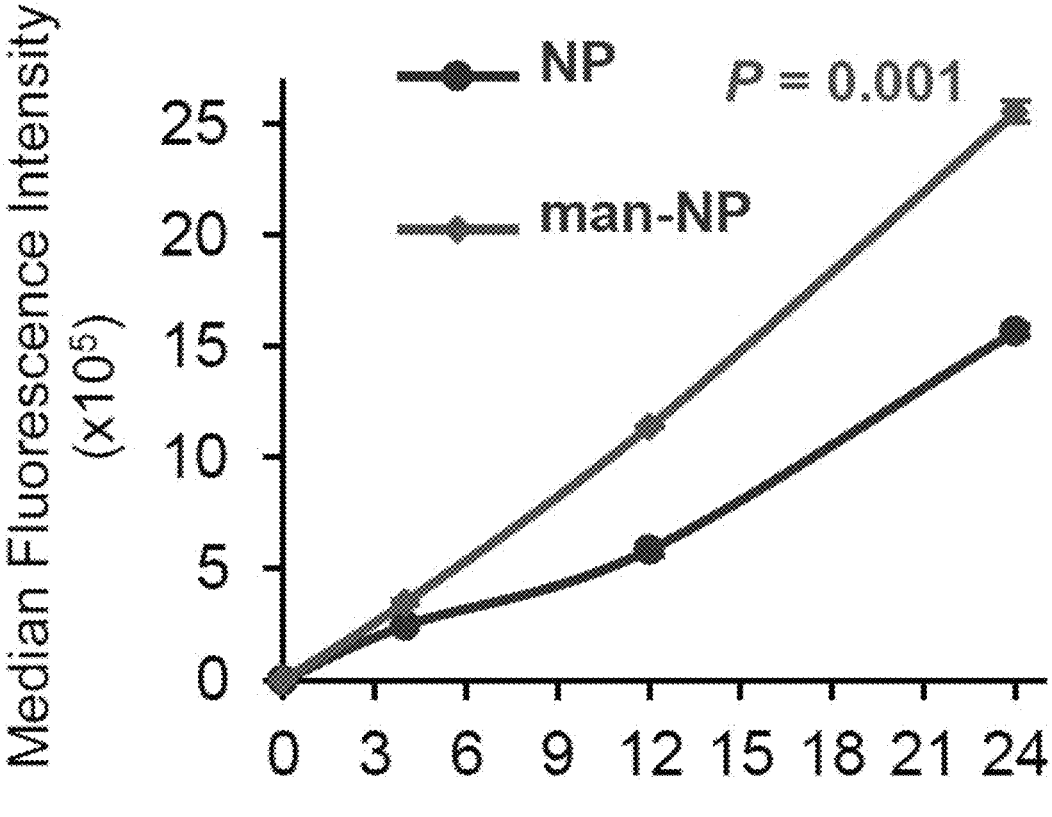
FIG. 1E

NP man-NP

WGA - Wheat germ agglutinin (membrane)
Rhodamine-labeled particles
DAPI (nucleus)
Scale bar - 50 μm

NP man-NP

FIG. 2C

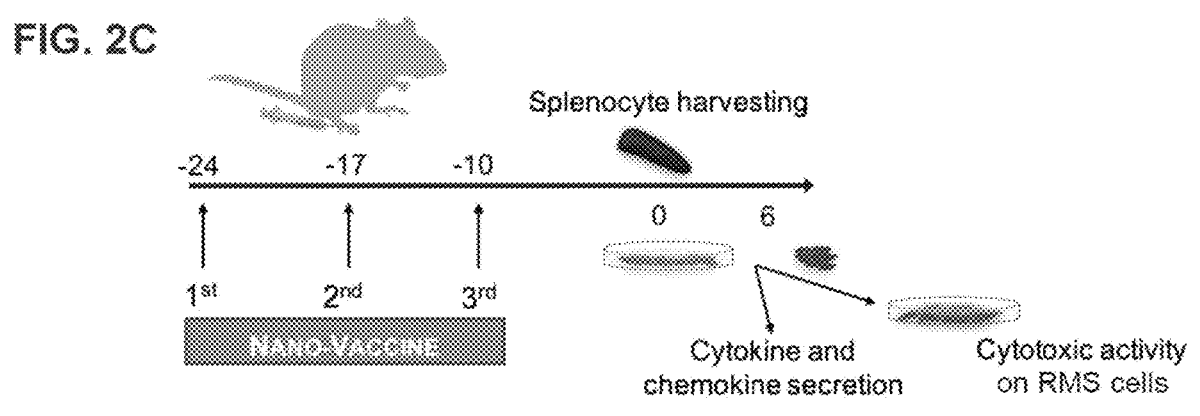

Splenocyte harvesting

-24　　　-17　　　-10　　　　　0　　　6

1st　　　2nd　　　3rd

NANOVACCINE

Cytokine and
chemokine secretion

Cytotoxic activity
on RMS cells

····x···· Untreated

——➤—— NP (empty)

——————— MHCl-ag/MHCll-ag (free)

——◆—— NP MHCl-ag/NP MHCll-ag

————— man-NP MHCl-ag/man-NP MHCll-ag

— ➤ — PBS

— ▢ — MHCl-ag (free)

— ◆ — NP MHCl-ag

— ◆ — man-NP MHCl-ag

FIG. 2F
NP MHCI-ag/NP MHCII-ag
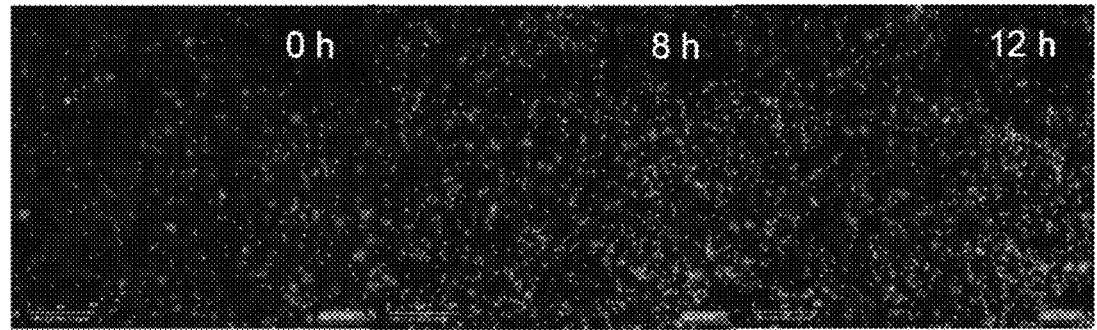
man-NP MHCI-ag/man-NP MHCII-ag
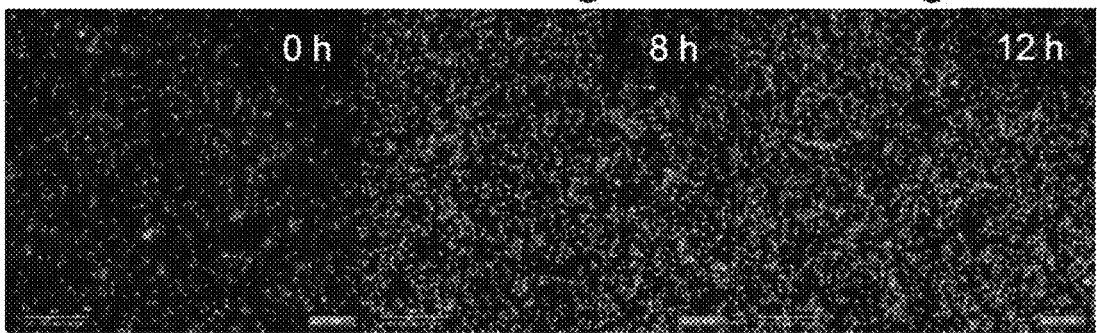
Scale bar – 300 µm
RMS cells    caspase 3/7

PBS

MHCI-ag/MHCII-ag/CpG/MPLA (free)

NP MHCI-ag/NP MHCII-ag man-NP MHCI-ag/man-NP MHCII-ag

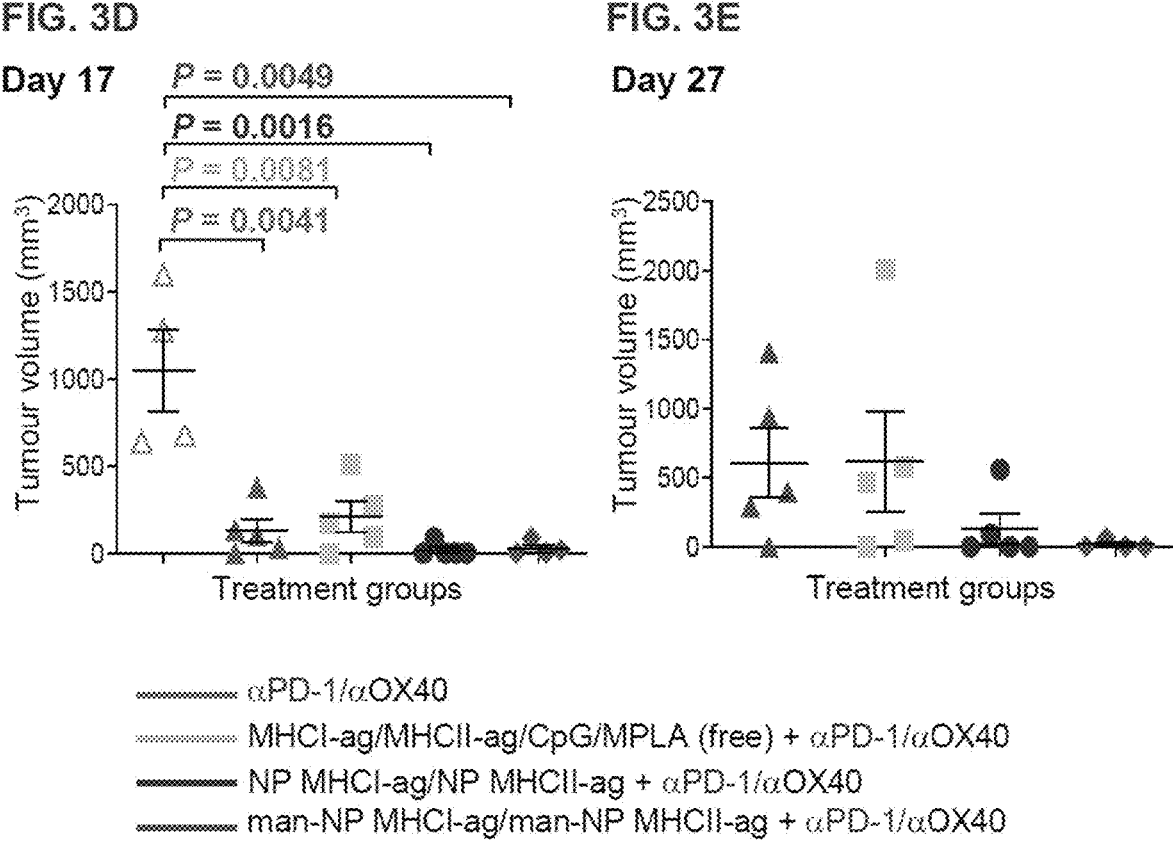
FIG. 3D
FIG. 3E
αPD-1/αOX40
MHCl-ag/MHCII-ag/CpG/MPLA (free) + αPD-1/αOX40
NP MHCl-ag/NP MHCII-ag + αPD-1/αOX40
man-NP MHCl-ag/man-NP MHCII-ag + αPD-1/αOX40
FIG. 4A
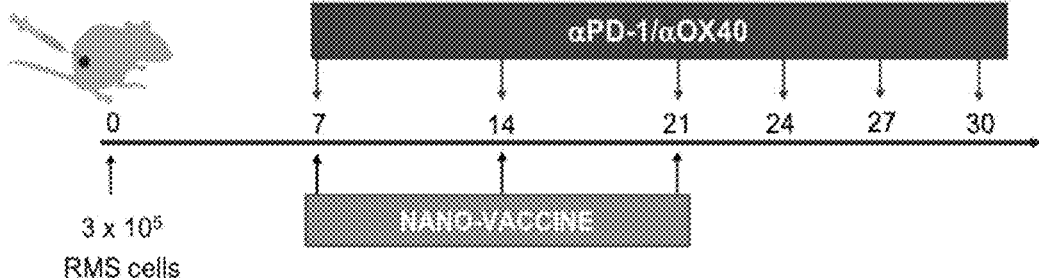

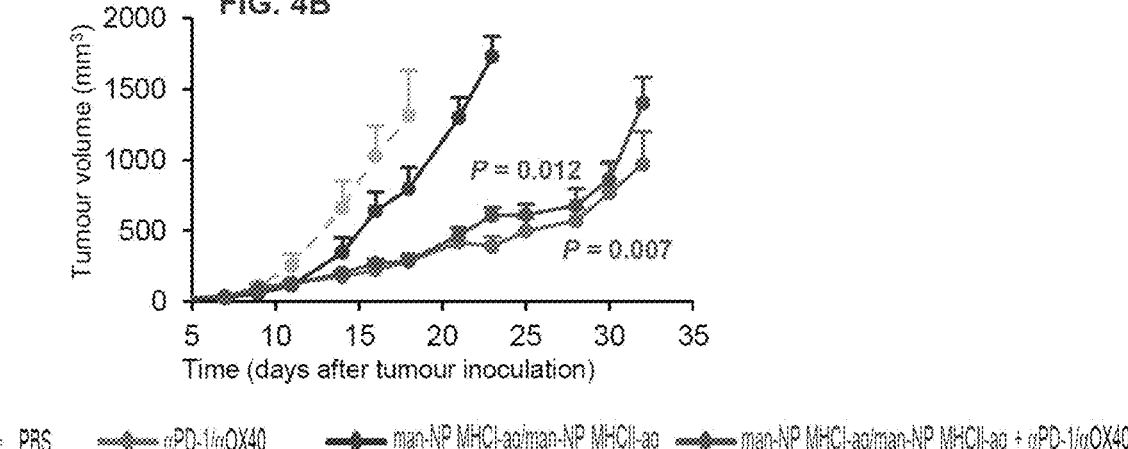
FIG. 4B
- ◁ - PBS    —◆— αPD-1/αOX40    —◆— man-NP MHCI-ag/man-NP MHCII-ag    —◆— man-NP MHCI-ag/man-NP MHCII-ag + αPD-1/αOX40
FIG. 4C
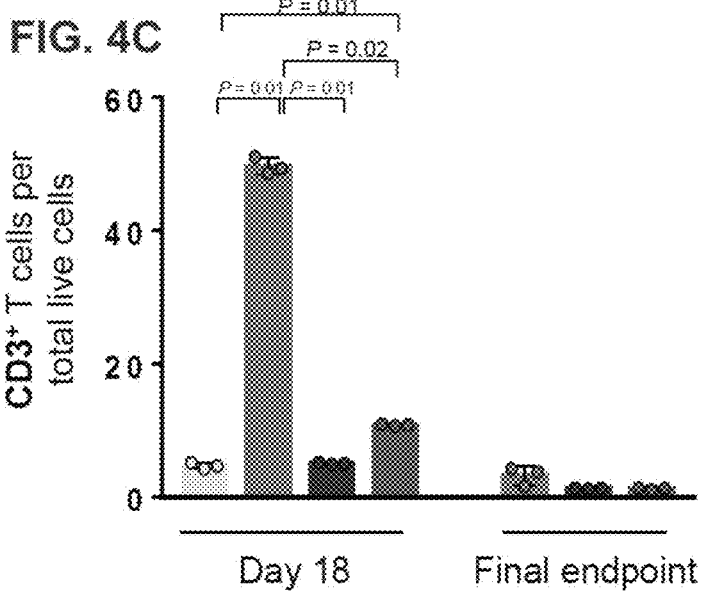

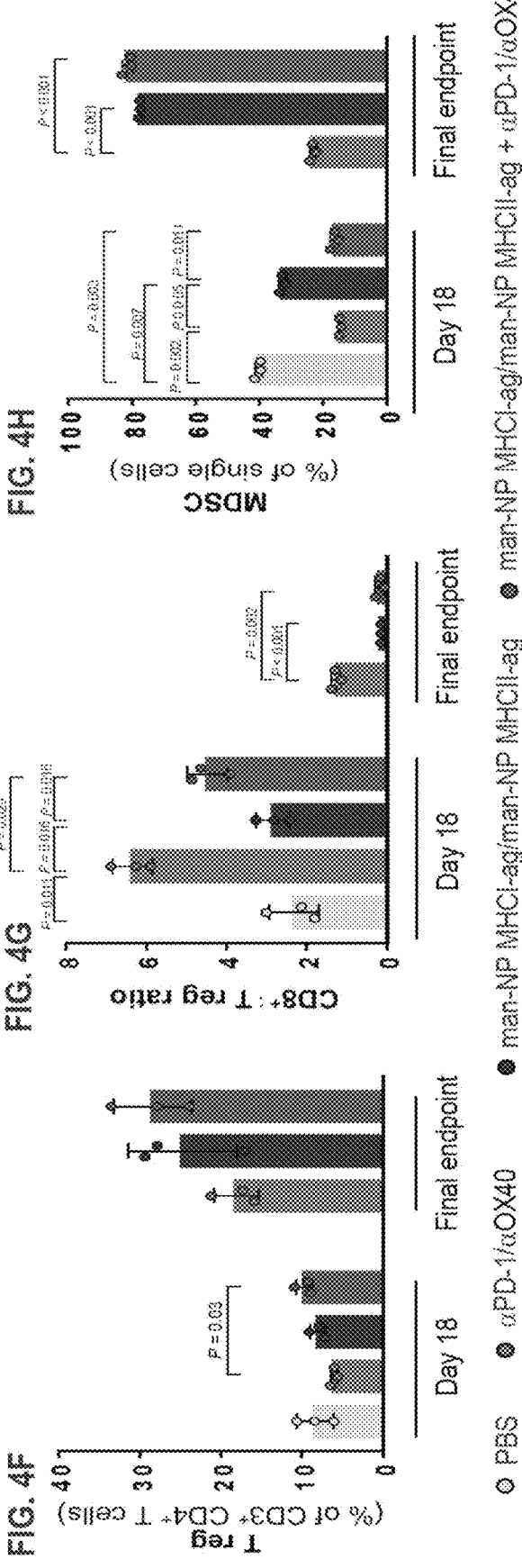

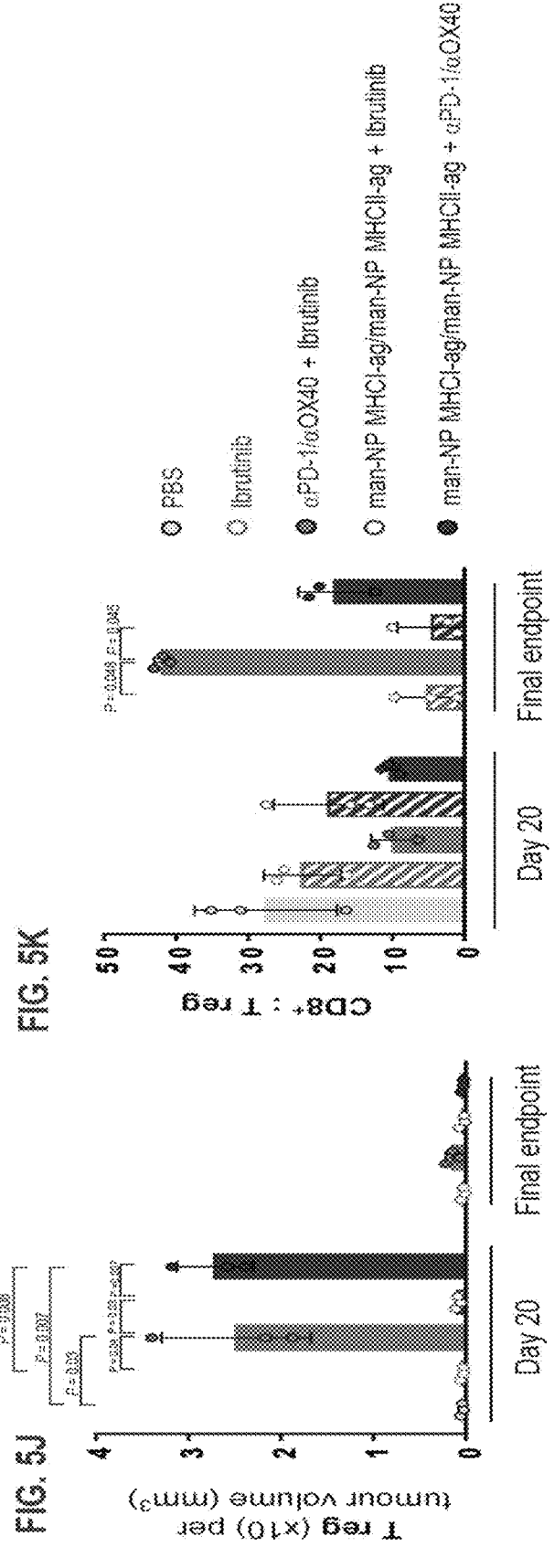

FIG. 7A
FIG. 7B
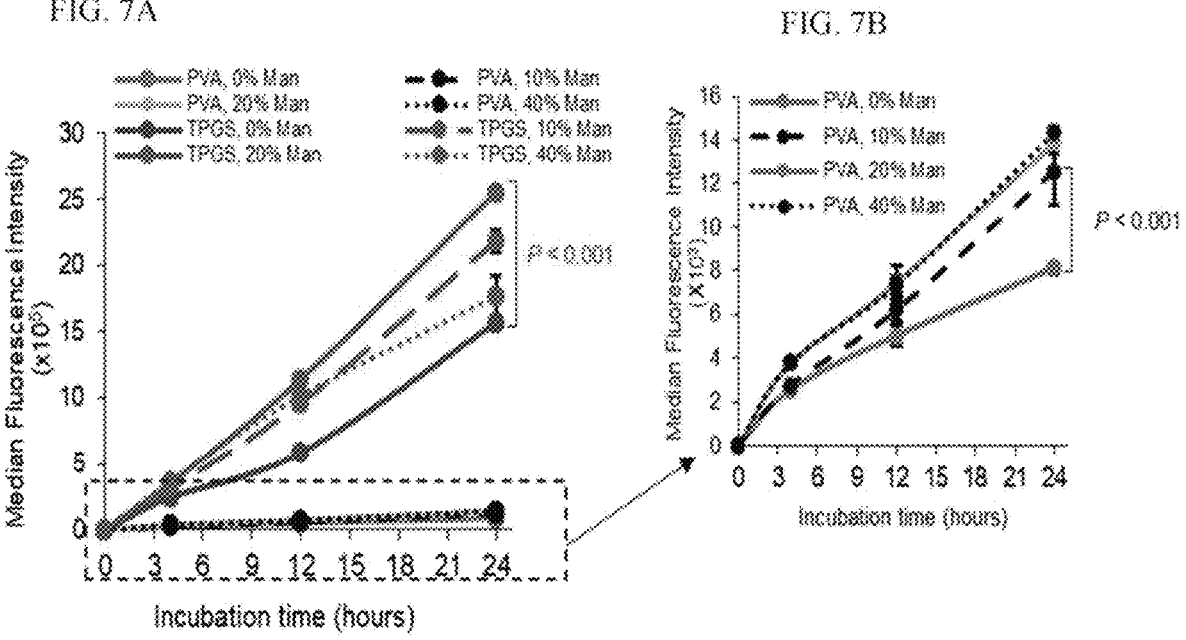
FIG. 7C
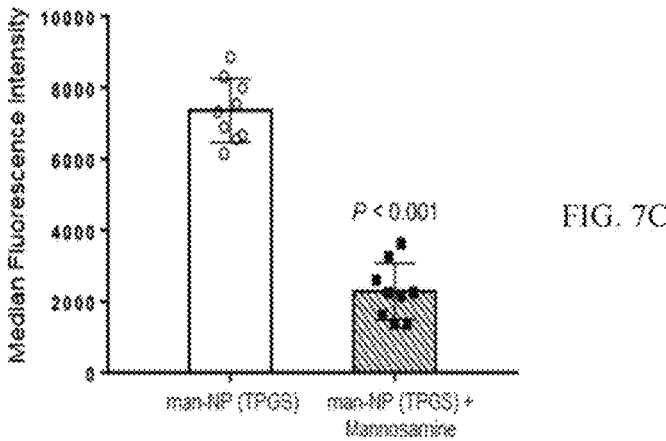

FIG. 8D
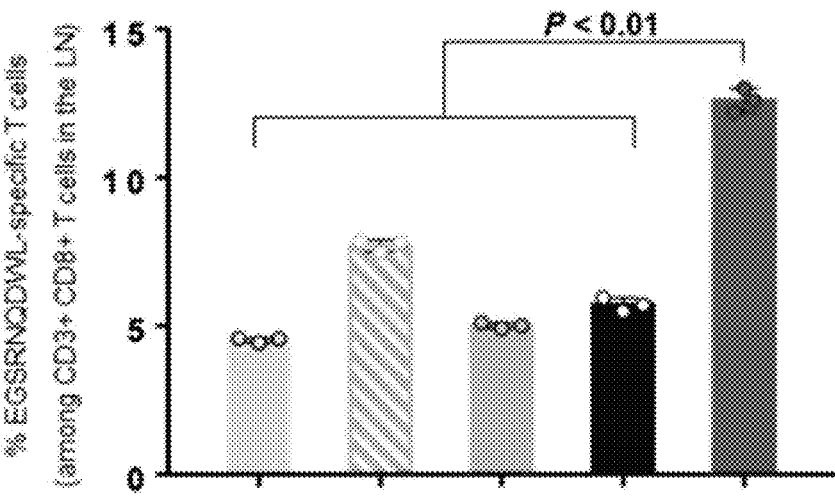
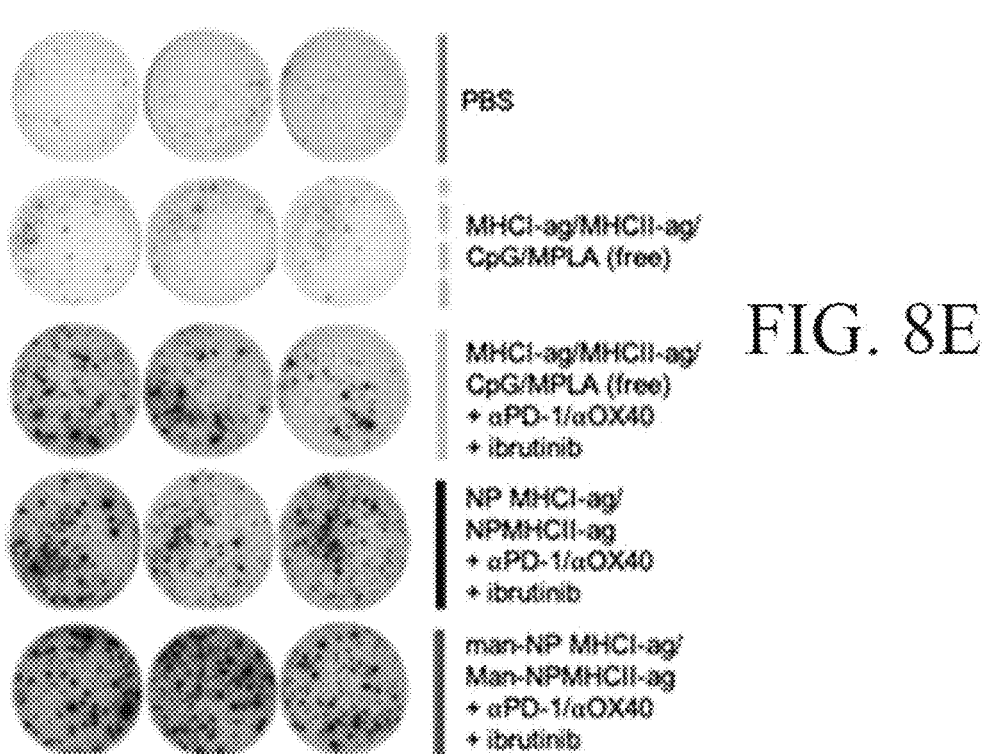
FIG. 8E

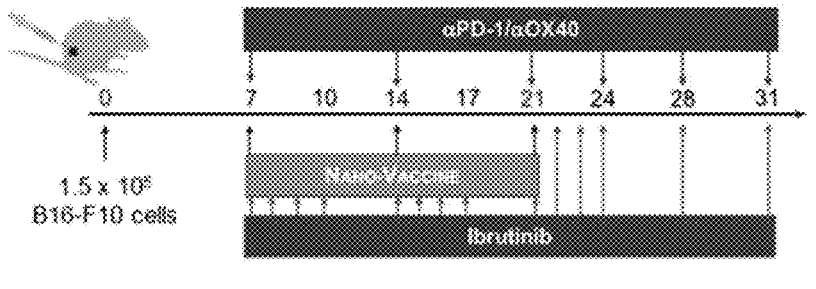
FIG. 9A
1.5 x 10⁵
B16-F10 cells
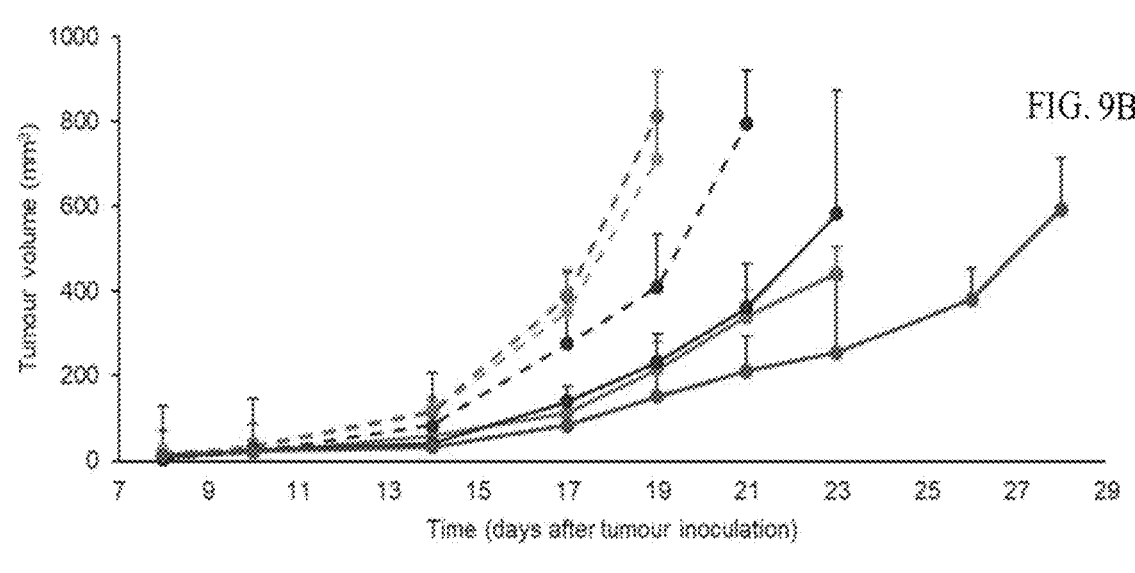
FIG. 9B

○ PBS

● αPD-1/ αOX40 + Ibrutinib

● NP MHCI-ag/NP MHCII-ag + αPD-1/αOX40

● man-NP MHCI-ag/man-NP MHCII-ag + αPD-1/αOX40 + Ibrutinib

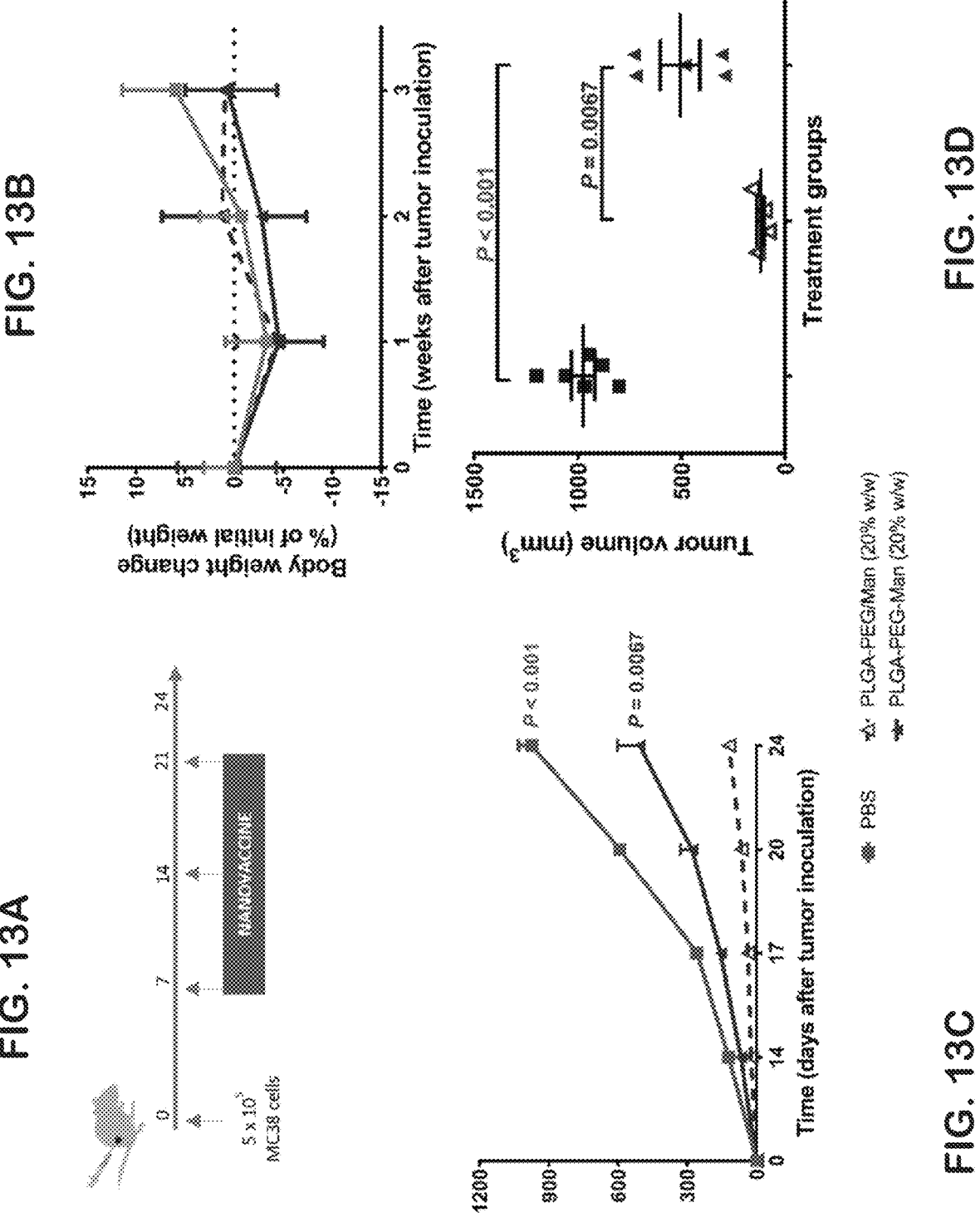

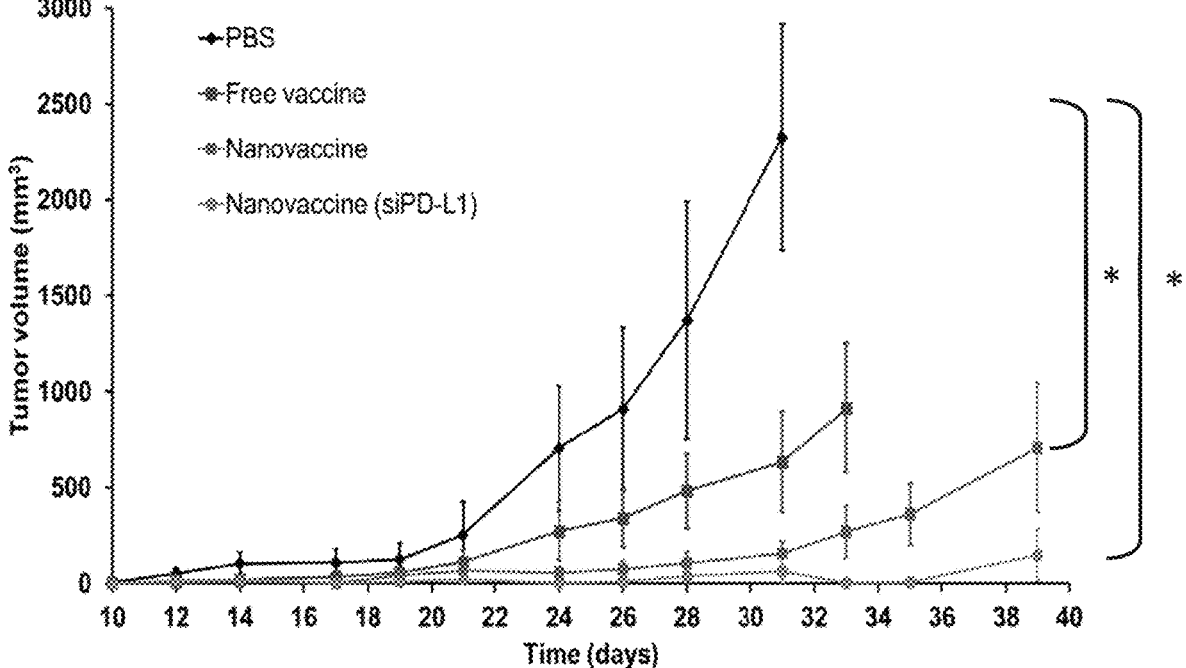
FIG. 14`

FIG. 15

━━━ PBS    ┉┉┉ 4.5 mg/kg mart-1 vaccine    ━━━ 3 mg/kg bindarit
┉┉┉ 3 mg/kg bindarit + 4.5 mg/kg mart-1 vaccine

SEQUENCE LISTING

<160> NUMBER OF SEQ ID NOS: 28

<210> SEQ ID NO 1
<211> LENGTH: 10
<212> TYPE: PRT
<213> ORGANISM: Artificial sequence

```
<220> FEATURE:
<223> OTHER INFORMATION: disease-associated antigen amino acid sequence

<400> SEQUENCE: 1

Glu Leu Ala Gly Ile Gly Ile Leu Thr Val
1               5                   10

<210> SEQ ID NO 2
<211> LENGTH: 23
<212> TYPE: PRT
<213> ORGANISM: Artificial sequence
<220> FEATURE:
<223> OTHER INFORMATION: disease-associated antigen amino acid sequence

<400> SEQUENCE: 2

Arg Asn Gly Tyr Arg Ala Leu Met Asp Lys Ser Leu His Val Gly Thr
1               5                   10                  15

Gln Cys Ala Leu Thr Arg Arg
            20

<210> SEQ ID NO 3
<211> LENGTH: 20
<212> TYPE: DNA
<213> ORGANISM: Artificial Sequence
<220> FEATURE:
<223> OTHER INFORMATION: Examples of CpG oligodeoxynucleotide nucleic
      acid sequence

<400> SEQUENCE: 3
tccatgacgt tcctgacgtt                                                   20

<210> SEQ ID NO 4
<211> LENGTH: 10
<212> TYPE: PRT
<213> ORGANISM: Artificial sequence
<220> FEATURE:
<223> OTHER INFORMATION: disease-associated antigen amino acid sequence

<400> SEQUENCE: 4

Val Val Arg His Cys Pro His His Glu Arg
1               5                   10

<210> SEQ ID NO 5
<211> LENGTH: 10
<212> TYPE: PRT
<213> ORGANISM: Artificial sequence
<220> FEATURE:
<223> OTHER INFORMATION: disease-associated antigen amino acid sequence

<400> SEQUENCE: 5

Glu Val Val Arg His Cys Pro His His Glu
1               5                   10

<210> SEQ ID NO 6
<211> LENGTH: 9
<212> TYPE: PRT
<213> ORGANISM: Artificial sequence
<220> FEATURE:
<223> OTHER INFORMATION: disease-associated antigen amino acid sequence

<400> SEQUENCE: 6

Ala Ala Leu Leu Asn Lys Leu Tyr Ala
1               5

<210> SEQ ID NO 7
<211> LENGTH: 9
```

```
<212> TYPE: PRT
<213> ORGANISM: Artificial sequence
<220> FEATURE:
<223> OTHER INFORMATION: disease-associated antigen amino acid sequence

<400> SEQUENCE: 7

Glu Gly Ser Arg Asn Gln Asp Trp Leu
1               5

<210> SEQ ID NO 8
<211> LENGTH: 16
<212> TYPE: PRT
<213> ORGANISM: Artificial sequence
<220> FEATURE:
<223> OTHER INFORMATION: disease-associated antigen amino acid sequence

<400> SEQUENCE: 8

Trp Asn Arg Gln Leu Tyr Pro Glu Trp Thr Glu Ala Gln Arg Leu Asp
1               5                   10                  15

<210> SEQ ID NO 9
<211> LENGTH: 27
<212> TYPE: PRT
<213> ORGANISM: Artificial sequence
<220> FEATURE:
<223> OTHER INFORMATION: disease-associated antigen amino acid sequence

<400> SEQUENCE: 9

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 10
<211> LENGTH: 27
<212> TYPE: PRT
<213> ORGANISM: Artificial sequence
<220> FEATURE:
<223> OTHER INFORMATION: disease-associated antigen amino acid sequence

<400> SEQUENCE: 10

Glu Phe Lys His Ile Lys Ala Phe Asp Arg Thr Phe Ala Asn Asn Pro
1               5                   10                  15

Gly Pro Met Val Val Phe Ala Thr Pro Gly Met
            20                  25

<210> SEQ ID NO 11
<211> LENGTH: 8
<212> TYPE: PRT
<213> ORGANISM: Artificial sequence
<220> FEATURE:
<223> OTHER INFORMATION: disease-associated antigen amino acid sequence

<400> SEQUENCE: 11

Ser Ile Ile Asn Phe Glu Lys Leu
1               5

<210> SEQ ID NO 12
<211> LENGTH: 17
<212> TYPE: PRT
<213> ORGANISM: Artificial sequence
<220> FEATURE:
<223> OTHER INFORMATION: disease-associated antigen amino acid sequence

<400> SEQUENCE: 12

Ile Ser Gln Ala Val His Ala Ala His Ala Glu Ile Asn Glu Ala Gly
```

-continued

```
1               5               10              15

Arg

<210> SEQ ID NO 13
<211> LENGTH: 15
<212> TYPE: PRT
<213> ORGANISM: Artificial sequence
<220> FEATURE:
<223> OTHER INFORMATION: disease-associated antigen amino acid sequence

<400> SEQUENCE: 13

Gly Asp Phe Gly Leu Ala Thr Glu Lys Ser Arg Trp Ser Gly Ser
1               5               10              15

<210> SEQ ID NO 14
<211> LENGTH: 9
<212> TYPE: PRT
<213> ORGANISM: Artificial sequence
<220> FEATURE:
<223> OTHER INFORMATION: disease-associated antigen amino acid sequence

<400> SEQUENCE: 14

Tyr Leu Ser Gly Ala Asp Leu Asn Leu
1               5

<210> SEQ ID NO 15
<211> LENGTH: 9
<212> TYPE: PRT
<213> ORGANISM: Artificial sequence
<220> FEATURE:
<223> OTHER INFORMATION: disease-associated antigen amino acid sequence

<400> SEQUENCE: 15

Ala Ser Met Thr Asn Met Glu Leu Met
1               5

<210> SEQ ID NO 16
<211> LENGTH: 28
<212> TYPE: PRT
<213> ORGANISM: Artificial sequence
<220> FEATURE:
<223> OTHER INFORMATION: disease-associated antigen amino acid sequence

<400> SEQUENCE: 16

Gly Ile Pro Val His Leu Glu Leu Ala Ser Met Thr Asn Met Glu Leu
1               5               10              15

Met Ser Ser Ile Val His Gln Gln Val Phe Pro Thr
            20              25

<210> SEQ ID NO 17
<211> LENGTH: 17
<212> TYPE: PRT
<213> ORGANISM: Artificial sequence
<220> FEATURE:
<223> OTHER INFORMATION: disease-associated antigen amino acid sequence

<400> SEQUENCE: 17

Lys Leu Val Val Val Gly Ala Gly Gly Val Gly Lys Ser Ala Leu Thr
1               5               10              15

Ile

<210> SEQ ID NO 18
<211> LENGTH: 17
<212> TYPE: PRT
<213> ORGANISM: Artificial sequence
```

```
<220> FEATURE:
<223> OTHER INFORMATION: disease-associated antigen amino acid sequence

<400> SEQUENCE: 18

Lys Leu Val Val Val Gly Ala Asp Gly Val Gly Lys Ser Ala Leu Thr
1               5                   10                  15

Ile

<210> SEQ ID NO 19
<211> LENGTH: 15
<212> TYPE: PRT
<213> ORGANISM: Artificial sequence
<220> FEATURE:
<223> OTHER INFORMATION: disease-associated antigen amino acid sequence

<400> SEQUENCE: 19

Ser Ala Leu Thr Ile Gln Leu Ile Gln Asn His Phe Val Asp Glu
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: disease-associated antigen amino acid sequence

<400> SEQUENCE: 20

Phe Leu Cys Val Phe Ala Ile Asn Asn Thr Lys Ser Phe Glu Asp
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: disease-associated antigen amino acid sequence

<400> SEQUENCE: 21

Phe Tyr Thr Leu Val Arg Glu Ile Arg Lys His Lys Glu Lys Met
1               5                   10                  15

<210> SEQ ID NO 22
<211> LENGTH: 9
<212> TYPE: PRT
<213> ORGANISM: Artificial sequence
<220> FEATURE:
<223> OTHER INFORMATION: disease-associated antigen amino acid sequence

<400> SEQUENCE: 22

Tyr Ile His Thr His Thr Phe Tyr Val
1               5

<210> SEQ ID NO 23
<211> LENGTH: 9
<212> TYPE: PRT
<213> ORGANISM: Artificial sequence
<220> FEATURE:
<223> OTHER INFORMATION: disease-associated antigen amino acid sequence

<400> SEQUENCE: 23

Ser Gln Ile Trp Asn Leu Asn Pro Val
1               5

<210> SEQ ID NO 24
<211> LENGTH: 9
<212> TYPE: PRT
```

-continued

```
<213> ORGANISM: Artificial sequence
<220> FEATURE:
<223> OTHER INFORMATION: disease-associated antigen amino acid sequence

<400> SEQUENCE: 24

Gln Ala Thr Glu Ala Glu Arg Ser Phe
1               5

<210> SEQ ID NO 25
<211> LENGTH: 13
<212> TYPE: PRT
<213> ORGANISM: Artificial sequence
<220> FEATURE:
<223> OTHER INFORMATION: disease-associated antigen amino acid sequence

<400> SEQUENCE: 25

Ala Lys Phe Val Ala Ala Trp Thr Leu Lys Ala Ala Ala
1               5                   10

<210> SEQ ID NO 26
<211> LENGTH: 21
<212> TYPE: DNA
<213> ORGANISM: Artificial sequence
<220> FEATURE:
<223> OTHER INFORMATION: siRNA nucleic acid sequence

<400> SEQUENCE: 26
gggcuaccau gccaacuuct t                                              21

<210> SEQ ID NO 27
<211> LENGTH: 21
<212> TYPE: DNA
<213> ORGANISM: Artificial sequence
<220> FEATURE:
<223> OTHER INFORMATION: siRNA nucleic acid sequence

<400> SEQUENCE: 27
cccacauaaa aaacaguugt t                                              21

<210> SEQ ID NO 28
<211> LENGTH: 21
<212> TYPE: DNA
<213> ORGANISM: Artificial sequence
<220> FEATURE:
<223> OTHER INFORMATION: siRNA nucleic acid sequence

<400> SEQUENCE: 28
gaagcccaau caauaacugt t                                              21
```

POLYMERIC NANOVACCINES AND USES THEREOF

RELATED APPLICATIONS

This application is a National Phase of PCT Patent Application No. PCT/IL2019/051420 having International filing date of Dec. 27, 2019, which claims the benefit of priority under 35 USC § 119 (e)_of U.S. Provisional Patent Application Nos. 62/785,715 filed on Dec. 28, 2018, and 62/869,591 filed on Jul. 2, 2019, the. The contents of the above applications are all incorporated by reference as if fully set forth herein in their entirety.

SEQUENCE LISTING STATEMENT

The ASCII file, entitled 87839 Sequence Listing.txt, created on Jun. 28, 2021, comprising 7,590 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to polymeric nano-vaccines and, more particularly, but not exclusively, to their use in treating or preventing diseases associated with abnormal cell growth, such as cancer, or an infectious disease.

The basis of acquired, specific immunity in an organism is the ability to discriminate between self and non-self antigenic substances. The mammalian immune system uses cell surface molecules known as the major histocompatibility complex (MHC) to discriminate between self- and non-self antigens. In the case of bacterial infections or other insults from external sources, new proteins or compounds enter the organism. Some cells involved in the immune response are capable of phagocytosing foreign organisms or proteins. These immune cells degrade the protein products and the derived peptides are expressed at the cell surface in association with MHC molecules, where a specific adaptive immune response is generated against novel non-self components. This activity is called antigen processing and presentation and cells that mediate this activity are called antigen presenting cells (APCs).

In addition to recognizing insults from external sources, the immune system is also designed to detect internal insults, e.g., cancer. Cancer cells express aberrant molecules known as tumor-associated antigens (TAAs). The immune system has the potential to recognize such structures as "foreign" and to mount specific immune responses against them, so as to reject tumor cells in much the same way as bacterial cells. Although a large number of human TAAs have been characterized, most of these antigens are also expressed by some normal cells. As a result, immunological tolerance to such molecules develops, making it difficult to stimulate responses against tumor-associated antigens.

APCs, such as dendritic cells (DCs) and macrophages, play important roles in the activation of innate and adaptive immunity as well as in the maintenance of immunological tolerance. Major efforts have been made to develop vaccines, in particular tumor vaccines, in an attempt to promote DC maturation and co-stimulation as a means of enhancing immunity. DC maturation serves as the critical switch from the maintenance of self-tolerance to the induction of immunity. Mature DCs stimulate cytotoxic T-lymphocyte (CTL) responses against cells expressing the antigen.

DCs are professional antigen-presenting cells having a key regulatory role in the maintenance of tolerance to self-antigens and in the activation of innate and adaptive immunity. When DCs encounter pro-inflammatory stimuli such as microbial products, the maturation process of the cell is initiated by up-regulating cell surface-expressed antigenic peptide-loaded MHC molecules and co-stimulatory molecules. Following maturation and homing to local lymph nodes, DCs establish contact with T cells by forming an immunological synapse, where the T cell receptor (TCR) and co-stimulatory molecules congregate in a central area surrounded by adhesion molecules. Once activated, CD8+ T cells can autonomously proliferate for several generations and acquire cytotoxic function without further antigenic stimulation. It has therefore been proposed that the level and duration of peptide-MHC complexes (signal 1) and co-stimulatory molecules (signal 2) provided by DCs are essential factors in determining the magnitude and fate of an antigen-specific T cell response. Thus, DCs play a significant role in mediating immune responses.

Background art include US Patent Application No. 20100278919, US Patent Application No. 20180200196, US Patent Application No. 20160051698, US Patent Application No. 20170042994, International Patent Application WO 2018/039332, Gutjahr et al., Vaccines 2016, 4, 34; doi: 10.3390 and Keselowsky et al., Human Vaccines 7:1, pages 37-44; January 2011.

SUMMARY OF THE INVENTION

According to an aspect of some embodiments of the present invention there is provided a polymeric nanoparticle comprising:
- (i) at least one disease-associated antigen which is capable of producing a T-cell response,
- (ii) at least one adjuvant;
- (iii) a dendritic cell targeting moiety which is attached to the outer surface of the nanoparticle; and
- (iv) a polynucleotide agent capable of downregulating an amount of a polypeptide in the dendritic cell, wherein the polynucleotide agent is encapsulated in the nanoparticle.

According to an aspect of some embodiments of the present invention there is provided a polymeric nanoparticle comprising:
- (i) at least one disease-associated antigen which is capable of producing a T-cell response, wherein the disease-associated antigen is encapsulated in the nanoparticle;
- (ii) at least one adjuvant;
- (iii) a dendritic cell targeting moiety which is attached to the outer surface of the nanoparticle; and
- (iv) d-α-tocopheryl polyethylene glycol 1000 succinate (TPGS).

According to an aspect of some embodiments of the present invention there is provided a polymeric nanoparticle comprising:
- (i) at least one disease-associated antigen which is capable of producing a T-cell response, wherein the disease-associated antigen is encapsulated in the nanoparticle;
- (ii) at least one toll-like receptor ligand which is encapsulated in the nanoparticle; and
- (iii) a dendritic cell targeting moiety which is attached to the outer surface of the nanoparticle.

According to an aspect of some embodiments of the present invention there is provided a vaccine comprising the polymeric nanoparticle described herein.

According to an aspect of some embodiments of the present invention there is provided a method of treating a disease-associated with abnormal cell growth or an infectious disease, in a subject in need thereof comprising administering to the subject a therapeutically effective amount of the polymeric nanoparticles described herein, thereby treating the disease-associated with abnormal cell growth or an infectious disease.

According to an aspect of some embodiments of the present invention there is provided an article of manufacture comprising the polymeric nanoparticle described herein and at least one immune checkpoint protein modulator.

According to some embodiments of the invention, the polymeric nanoparticle is generated by entrapping the at least one disease-associated antigen and the at least one adjuvant in the nanoparticle.

According to some embodiments of the invention, the polymeric nanoparticle is preferentially endocytosed by dendritic cells as compared to macrophages.

According to some embodiments of the invention, the disease-associated antigen is a neoantigen.

According to some embodiments of the invention, the disease-associated antigen is derived from a protein selected from the group consisting of MART-1/Melan-A, glycoprotein 100 (gp100), tyrosinase, tyrosinase-related protein 1 (TRP1), tyrosinase-related protein 2 (TRP2), BRCA, α-Lactalbumin, HER2/neu, BRAF-V600E, GL261, MUT30, CEA, MUC1, MUC13, CEA, CA 19-9, KRAS, NRAS, RAS, MUC4, prostate cancer antigen (PCA), TRAMP, RANKL, Sperm Protein 17 (SP17), A-kinase anchor protein 4 (AKAP4), Pituitary Tumor Transforming Gene 1 (PTTG1), Aurora kinase A, ovalbumin, bovine serum albumin (BSA), p53, a cancer testis antigen and Adenomatous polyposis coli (APC).

According to some embodiments of the invention, the polymeric nanoparticle has a diameter no greater than 250 nm.

According to some embodiments of the invention, the polymeric nanoparticle has a diameter of about 170 nm.

According to some embodiments of the invention, the polymeric nanoparticle is fabricated from at least one polymer selected from the group consisting of poly(lactic-co-glycolic acid) (PLGA), Polyethylene glycol-PLGA (PEG-PLGA), Poly(lactic acid) (PLA), PEG-PLA, Polycaprolactone (PCL) and PEG-PCL.

According to some embodiments of the invention, the polymeric nanoparticle is fabricated from PLGA and PLA.

According to some embodiments of the invention, the polymeric nanoparticle further comprises PVA.

According to some embodiments of the invention, a ratio of PLGA:PLA is 1:4.

According to some embodiments of the invention, the at least one adjuvant comprises a Toll-like receptor (TLR) ligand.

According to some embodiments of the invention, the Toll-like receptor (TLR) ligand is selected from the group consisting of a ligand of TLR2, a ligand of TLR3, a ligand of TLR4, a ligand of TLR5, a ligand of TLR7/8 and a ligand of TLR9.

According to some embodiments of the invention, the ligand is selected from the group consisting of zymosan, Polyinosinic-polycytidylic acid (Poly(I:C)), Monophosphoryl Lipid A (MPLA)), flagellin, Gardiquimod, Imiquimod (R837) Resiquimod, Inducible T-cell co-stimulator ligand (ICOSL) and CpG oligodeoxynucleotides (CpG ODN).

According to some embodiments of the invention, the at least one adjuvant is selected from the group consisting of hyaluronic acid (HA), poloxamer 407, 2',3'-cGAMP, chitosan, Dectin-1 agonist laminarin and β-glucan.

Additional adjuvants are contemplated that stimulate the innate immune system aiming at dendritic cell maturation and subsequent stimulation of the adaptive immune response including immunomodulatory molecules such as cytokines, chemokines or immunostimulatory molecules, such as toll-like receptor agonists or interferon regulatory factors (such as STING and cGAMP).

According to some embodiments of the invention, the polymeric nanoparticle further comprises a surfactant.

According to some embodiments of the invention, the surfactant is selected from the group consisting of d-α-tocopheryl polyethylene glycol 1000 succinate (TPGS) and poly(vinyl alcohol) (PVA).

According to some embodiments of the invention, the at least one peptide is at least two peptides, wherein the first of the at least two peptides is an MHC class I peptide and the second of the at least two peptide is an MHC class II peptide.

According to some embodiments of the invention, the polymeric nanoparticle further comprises a polynucleotide agent capable of downregulating an amount of a polypeptide in the dendritic cell.

According to some embodiments of the invention, the polynucleotide agent is selected from the group consisting of an antisense polynucleotide, siRNA, gRNA, miRNA, a DNAzyme and a Ribozyme.

According to some embodiments of the invention, the polypeptide is selected from the group consisting of TGF-β, VEGFA, PD-L1/PD-1, VEGFR1, VEGFR2, VEGFR3, IDO, RANKL, IL-10 and PGE2 receptor.

According to some embodiments of the invention, the polynucleotide agent is siRNA.

According to some embodiments of the invention, the siRNA is complexed with a polymer.

According to some embodiments of the invention, the polymer is selected from the group consisting of glutamate chitosan, poly-arginine, alkylated poly(a)glutamate amine (APA) and poly-(a)glutamic acid (PGA).

According to some embodiments of the invention, the dendritic cell targeting moiety is selected from the group consisting of mannose, tri-mannose, PEG-mannose, laminarin and PEG-laminarin.

According to some embodiments of the invention, the at least one disease-associated antigen which is capable of producing a T-cell response is derived from MART-1/Melan-A.

According to some embodiments of the invention, the at least one disease-associated antigen is set forth in SEQ ID NO: 1 and SEQ ID NO: 2.

According to some embodiments of the invention, the polymeric nanoparticle is for use in treating a disease-associated with abnormal cell growth or an infection.

According to some embodiments of the invention, the disease-associated with abnormal cell growth is cancer.

According to some embodiments of the invention, the cancer is selected from the group consisting of melanoma, glioblastoma, breast cancer, pancreatic cancer, prostate cancer, lung cancer, colorectal cancer.

According to some embodiments of the invention, the cancer is melanoma or breast cancer.

According to some embodiments of the invention, the disease-associated with abnormal cell growth is Familial adenomatous polyposis (PAP).

According to some embodiments of the invention, the administering is subcutaneous, intradermal, intramuscular, intratumoral, intravenous or nasal.

According to some embodiments of the invention, the method further comprises administering to the subject a therapeutically effective amount of at least one immune checkpoint protein modulator.

According to some embodiments of the invention, the method further comprises administering to the subject a therapeutically effective amount of at least one stimulatory immune checkpoint protein modulator.

According to some embodiments of the invention, the method further comprises administering to the subject a therapeutically effective amount of at least one inhibitory immune checkpoint protein modulator.

According to some embodiments of the invention, the stimulatory immune checkpoint protein is selected from the group consisting of OX40, CD27, CD40, GITR, CD137, CD28, HVEM and ICOS.

According to some embodiments of the invention, the inhibitory immune checkpoint protein is selected from the group consisting of PD-1, adenosine $A_{2A}$ receptor, B7-H3, B7-H4, BTLA, CTLA-4, IDO, KIR, LAG-3, PD-L1, TIM-3 and VISTA (C10orf54).

According to some embodiments of the invention, the modulator is an inhibitory antibody directed against the immune checkpoint protein.

According to some embodiments of the invention, the at least one immune checkpoint protein modulator is anti-PD1 antibody and anti-OX40 antibody.

According to some embodiments of the invention, the method further comprises administering to the subject a therapeutically effective amount of an inhibitor of myeloid derived suppressor cells.

According to some embodiments of the invention, the inhibitor comprises a Brutons tyrosine kinase (Btk) inhibitor.

According to some embodiments of the invention, the Brutons tyrosine kinase (Btk) inhibitor is selected from the group consisting of ibrutinib, acalabrutinib, Spebrutinib.

According to some embodiments of the invention, the immune checkpoint protein is selected from the group consisting of OX40, CD27, CD40, GITR, CD137, CD28, HVEM, ICOS, PD-1, adenosine $A_{2A}$ receptor, B7-H3, B7-H4, BTLA, CTLA-4, IDO, KIR, LAG-3, PD-L1, TIM-3 and VISTA (C10orf54).

According to some embodiments of the invention, the article of manufacture further comprises an inhibitor of myeloid derived suppressor cells.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-H. NP and Man-NP are potential delivery systems for vaccination. A, Schematic representation of mannose-PLGA/PLA nanoparticles (man-NP). B, TEM image of spherical man-NP. C, SEM image of spherical man-NP. D, AFM images of spherical man-NP, showing narrow size polydispersity. E, Particle internalisation by DC determined by FACS. Non-treated cells and non-labelled NP were used as negative controls. Data are presented as mean±SD, N=4 independent samples with 3 technical replicates, F, Confocal images of DC after 3 hours of incubation with NP (left) and man-NP (right). Z-stacks (top) and projections (bottom). (N=3; n=6). Scale bars=50 G, Percentage of NP internalisation 17 hours after immunisation with empty NP or antigen-loaded NP. man-NP (TPGS) were preferentially internalised by circulating DC in immunised C57BL/6J mice and increased the expression of the activation and maturation markers of these APC. h, Median florescence intensity (MFI) of activated DC that internalised NP, present in the lymph nodes (LN), 17 hours after immunisation. Mean±SD; N=3, n=3, where N denotes the number of independent experiments and n denotes the number of measurements per experiment. Statistics: Two-way ANOVA followed by Tukey Post-Hoc test (G) or Bonferroni test (H).

FIGS. 2A-F. NP and man-NP vaccines induce splenocyte activation and ex vivo cytotoxicity against melanoma cells. A, Non-invasive intravital fluorescence imaging of C57BL/6J mouse 3 hours and 48 hours following hock immunisation with NP (left) and man-NP (right). B, Organ biodistribution according to fluorescence signal (N=3 animals) with NP and man-NP. Data represent mean±SD. C, Immunisation scheme of C57BL/6J mice and ex vivo splenocyte cytotoxic activity timeline. D, Secretion of IFN-$\gamma$, GM-CSF, TNF-$\alpha$, IL-2, IL-6, CCL1/TCA-3, MIP-1$\beta$, MCP-5/CCL12 and TARC/CCL17 upon re-stimulation of splenocytes in culture. The highest levels of IFN-$\gamma$ and GM-CSF were induced by man-NP. Elevated levels of CCL1/TCA-3 and TARC/CCL17, which are chemokines associated with activated T cells, also suggested that our particles played a major role in priming antigen-specific $CD8^+$ T cells. An inclusive assessment of the triad, IFN-$\gamma$, IL-2 and TNF-$\alpha$, predicted an improved cytotoxic $CD8^+$ T cell activity for antigen-loaded man-NP. These nano-vaccines also presented a role in the modulation of Th2 chemokine secretion profile. NP MHCI-ag/NP MHCII-ag and man-NP MHCI-ag/man-NP MHCII-ag decreased MIP-1B/CCL4 secretion, whereas both man-NP MHCI-ag and the combination man-NP MHCI-ag/man-NP MHCII-ag equally reduced the MCP-5/CCL12 levels. E, Cytotoxic activity of splenocytes harvested from immunised C57BL/6J mice, after incubation with Melan-A/MART-1 and CD28 in solution for 6 days. Data are presented as mean±SEM, N=6 biological independent samples. One-way ANOVA with Tukey test. F, Images of RMS cells co-cultured with reactivated splenocytes from the group immunised with NP MHCI-ag and MHCII-ag (top) and the group immunised with man-NP MHCI-ag/man-NP MHCII-ag (bottom). Cell death was detected with an apoptosis reagent that couples to activated caspase-3/7 recognition motif and quantifies apoptosis. The experiment was repeated 5 times with similar results.

FIGS. 3A-E. Prophylactic nano-vaccines have synergistic effect with PD-1 blockade and OX40 activation, restricting melanoma growth and prolonging survival. A, Timeline of immunisation, tumor inoculation and immune checkpoint therapy. B, Tumor growth curve. P values correspond to tumor volume at day 17. Data are presented as mean±SEM (N=4 animals for PBS group and N=5 animals for the remaining groups). One-way ANOVA. C, Kaplan-Meier overall survival over time graph, for mice inoculated with $4.5 \times 10^5$ RMS cells (N=4 animals for PBS group and N=5 animals for the remaining groups). Log-Rank test, P<(105 for the combination man-NP MHCI-ag/man-NP MHCII-ag+ $\alpha$PD-1/$\alpha$OX40 compared to all other treatment groups. D, Individual tumor volume at day 17 (N=4 animals for PBS group and N=5 animals for the remaining groups) with mean±SEM. Unpaired two-tailed t test. E. Day 27 following tumor inoculation (N=5 animals) with mean±SEM.

FIGS. 4A-H. Low CD8±/Treg ratio and high infiltration of Myeloid-derived Suppressor Cells (CD11b$^+$Gr-1$^+$MDSC) compromise the therapeutic efficacy of the combination of mannosylated nano-vaccines with $\alpha$PD-1/$\alpha$OX40. A, Timeline of tumor inoculation and treatments. B, Tumor growth curve. Data are presented as mean±SEM (N=7 animals). P values correspond to tumor volume at day 18 after tumor inoculation. One-way ANOVA. C-H, Tumor-infiltrating immune cell populations. Tumors were isolated on day 18 after tumor cell inoculation and when the tumor volume for final endpoint was reached. Quantification was performed by flow cytometry. Data are presented as mean±SD, N≥3 animals. Unpaired, two-tailed t test.

FIGS. 7A-C. Cy5.5-labeled NP prepared with TPGS (50 $\mu$g/ml) were extensively internalised by murine bone marrow dendritic cells (DC) JAWSII cell line in vitro for 4, 12 and 24 hours. Comparison of the internalisation profile obtained for NP (0%, 10%, 20% and 40%) prepared with Poly(vinyl alcohol) (PVA) (A and B) and NP prepared with TPGS (A), with different percentages of mannose (0, 10, 20 and 40%). C, Competition with soluble mannose in the medium decreased the internalisation of man-NP (TPGS) (500 $\mu$g/ml) by murine bone marrow dendritic cells (DC) JAWSII cell line. Mean±SD; N=9 independent experiments. Unpaired two-tailed t test.

FIGS. 9A-C. Trivalent combination of dendritic cell-targeted nano-vaccines with ibrutinib and $\alpha$PD-1/$\alpha$OX40 restricts melanoma growth on B16-F10 tumor bearing mice. A, Timeline of tumor inoculation and treatments. C, and C, Tumor growth curves. Data are presented as mean±SEM (N=6 animals for PBS group and N=8 animals for the remaining groups for study A (B); N=9 for study B (C).

FIGS. 13A-D. Man-grafted PLGA nano-vaccines co-entrapping Adpgk MC38 short (MHCI) and long (MHCII) neoantigen peptides, the TLR ligands CpG and Poly (I:C) are able to control colorectal cancer growth. A. Timeline of

Figure 1A:
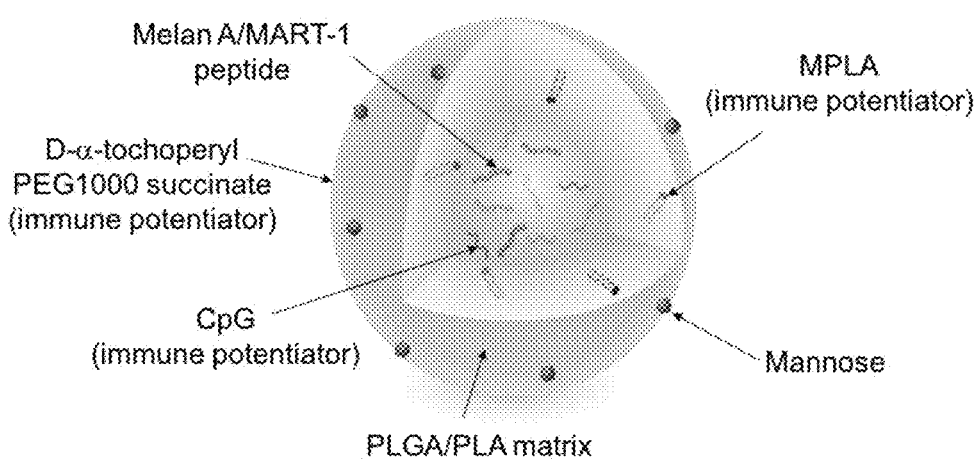

9 tumor inoculation and immunizations. B. Body weight change expressed as percent change from the day of tumor inoculation. C. Tumor growth curve. D. Tumor volume at day 24 following tumor inoculation. Data are presented as mean±SEM (N=3-6). One-way ANOVA followed by Tukey Post-Hoc test. P values regarding to tumor volume at day 24 after tumor inoculation relative to PLGA-PEG-Man (20% w/w) nano-vaccine group.

FIG. 14. Tumor growth curve. The combination of OVA MHC class I or MHC class II antigen peptides, CpG, Poly (I:C) with APA-siPD-L1 within man-PLGA/PLA nano-vaccines has a synergistic effect on inhibiting melanoma growth. Tumor B16-OVA melanoma cells were inoculated at day 0 and animals were vaccinated at days 11, 18 and 25 after tumor inoculation. P values correspond to tumor volume at day 31. *P<0.05 (PBS versus nano-vaccine; PBS versus nano-vaccine (siPD-L1)) Data represent mean±standard error of the mean (SEM), n=6.

Figure 15:
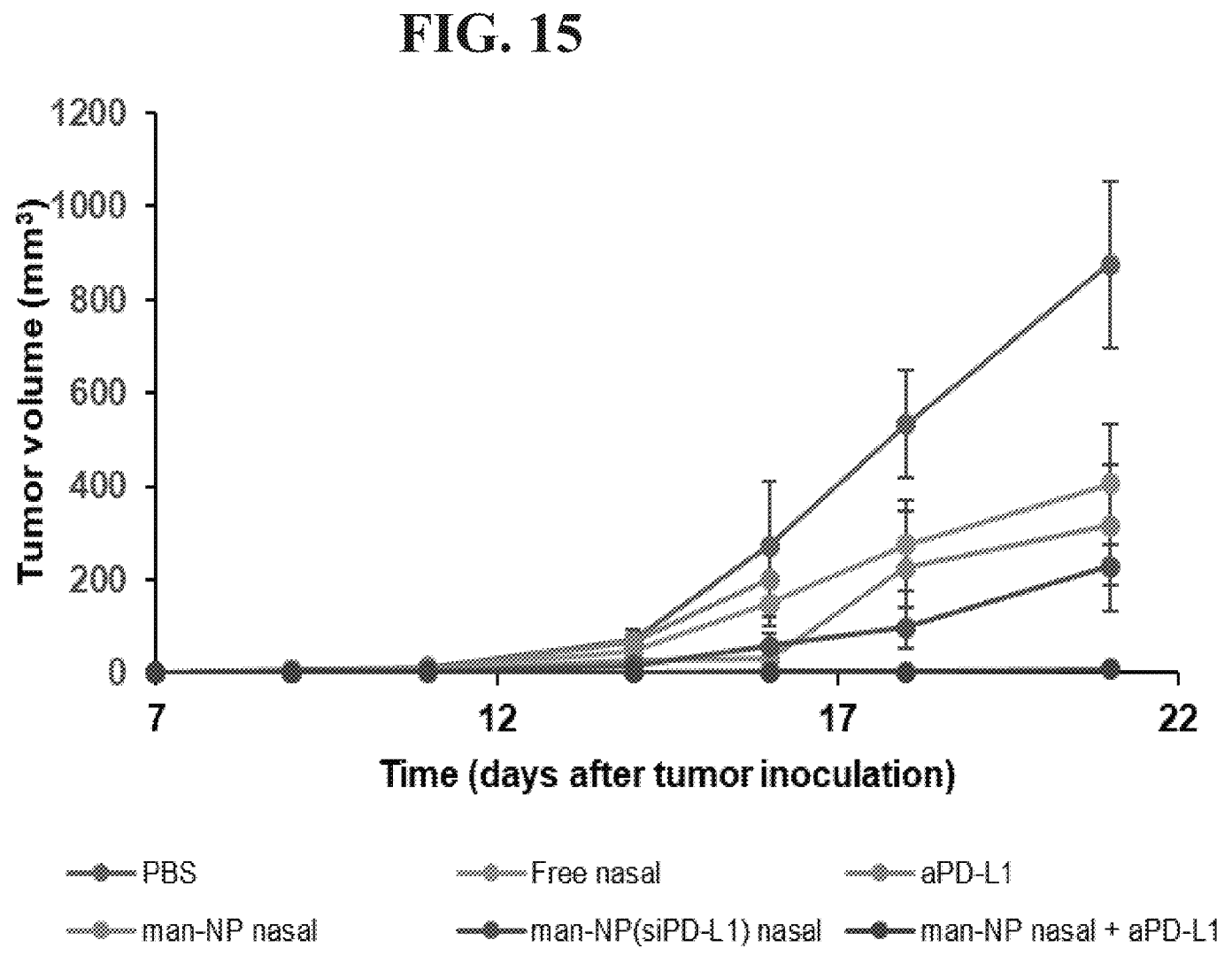

FIG. 15. Tumor growth curve. The combination of MUT30 antigen peptides, CpG, Poly (I:C) with APA-siPD-L1 within man-PLGA/PLA nano-vaccines has a synergistic effect on inhibiting melanoma growth. Tumor B16-F10 melanoma cells were inoculated at day 0 and animals were vaccinated at days 7, 14 and 21 after tumor inoculation. Data are presented as mean±SEM (Data are presented as mean±SD (n=6-7 animals per group).

Figure 16:
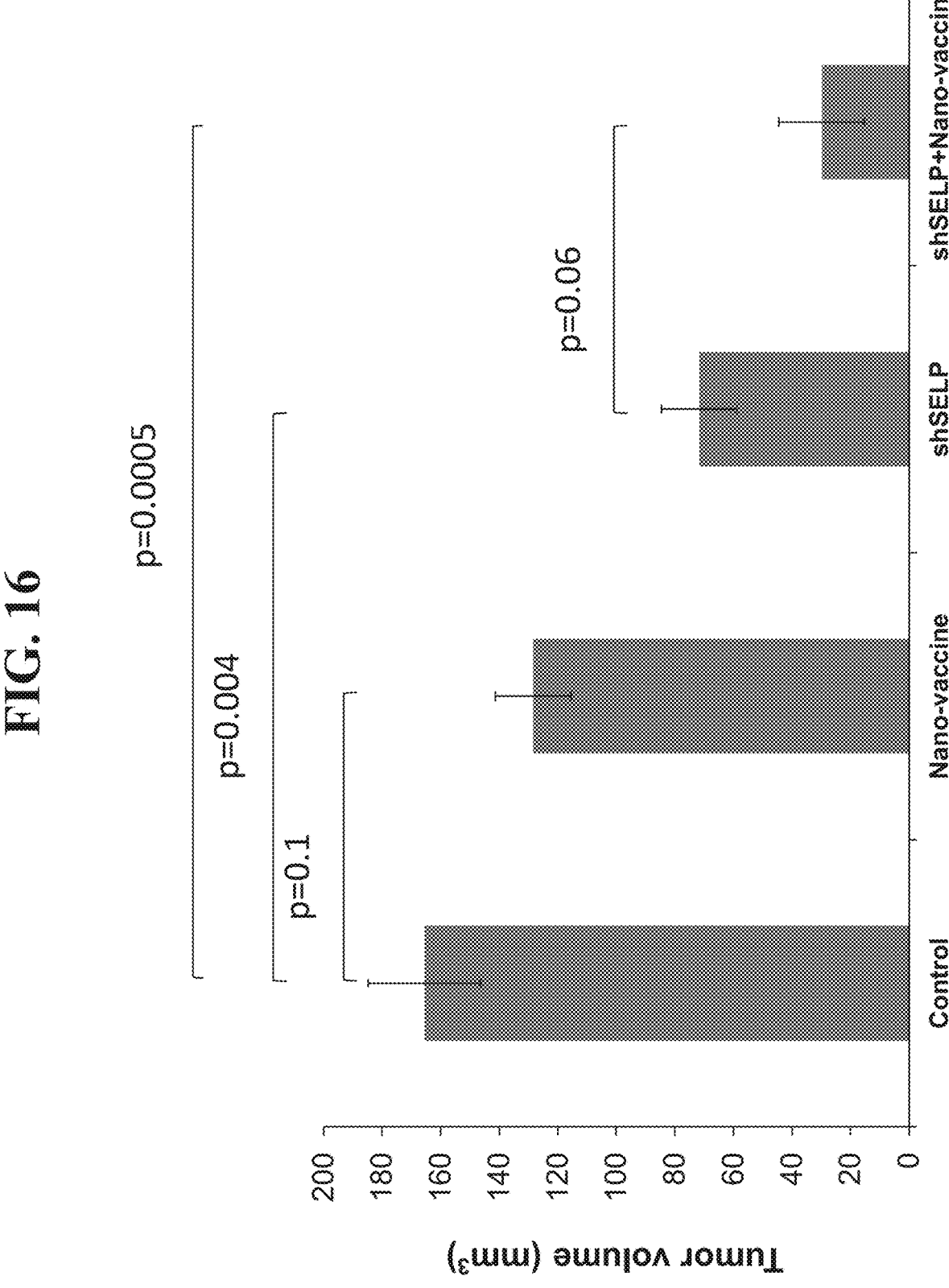

FIG. 16. SELP-knockdown combined with nano-vaccine treatment inhibits tumor growth in murine glioblastoma mouse model. Tumor volume at day 26 post inoculation of untreated or shSELP GL261 tumors in C57/BL6 mice. Mice were untreated or treated with nano-vaccine at days 3, 10 and 17. Tumors detected by MRI (MR solutions, T1 weighted). N=5±SEM.

FIGS. 17A-D. Nano-vaccine combined with MCP-1 inhibitor (bindarit) significantly reduces the tumor size of B 16F10 brain tumor bearing mice at the early stage of tumor establishment followed primary B 16F10 tumor resection. A. Schematic representation of prevention/intervention in vivo study. B. Mice body weight change was followed during the entire experiment and no dramatic events were recorded upon surgery and injection manipulations. N=8±SEM. C. B16F10 brain tumors were monitored by MRI (MR solutions, T1 weighted) at day 7 and 10 upon i. cr. Injection. N=8±SEM. D. MRI quantification of tumor growth at day 7 and 10 post B16F10 intracranial injection.

Figure 18:
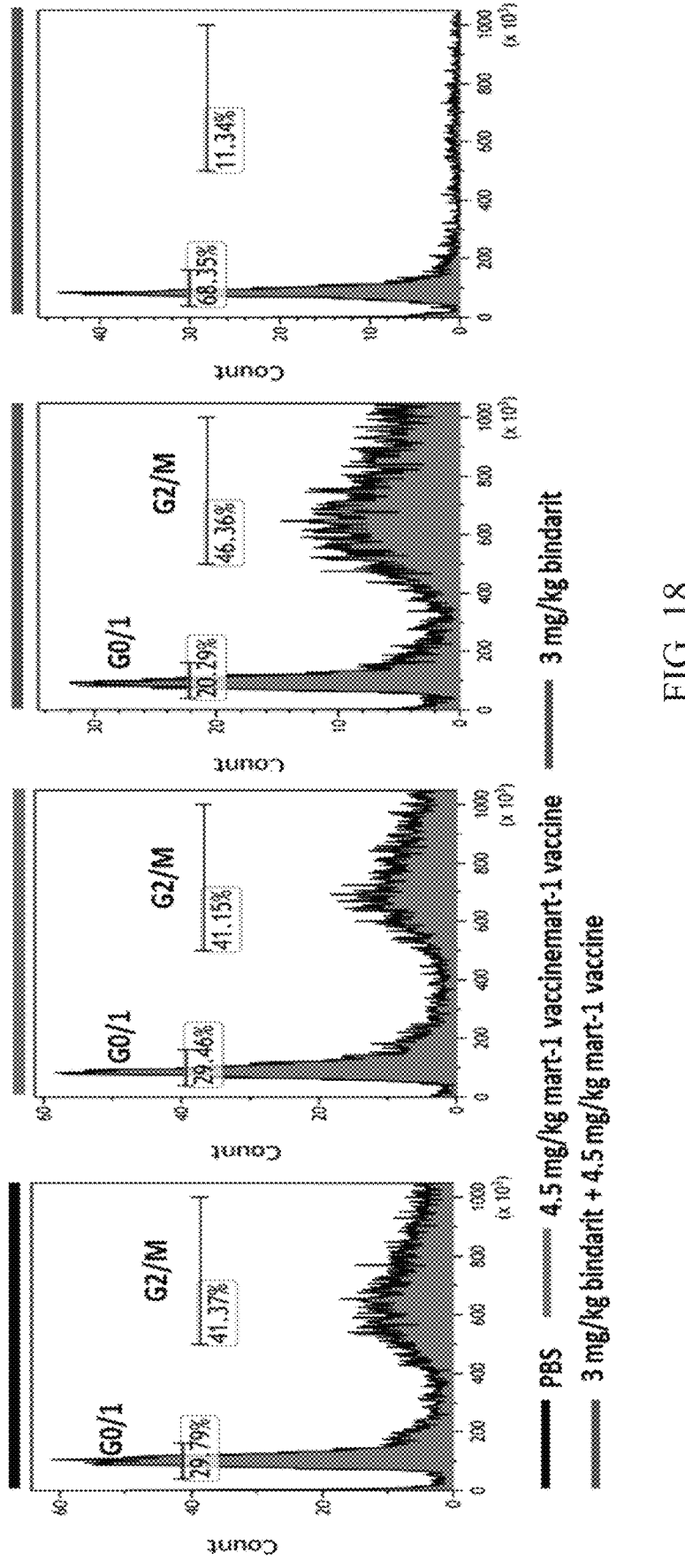

FIG. 18. Nano-vaccine combined with bindarit significantly reduced tumor size of B16-F10 brain tumor bearing mice, by causing cell cycle arrest at G0/1 phase. Cell cycle arrest was assessed following isolation of cells from the brain at day 10.

Figure 19A:
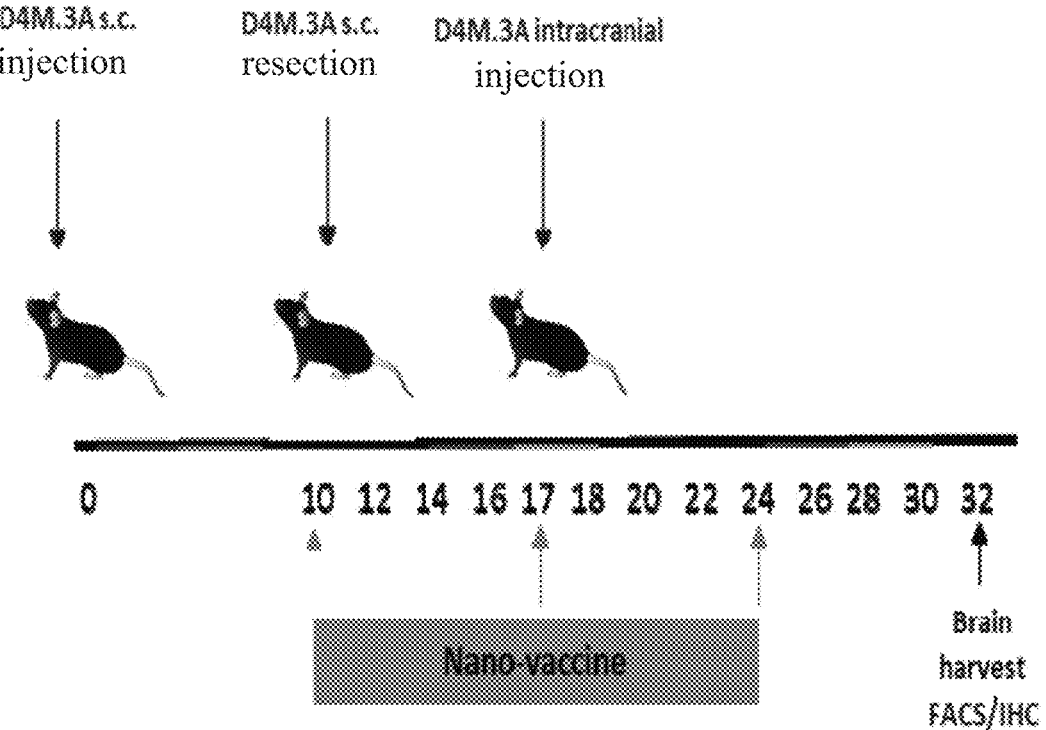
Figure 19B:
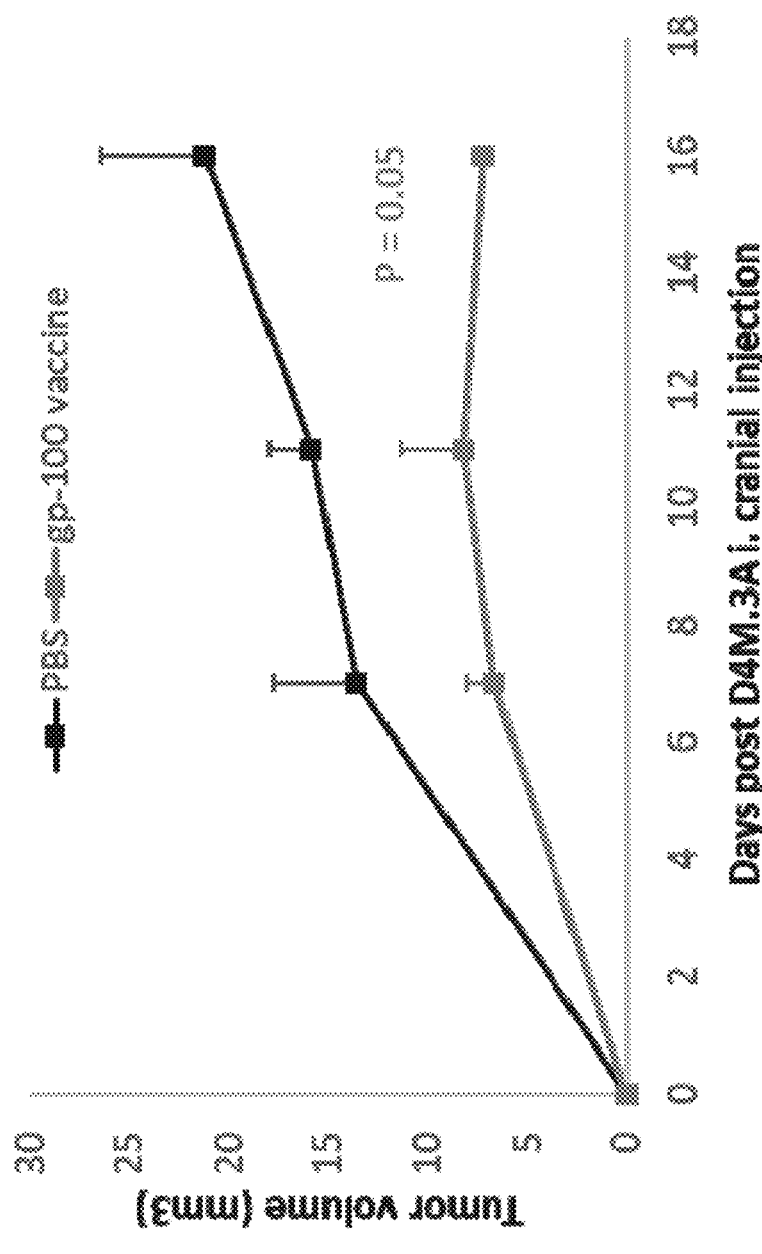

FIGS. 19A-B. Nano-vaccine reduces tumor size of D4M.3A tumor bearing mice at the early stage of tumor establishment followed primary D4M.3A tumor resection. A. Schematic representation of prevention/intervention in vivo study. B. D4M.3A brain tumors were monitored by MRI (MR solutions, T1 weighted) at day 8, 11 and 16 upon i. cr. Injection (N=3). MRI quantification of tumor size at day 8, 11 and 16 post D4M.3A intracranial injection is shown.

DESCRIPTION OF SPECIFIC EMBODIMENTS OF THE INVENTION

The present invention, in some embodiments thereof, relates to polymeric nano-vaccines and, more particularly, but not exclusively, to their use in treating or preventing diseases associated with abnormal cell growth, such as cancer, and infectious diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Vaccines have successfully eradicated a large number of diseases. However, for some diseases (such as cancer) there is no suitable vaccine. One way to overcome this issue is the development of new adjuvant formulations, which are able to induce the appropriate immune response without sacrificing safety. Lymph nodes are the site of lymphocyte priming by antigen-presenting cells and subsequent adaptive immune response, and are a promising target for vaccine formulations.

The present inventors proposed that co-delivery of disease-associated antigens and adjuvants by the same nanoparticle enhances antigen internalization, processing, and subsequent presentation. This is a key step to overcome host tolerance to tumor cells by improving effective T-cell priming and lymphocyte expansion. In order to enhance the uptake of the particles into dendritic cells (DCs), the present inventors propose decorating the outer surface of the nanoparticle with a dendritic cell targeting moiety.

Whilst reducing the present invention to practice, the present inventors have shown a synergistic effect of the inventive nanoparticles in combination with ibrutinib and PD-1/OX40 immune checkpoint therapy. This was validated in two tumor-bearing mouse models, with restricted melanoma growth and long-term survival (FIGS. 5A-N, 8A-G and 9A-C).

The present inventors further showed they were able to entrap inhibitory polynucleotide agents such as siRNA in the nanoparticles. Once taken up by dendritic cells, the siRNA was capable of specific downregulation of corresponding proteins. For example, nanoparticles grafted with dendritic cell targeting moieties and comprising siRNA, disease-associated antigens and adjuvants, were effective at controlling breast cancer growth and melanoma (FIGS. 14 and 15).

Additional results show that nanoparticles grafted with dendritic cell targeting moieties and comprising disease-associated antigens and adjuvants were also effective at controlling glioblastoma when administered with siRNA (FIG. 16).

Altogether, the present results suggest that combining disease-associated antigens and adjuvants in a single particle which has been decorated with a dendritic cell targeting moiety, results in a therapeutic which is capable of bringing about robust and widespread complementary outcomes. These results provide a strong basis for using such particles for the treatment of a myriad of diseases including solid tumors.

Thus, according to a first aspect of the present invention there is provided a polymeric nanoparticle comprising:

(i) at least one disease-associated antigen which is capable of producing a T-cell response, wherein the disease-associated antigen is encapsulated in the nanoparticle;

(ii) at least one adjuvant;

(iii) a dendritic cell targeting moiety which is attached to the outer surface of the nanoparticle; and (iv) a polynucleotide agent capable of downregulating an amount of a polypeptide in the dendritic cell, wherein the polynucleotide agent is encapsulated in the nanoparticle.

The present inventors further contemplate the same nanoparticles described herein above (except that they do not necessarily have to comprise the polynucleotide agent described in (iv)). Such nanoparticles further comprise (typically on the outer surface) d-α-tocopheryl polyethylene glycol 1000 succinate (TPGS).

As used herein, the term "nanoparticle" refers to a particle in the range between 10 nm to 1000 nm in diameter, wherein the diameter refers to the diameter of a perfect sphere having the same volume as the particle.

In some cases, the diameter of the particle is in the range of about 1-1000 nm, 10-500 nm, 20-300 nm, or 100-300 nm. In various embodiments, the diameter is about 100-200 nm.

In some cases, a population of particles may be present. As used herein, the diameter of the nanoparticles is an average of a distribution in a particular population.

The population of nanoparticles preferably have an average diameter no greater than 250 nm, and even no greater than 200 nm (e.g. 170 nm).

Examples of polymers that may be used to fabricate the nanoparticles of this aspect of the present invention include but are not limited to vinyl polymers, such as polyvinyl aromatics (e.g., polystyrene), polyacrylates (e.g., polymethyl acrylate, polyethyl acrylate), polymethacrylates (e.g., polymethyl methacrylate), polycyanoacrylates, polyacrylonitrile, polyvinyl halides (e.g., polyvinyl chloride, polyvinylidene fluoride, polyvinylidene chloride and/or polytetrafluoroethylene), polyvinyl ketones, polyvinyl ethers (e.g., polyvinyl methyl ether), polyvinyl esters (e.g., polyvinyl acetate) and/or polyvinyl alcohol; polyphosphoesters (e.g., poly[1,4-bis(hydroxyethyl)terephthalate-co-ethyloxyphosphate]); polyurethanes; polyphosphazenes; polyesters, such as polycaprolactone, polylactic acid (e.g., poly(L-lactic acid), poly(D-lactic acid) and/or poly(D,L-lactic acid), polyglycolic acid, polyhydroxybutyrate, polyhydroxyvalerate, polyalkylene succinates such as poly(1,4-butylene-co-succinate), polyalkylene oxalates, polydioxanone, alkyd resins, and polycarbonates (e.g., poly(trimethylene carbonate)); polyorthoesters; polyanhydrides; polyamides, such as nylon 6, nylon 66 and/or polycaprolactam; polyimides; polysaccharides (e.g., starch, cellulose, cellulose nitrates, cellulose ethers such as methylcellulose, ethylcellulose, hydroxypropylcellulose, hydroxypropylmethylcellulose and/or carboxymethylcellulose, cellulose esters such as cellulose acetate, cellulose propionate and/or cellulose butyrate, chitosan, dextrin, maltodextrin, agar, alginic acid and/or hyaluronic acid); polypeptides (e.g., collagen, fibrin and/or fibrinogen); polyethers, such as polyethylene glycol and polypropylene glycol; polyoxymethylenes; epoxy resins; silicones; polyolefins, such as polyethylene, polypropylene, polyisobutylene and/or ethylene-alpha-olefin copolymers; fluorinated polyolefins; and blends and copolymers (including, e.g., block copolymers and/or random copolymers) thereof.

Examples of copolymers include, without limitation, ethylene vinyl acetate copolymer, ethylene vinyl alcohol copolymer, poly(lactide-co-glycolide), poly(hydroxybutyrate-co-valerate), acrylonitrile-styrene and acrylonitrile-butadiene-styrene copolymers, ethylene methyl methacrylate copolymers, poly(ethylene oxide-co-lactic acid), polyethylene-maleic anhydride copolymers, and/or poloxamers.

According to a particular embodiment, the polymer is a biocompatible polymer.

The phrase "biocompatible polymer" refers to any polymer (synthetic or natural) which when in contact with cells, tissues or body fluid of an organism does not induce adverse effects such as immunological reactions and/or rejections, cellular death, and the like. A biocompatible polymer can also be a biodegradable polymer.

Particular examples of polymers that can be used to fabricate the nanoparticles include, but are not limited to poly(lactic acid), poly(ethylene glycol) (PEG), poly(glycolic acid) (PGA) and poly lactic acid-co-glycolic acid (PLGA).

The nanoparticle may comprise more than one polymer. Typically, the nanoparticle comprises PLA. The molecular weight of the PLA used is generally in the range of about 2,000 g/mol to 300,000 g/mol. Thus, in an embodiment, the PLA used is in the range of about 1,000 g/mol to 10,000 g/mol. The average molecular weight of PLA may also be about 1,600-2,400 g/mol.

The molecular weight of the PEG used is generally in the range of 100-50,000 g/mol and more specifically between 350010,000 g/mol. Thus, in one embodiment, when the PEG is comprised in a PEG-PLGA copolymer, the molecule weight of the PEG is about 3000. When the PEG is comprised in TPGS, the molecular weight of PEG is about 1000.

In one embodiment, the nanoparticle comprises at least one co-polymer, examples of which include PEG-PLGA, PEG-PLA, PLA-PEG-PLA, PEG-PLA-PEG, PEG-PCL, PEG-PCL-PEG, Poly lactide-co-caprolactone (PLA-PCL), Poly(Ethylene Glycol)-Poly(l-Glutamic Acid) (PEG-PGA), methoxy-poly(ethylene glycol)-b-poly(l-lactide-co-glycolide) (mPEG-PLGA), mPEG-PCL, mPEG-PLA, methoxy-PEG-PGA, 1,2-distearoyl-sn-glycero-3-phosphoethanolamine-N-[amino(polyethylene glycol)-2000] (DSPE-PEG).

Particular combinations of polymers include PLGA and PLA (for example at a ratio of 1:4); and PLGA and PEG-PLGA (for example at a ratio of 7:1 and 4:1).

As mentioned, the outer surface of the nanoparticles of this aspect of the present invention is decorated with dendritic cell targeting moieties.

The term "dendritic cell" or "DC" refers to any member of a diverse population of morphologically similar cell types found in lymphoid or non-lymphoid tissues. These cells are characterized by their distinctive morphology and high levels of surface MHC-class II expression. DCs can be isolated from a number of tissue sources. DCs have a high capacity for sensitizing MHC-restricted T cells, and are the only antigen-presenting cells (APCs) that can activate naive T-cells. The antigens may be self-antigens that are expressed during T cell development and tolerance, and foreign antigens that are present during normal immune processes.

As used herein, an "activated DC" is a DC that has been pulsed with an antigen and is capable of activating an immune cell. The term "mature DC," as used herein, is defined as a dendritic cell that expresses high levels of MHC class II, CD80 (B7.1) and CD86 (B7.2) molecules. In contrast, immature dendritic cells express low levels of MHC class II, CD80 (B7.1) and CD86 (B7.2) molecules but have a great capacity to take up an antigen.

The DC targeting moieties ensure that the nanoparticles are preferentially endocytosed by dendritic cells as compared to macrophages.

The DC targeting moiety may be an antibody (or fragment thereof), a protein or a peptide that binds to one or more dendritic cell surface marker(s). Such markers include, but are not limited to, DEC205, DC-SIGN, CD11c, DCIR2, Dectin-1/2, CD80/86, F4/80-like receptor, CIRE, mannose receptor, and CD36.

According to a particular embodiment, DC targeting moieties include but are not limited to carbohydrate-recognition domain ligands (such as mannose, PEG-mannose, galectin-3, tri-mannose, mannose-mimicking ligands (e.g.

shikomyl), galectin-3; and Dectin-1 agonists (e.g. laminarin, PEG-laminarin, β-glucan peptides), Dectin-2 agonists; agonists of C-type lectin receptors (e.g. Langerin agonist, DC-SIGN agonists, DEC-205 agonists); CD40 agonists).

The DC targeting moieties may be linked to a polymer (preferably a hydrophilic polymer such as PLGA or PEG-PLGA). Thus, for example the present inventors contemplate using mannose-PLGA or mannose-PEG-PLGA in their nanoparticles. Methods of linking DC targeting moieties to the polymer are known in the art and include the reaction of the carboxylic acid terminal groups of PLGA with mannosamine through carbodiimide (PLGA-mannose), or the reaction of amine-PEG-mannosamine with the PLGA-NHS (mannose-PEG-PLGA).

As mentioned, the polymeric nanoparticles encapsulate disease-associated antigens (e.g. cancer or infection associated antigens).

Disease-associated antigens are typically short peptides corresponding to one or more antigenic determinants of a protein. The disease-associated antigen typically binds to a class I or II MHC receptor thus forming a ternary complex that can be recognized by a T-cell bearing a matching T-cell receptor binding to the MHC/peptide complex with appropriate affinity. Peptides binding to MHC class I molecules are typically about 8-14 amino acids in length. T-cell epitopes that bind to MHC class II molecules are typically about 12-30 amino acids in length. In the case of peptides that bind to MHC class II molecules, the same peptide and corresponding T cell epitope may share a common core segment, but differ in the overall length due to flanking sequences of differing lengths upstream of the amino-terminus of the core sequence and downstream of its carboxy terminus, respectively. A T-cell epitope may be classified as an antigen if it elicits an immune response.

A peptide sequence may be synthesized by methods known to those of ordinary skill in the art, such as, for example, peptide synthesis using automated peptide synthesis machines, such as those available from Applied Biosystems, Inc. (Foster City, Calif.). Longer peptides or polypeptides also may be prepared, e.g., by recombinant means.

Disease-associated antigens of this aspect of the present invention include but are not limited to cancer antigens, infectious disease antigens such as bacterial antigens, viral antigens, fungal antigens or parasitic antigens, allergy antigens, autoimmune antigens and mixtures of these antigens.

The antigens for cancers can be antigens from testicular cancer, ovarian cancer, brain cancer such as glioblastoma, pancreatic cancer, melanoma, lung cancer, prostate cancer, hepatic cancer, breast cancer, rectal cancer, colon cancer, esophageal cancer, gastric cancer, renal cancer, sarcoma, neuroblastoma, Hodgkins and non-Hodgkins lymphoma and leukemia.

According to a particular embodiment, the disease-associated antigen is a cancer associated antigen.

In one embodiment, the disease-associated antigen is a cancer testis antigen (e.g. a member of the melanoma antigen protein (MAGE) family, Squamous Cell Carcinoma-1 (NY-ESO-1), BAGE (B melanoma antigen), LAGE-1 antigen, Brother of the Regulator of Imprinted Sites (BORIS) and members of the GAGE family).

In another embodiment, the disease-associated antigen is derived from MART-1/Melan-A protein e.g. (MART1 MHC class I peptides (Melan-A:26-35(L27), ELAGIGILTV; SEQ ID NO: 1) and MHC class II peptides (Melan-A:51-73(RR-23) RNGYRALMDKSLHVGTQCALTRR; SEQ ID NO: 2).

In another embodiment, the disease-associated antigen is derived from glycoprotein 70, glycoprotein 100 (gp100:25-33 (MHC class I (EGSRNQDWL—SEQ ID NO: 7)) or gp100:44-59 MHC class II (WNRQLYPEWTEAQRLD—SEQ ID NO: 8) peptides).

In still another embodiment, the disease-associated antigen is derived from tyrosinase, tyrosinase-related protein 1 (TRP1), tyrosinase-related protein 2 (TRP-2) or TRP-2/INT2 (TRP-2/intron2).

In still another embodiment, the disease-associated antigen comprises MUT30 (mutation in Kinesin family member 18B, Kif18b—PSKPSFQEFVDWENVSPELN-STDQPFL—SEQ ID NO: 9) or MUT44 (cleavage and polyadenylation specific factor 3-like, Cpsf31—EFKH-IKAFDRTFANNPGPMVVFATPGM—SEQ ID NO: 10).

In still another embodiment, the disease-associated antigen is derived from stimulator of prostatic adenocarcinoma-specific T cells—SPAS-1.

In still another embodiment, the disease-associated antigen is derived from human telomerase reverse transcriptase (hTERT) or hTRT (human telomerase reverse transcriptase).

In still another embodiment, the disease-associated antigen is derived from ovalbumin (OVA) for example $OVA_{257-264}$ MHCI H-2Kb (SIINFEKL—SEQ ID NO: 11) and $OVA_{323-339}$ MHCII I-A(d) (ISQAVHAAHAEINEAGR SEQ ID NO: 12), a RAS mutation, mutant oncogenic forms of p53 (TP53) (p53mut (peptide antigen of mouse mutated $p53_{R172H}$ sequence VVRHCPHHER—SEQ ID NO: 4 (human mutated $p53_{R175H}$ sequence EVVRHCPHHE—SEQ ID NO: 5)), or from BRAF-V600E peptide (GDFGLATEKSRWSGS—SEQ ID NO: 13).

In still another embodiment, the disease-associated antigen is a breast cancer associated disease antigen including but not limited to α-Lactalbumin (α-Lac), Her2/neu, BRCA-2 or BRCA-1 (RNF53), KNG1K438-R457 (kininogen-1 peptide) and C3fS1304-R1320 (peptides that distinguish BRCA1 mutated from other BC and non-cancer mutated BRCA1).

In still another embodiment, the disease-associated antigen is a colorectal cancer associated disease antigen including but not limited to MUC1, KRAS, CEA (CAP-1-6-D [Asp6]; YLSGADLNL—SEQ ID NO: 14) and $Adpgk_{R304M}$ MC38 (MHCI-Adpgk: ASMTNMELM SEQ ID NO: 15; MHCII-Adpgk: GIPVHLELASMTNMELMS-SIVHQQVFPT SEQ ID NO: 16).

In still another embodiment, the disease-associated antigen is a pancreatic cancer associated disease antigen including but not limited to CEA, CA 19-9, MUC1, KRAS, p53mut (peptide antigen of mouse mutated $p53_{R172H}$ sequence VVRHCPHHER—SEQ ID NO: 4 (human mutated $p53_{R175H}$ sequence EVVRHCPHHE—SEQ ID NO: 5)) and MUC4 or MUC13, MUC3A or CEACAM5, KRAS peptides (e.g. KRAS-G12R, KRAS-G13D, p5-21 sequence KLVVVGAGGVGKSALTI (SEQ ID NO: 17), p5-21 G12D sequence KLVVVGADGVGKSALTI (SEQ ID NO: 18), p17-31 sequence SALTIQLIQNHFVDE (SEQ ID NO: 19), p78-92 sequence FLCVFAINNTKSFED (SEQ ID NO: 20), p156-170 sequence FYTLVREIRKHKEKM (SEQ ID NO: 21), NRAS (e.g. NRAS-Q61R), PI3K (e.g. PIK3CA-H1047R), C-Kit-D816V, and BRCA mutated epitopes YIHTHTFYV (SEQ ID NO: 22) and SQIWNLNPV (SEQ ID NO: 23) HLA-A*02:01 restricted neoepitopes.

In still another embodiment, the disease-associated antigen is a lung cancer associated disease antigen including but not limited to Sperm Protein 17 (SP17), A-kinase anchor protein 4 (AKAP4) and Pituitary Tumor Transforming Gene 1 (PTTG1), Aurora kinase A, HER2/neu, and p53mut.

In still another embodiment, the disease-associated antigen is a prostate cancer associated disease antigen such as prostate cancer antigen (PCA), prostate-specific antigen (PSA) or prostate-specific membrane antigen (PSMA).

In still another embodiment, the disease-associated antigen is a brain cancer, specifically glioblastoma cancer associated disease antigen such as GL261 neoantigen (mImp3 D81N AALLNKLYA—SEQ ID NO: 6).

In another embodiment, the disease-associated antigen is a neoantigen.

As used herein the term "neoantigen" is an epitope that has at least one alteration that makes it distinct from the corresponding wild-type, parental antigen, e.g., via mutation in a tumor cell or post-translational modification specific to a tumor cell. A neoantigen can include a polypeptide sequence or a nucleotide sequence. A mutation can include a frameshift or nonframeshift indel, missense or nonsense substitution, splice site alteration, genomic rearrangement or gene fusion, or any genomic or expression alteration giving rise to a neoORF. A mutation can also include a splice variant. Post-translational modifications specific to a tumor cell can include aberrant phosphorylation. Post-translational modifications specific to a tumor cell can also include a proteasome-generated spliced antigen.

An example of a mutant APC antigen is QATEAERSF (SEQ ID NO: 24).

Examples of BRCA mutated epitopes are YIHTHTFYV (SEQ ID NO: 22) and SQIWNLNPV (SEQ ID NO: 23) HLA-A*02:01 restricted neoepitopes.

An examples of a universal HLA-DR-binding T helper synthetic epitope (AKFVAAWTLKAAA, SEQ ID NO: 25) is the pan DR-biding epitope (PADRE), which is a 13 amino acid peptide that activates CD4+ T cells.

Another contemplated disease-associated neoantigen is the GL261 neoantigen (mImp3 D81N, sequence AALLNK-LYA—SEQ ID NO: 6).

The antigens for bacterial infections can be antigens from *Escherichia coli, Salmonella enterica, Neisseria meningitis, Listeria monocytogenes*, bacterial *Meningitis, Chlamydia pneumoniae, Diptheria, Streptoccoccus pneumoniae, Strep-toccoccus aureus, Streptoccoccus bacteria, Helicobacter pylori, Haemophilus influenza* Serotype B, *Legionellosis, Mycoplasma pneumoniae, Pertussis*, scarlet fever, toxic shock syndrome, trachoma, urinary tract infections, anthrax, botulism, cholera, typhus, gonorrhea, impetigo, leprosy, leptospirosis, lyme disease, meliodosis, MRSA infection, nocardosis, *pertussis*, the plague, Pneumococcal pneumonia, psittacosis, Q fever, Rocky Mountain spotted fever, shigellosis, tetanus, tuberculosis, tularemia and typhoid fever and mixtures thereof. Fragments of these bacterial antigens can also be used as long as they stimulate antibody production.

Viral antigens can be antigens from AIDS, such as gag, tat nef, the envelope such as gp120 or gp 160 fragments thereof, Varicella, colds, Cytomegalovirus, Colorado tick fever, Dengue fever, Ebola haemorrhagic fever, hand foot and mouth disease, Rotavirus, Coronavirus, hepatitis, herpes simplex, herpes zoster, human papilloma virus, influenza, lassa fever, measles, Marbug hemorrhagic fever, infectious mononucleosis, mumps, poliomyelitis, progressive multifocal leukencephalopathy, rabies, rubella, SARS, variola-zoster virus, viral encephalitis, viral meningitis, viral pneumonia, West Nile disease, influenza A virus, Epstein-bar virus, respiratory syncytial virus, adult T cell leukemia virus, Hepatitis A virus, pox virus and yellow fever and mixtures thereof. Fragments of these viral antigens can also be used as long as they stimulate antibody production.

Fungal antigens that can be used in the present invention include antigens from allergic bronchopulmonary aspergillosis, pulmonary aspergilloma, athlete's foot, basidiobolomycosis, black piedra, blastomycosis, candidiasis, chytridiomycosis, coccidiodomycosis, conidiobolomycosis, covered smut, cryptococcosis, *Cryptococcus gatti*, dermatophytosis, dimorphic fungi, endothrix, entomopathogenic fungus, epizootic lymphangitis, esosphageal candidiasis, exothrix, fungemia, histoplasmosis, *Massospora cicadina*, mycosis, piedraia, pneumocystis pneumonia, *Sirococcus clavigignenti-juglandacearum*, sporotrichosis, thousand cankers disease, tinea, *Tinea barbae, Tinea capitis, Tinea corporis, Tinea crusis, Tinea faciei, Tinea incognito, Tinea nigra, Tinea versicolor*, thrush and white nose syndrome and mixtures thereof. Fragments of these fungal antigens can also be used as long as they stimulate antibody production.

Antigens that can be used to treat parasitic or protozoan infectious diseases include antigens from African trypanosomiasis, amebiasis, ascariasis, babesiosis, balatidiasis, chagas disease, clonorchiasis, coccidiosis, cryptosporidiosis, cysticercosis, diphyllobothriasis, dracunculiasis, echinococcosis, enterobiasis, fascioliasis, fasciolopsiasis, filariasis, free-living amebic infection, giardiasis, gnathostomiasis, helminths, hexamitiasis, hymenolepiasis, isosporiasis, leishmaniasis, malaria, metagonimiasis, myiasis, onchocerciasis, pediculosis, plasmonium, scabies, schistosomiasis, taeniasis, toxocariasis, toxoplasmosis, trichinellosis, trichuriasis, trichomoniasis and trypanosomiasis and mixtures thereof. Fragments of these parasitic or protozoan antigens can also be used as long as they stimulate antibody production.

Antigens that can be used to treat allergies include antigens from cigarette smoke allergies, chemical allergies, cloth allergies, cockroach allergies, dust mite allergies, food allergies, gastrointestinal allergies, grass pollen allergies, hay fever, house dust allergies, insect sting or bites allergies, latex allergies, mold allergies, pet allergies, pollen allergies, ragweed allergies and tree pollen allergies and mixtures thereof. Fragments of these allergy antigens can also be used as long as they stimulate antibody production.

The amount of the at least one antigen used in the compositions and/or methods of the present invention depends on the antigen that is used and thus varies with each different formulation. However, the at least one antigen should at least induce an immunoprotective response without adverse side effects. Generally the particle will contain between 0.1 to 1,000 µg of each antigen. In another aspect the particle will contain 0.1 to 500 µg of each antigen. In yet another aspect the particle will contain between 0.1 to 100 µg of each antigen. 0.1 to 50 µg of each antigen can also be used in the particle in yet another aspect.

The peptides of some embodiments of the invention may be synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing peptide chain. In one embodiment, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55(3):227-50.

In one embodiment, the peptides are synthesized by recombinant means.

In one embodiment, a polynucleotide agent encoding the peptide is present in the nanoparticle.

Preferably, at least 60%, 70%, 80%, 90%, 95%, 96%, 97%, 98%, 99% of the disease-associated antigens are encapsulated within the nanoparticle.

As mentioned, the nanoparticles described herein further comprise an adjuvant.

The term "adjuvant" as used herein refers to a substance that increases the ability of an antigen to stimulate the immune system.

According to a particular embodiment, the adjuvant comprises a Toll-like receptor ligand. Preferably, the TLR ligand is encapsulated within the nanoparticle.

The Toll-like receptor (TLR) ligand may be a ligand of TLR2, a ligand of TLR3, a ligand of TLR4, a ligand of TLR5, a ligand of TLR7/8 and/or a ligand of TLR9.

Examples of TLR ligands include, but are not limited to zymosan, Polyinosinic-polycytidylic acid (Poly(I:C)), Monophosphoryl Lipid A (MPLA)), flagellin, Gardiquimod, Imiquimod (R837) Resiquimod, Inducible T-cell co-stimulator ligand (ICOSL) and CpG oligodeoxynucleotides (CpG ODN).

As used herein "CpG oligodeoxynucleotides" are short DNA sequences bearing unmethylated CpG motifs that bind to the Toll-like receptor 9 (TLR9). TLR is a receptor expressed on B cells and plasmacytoid dendritic cells causing the up regulation of MHC and other stimulatory molecules, which in turn results in more potent APC mediated T cell stimulation. Examples of CpG oligodeoxynucleotides include ODN 2006, ODN D35, ODN 1018 ISS, ODN 1758, ODN 1826 (SEQ ID NO: 3), ODN 2216, ODN 2007, ODN 1668, ODN 1720, ODN 2006, ODN 2041, OSN 7909, CpG-28 and the like.

According to a particular embodiment, the nanoparticle comprises (e.g. encapsulates both CpG ODN 1826 and Poly(I:C).

According to another embodiment, the nanoparticle comprises (e.g. encapsulates both CpG ODN 1826 and Monophosphoryl Lipid A (MPLA).

Additional adjuvants can be comprised in the nanoparticles disclosed herein. These include, but are not limited to hyaluronic acid (HA), poloxamer 407 (Pluronic F127 (PL)), 2',3'-cGAMP, chitosan, poly-glutamic acid, poly-arginine, Dectin-1 agonist laminarin and β-glucan.

According to a particular embodiment, as well as encapsulating at least one Toll-like-receptor ligand, the nanoparticle comprises poloxamer 407 (Pluronic F127) or hyaluronic acid (HA).

According to a particular embodiment, as well as encapsulating at least one Toll-like receptor ligand, the nanoparticle comprises HA and PL.

It will be appreciated that the nanoparticles of the present invention may further comprise a surfactant.

Examples of such surface active agents include but are not limited to poly(vinyl alcohol) (PVA) and d-α-Tocopheryl polyethylene glycol 1000 succinate (TPGS).

According to a particular embodiment, the surfactant is TPGS.

As well as the components described herein above, the nanoparticles of the present invention may also encapsulate polynucleotide agents capable of downregulating the amount of a polypeptide.

Exemplary polypeptides that may be down-regulated include both soluble and non-soluble immune suppressive factors, but are not limited to TGF-β, VEGFA, PD-L1/PD-1, VEGFR1, VEGFR2, VEGFR3, IDO, RANKL, IL-10 and PGE2 receptor and pro-inflammatory cytokines and chemokines such as CXCL12, CCL2 or CCL7.

According to a particular embodiment, the polypeptide is PD-L1.

According to a particular embodiment, the polypeptide is TGF-β1.

Non-limiting examples of agents capable of down regulating expression are described in detail hereinbelow.

Down-regulation at the nucleic acid level is typically affected using a nucleic acid agent, having a nucleic acid backbone, DNA, RNA, mimetics thereof or a combination of same. The nucleic acid agent may be encoded from a DNA molecule or provided to the cell per se.

According to specific embodiments, the downregulating agent is a polynucleotide.

According to specific embodiments, the downregulating agent is a polynucleotide capable of hybridizing to a gene or mRNA encoding the relevant protein.

According to specific embodiments, the downregulating agent directly interacts with the relevant protein.

According to specific embodiments, the agent directly binds the relevant protein.

According to specific embodiments, the agent indirectly binds the relevant protein (e.g. binds an effector of the relevant protein).

According to specific embodiments the downregulating agent is an RNA silencing agent or a genome editing agent.

The nucleic acid agent may for complexed to a polymer in order to enhance stabilization thereof.

Exemplary polymers which can be used to complex to the nucleic acid agents (e.g. siRNA agents) include glutamate chitosan, poly-arginine, alkylated poly(a)glutamate amine (APA) and poly-(a)glutamic acid (PGA).

In one embodiment, downregulation of the relevant protein can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include non-coding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs.

In one embodiment, the RNA silencing agent is capable of inducing RNA interference.

In another embodiment, the RNA silencing agent is capable of mediating translational repression.

According to an embodiment of the invention, the RNA silencing agent is specific to the target RNA and does not cross inhibit or silence other targets or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene; as determined by PCR, Western blot, Immunohistochemistry and/or flow cytometry.

RNA interference refers to the process of sequence-specific post-transcriptional gene silencing in animals mediated by short interfering RNAs (siRNAs).

Following is a detailed description on RNA silencing agents that can be used according to specific embodiments of the present invention.

DsRNA, siRNA and shRNA—

The presence of long dsRNAs in cells stimulates the activity of a ribonuclease III enzyme referred to as dicer. Dicer is involved in the processing of the dsRNA into short pieces of dsRNA known as short interfering RNAs (siR-NAs). Short interfering RNAs derived from dicer activity are typically about 19 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment dsRNA longer than 30 bp are used. Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

According to some embodiments of the invention, dsRNA is provided in cells where the interferon pathway is not activated, see for example Billy et al., PNAS 2001, Vol 98, pages 14428-14433. and Diallo et al, Oligonucleotides, Oct. 1, 2003, 13(5): 381-392. doi: 10.1089/154545703322617069.

According to an embodiment of the invention, the long dsRNA are specifically designed not to induce the interferon and PKR pathways for down-regulating gene expression.

For example, Shinagwa and Ishii [*Genes & Dev.* 17 (11): 1340-1345, 2003] have developed a vector, named pDE-CAP, to express long double-strand RNA from an RNA polymerase II (Pol II) promoter. Because the transcripts from pDECAP lack both the 5'-cap structure and the 3'-poly (A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 base pairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is suggested to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned, the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-CAAGAGA-3' and 5'-UUACAA-3' (International Patent Application Nos. WO2013126963 and WO2014107763). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the relevant mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/ or translation initiation complexes may interfere with binding of the siRNA endonuclease complex [Tuschl Chem-Biochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi (dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNAs preferably include the same nucleotide composition as the siRNAs but lack significant homology to the genome. Thus, a scrambled nucleotide sequence of the siRNA is preferably used, provided it does not display any significant homology to any other gene.

For example, a suitable siRNA directed against TGFβ is set forth in SEQ ID NO: 26

(Sequence 5'-GGGCUACCAUGCCAACUUCtt-3').

A suitable siRNA directed against PD-L1 is set forth in SEQ ID BO: 27

(Sequence 5'-CCC ACA UAA AAA ACA GUU Gtt-3').

A suitable siRNA directed against VEGFR-3 is set forth in SEQ ID NO: 28

(Sequence 5'GAAGCCCAAUCAAUAACUGTT-3').

It will be appreciated that, and as mentioned hereinabove, the RNA silencing agent of some embodiments of the invention need not be limited to those molecules containing only RNA, but further encompasses chemically-modified nucleotides and non-nucleotides.

miRNA and miRNA Mimics—

According to another embodiment the RNA silencing agent may be a miRNA.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

Below is a brief description of the mechanism of miRNA activity.

Genes coding for miRNAs are transcribed leading to production of a miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nucleotide precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor Ex-portin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually becomes incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al. (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" or "miRNA mimic" refers to synthetic non-coding RNAs that are capable of entering the RNAi pathway and regulating gene expression. miRNA mimics imitate the function of endogenous miRNAs and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Preparation of miRNAs mimics can be effected by any method known in the art such as chemical synthesis or recombinant methods.

It will be appreciated from the description provided herein above that the nanoparticle may comprise the mature double stranded miRNA, the pre-miRNA or the pri-miRNA.

The pre-miRNA sequence may comprise from 45-90, 60-80 or 60-70 nucleotides.

The pri-miRNA sequence may comprise from 45-30,000, 50-25,000, 100-20,000, 1,000-1,500 or 80-100 nucleotides.

Antisense—

Antisense is a single stranded RNA designed to prevent or inhibit expression of a gene by specifically hybridizing to its mRNA. Downregulation of the relevant protein can be effected using an antisense polynucleotide capable of specifically hybridizing with an mRNA transcript encoding the protein.

Another agent capable of downregulating a protein is a DNAzyme molecule capable of specifically cleaving an mRNA transcript or DNA sequence of the protein. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc.

Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Another agent capable of downregulating a protein is a ribozyme molecule capable of specifically cleaving an mRNA transcript encoding a protein. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation.

Another agent capable of downregulating a protein is a RNA-guided endonuclease technology e.g. CRISPR system.

As used herein, the term "CRISPR system" also known as Clustered Regularly Interspaced Short Palindromic Repeats refers collectively to transcripts and other elements involved in the expression of or directing the activity of CRISPR-associated genes, including sequences encoding a Cas gene (e.g. CRISPR-associated endonuclease 9), a tracr (trans-activating CRISPR) sequence (e.g. tracrRNA or an active partial tracrRNA), a tracr-mate sequence (encompassing a "direct repeat" and a tracrRNA-processed partial direct repeat) or a guide sequence (also referred to as a "spacer") including but not limited to a crRNA sequence (i.e. an endogenous bacterial RNA that confers target specificity yet requires tracrRNA to bind to Cas) or a sgRNA sequence (i.e. single guide RNA).

In some embodiments, one or more elements of a CRISPR system is derived from a type I, type II, or type III CRISPR system. In some embodiments, one or more elements of a CRISPR system (e.g. Cas) is derived from a particular organism comprising an endogenous CRISPR system, such as *Streptococcus pyogenes, Neisseria meningitides, Streptococcus thermophilus* or *Treponema denticola*.

In general, a CRISPR system is characterized by elements that promote the formation of a CRISPR complex at the site of a target sequence (also referred to as a protospacer in the context of an endogenous CRISPR system).

In the context of formation of a CRISPR complex, "target sequence" refers to a sequence to which a guide sequence (i.e. guide RNA e.g. sgRNA or crRNA) is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. Thus, according to some embodiments, global homology to the target sequence may be of 50%, 60%, 70%, 75%, 80%, 85%, 90%, 95% or 99%. A target sequence may comprise any polynucleotide, such as DNA or RNA polynucleotides. In some embodiments, a target sequence is located in the nucleus or cytoplasm of a cell.

Thus, the CRISPR system comprises two distinct components, a guide RNA (gRNA) that hybridizes with the target sequence, and a nuclease (e.g. Type-II Cas9 protein), wherein the gRNA targets the target sequence and the nuclease (e.g. Cas9 protein) cleaves the target sequence. The guide RNA may comprise a combination of an endogenous bacterial crRNA and tracrRNA, i.e. the gRNA combines the targeting specificity of the crRNA with the scaffolding properties of the tracrRNA (required for Cas9 binding). Alternatively, the guide RNA may be a single guide RNA capable of directly binding Cas.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

In some embodiments, the tracr sequence has sufficient complementarity to a tracr mate sequence to hybridize and participate in formation of a CRISPR complex. As with the target sequence, a complete complementarity is not needed, provided there is sufficient to be functional. In some embodiments, the tracr sequence has at least 50%, 60%, 70%, 80%, 90%, 95% or 99% of sequence complementarity along the length of the tracr mate sequence when optimally aligned.

Introducing CRISPR/Cas into a cell may be effected using one or more vectors driving expression of one or more elements of a CRISPR system such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. A single promoter may drive expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron).

An additional method of regulating the expression of a gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo  | 3' -- A | G | G | T |
|--------|---------|---|---|---|
| duplex | 5' -- A | G | C | T |
| duplex | 3' -- T | C | G | A |

However, it has been shown that the A-AT and G-GC triplets have the greatest triple helical stability (Reither and Jeltsch, BMC Biochem, 2002 Sep. 12, Epub). The same authors have demonstrated that TFOs designed according to the A-AT and G-GC rule do not form non-specific triplexes, indicating that the triplex formation is indeed sequence specific.

Thus for any given sequence in the protein's regulatory region a triplex forming sequence may be devised. Triplex-forming oligonucleotides preferably are at least 15, more preferably 25, still more preferably 30 or more nucleotides in length, up to 50 or 100 bp.

The nanoparticles can be made using different methods such as attrition, pyrolysis, using thermal plasma methods, gas-phase techniques, multiple emulsion-solvent evaporation methods, gas-flow focusing, electrospray, fluidic nano-precipitation methods, emulsion diffusion-evaporation methods, modified phase inversion/solvent diffusion methods, or sol-gel methods. These methods are described in the literature and known to those skilled in the art.

According to one embodiment, the nanoparticles are generated by a double emulsion-solvent evaporation (w/o/w) method.

Thus, in one embodiment, the polymer used to fabricate the nanoparticle (e.g. PLGA/PLA) is dissolved in a solvent (e.g. dichloromethane (DCM)). It will be appreciated that the dendritic cell targeting moiety may be conjugated to the PLGA polymer. PEG-grafted PLGA or PEG-grafted PLA may also be used to improve the hydrophilicity of the nanoparticle and to promote DC targeted delivery. Lipid adjuvants (such as MPLA, α-galactosylceramide) may also be added at this stage. The disease antigens and Toll-like receptor (TLR) ligands are added to PVA and the two mixtures combined. An emulsification step then takes place to obtain an oil in water emulsion (o/w) which is subsequently added to a surfactant (such as TPGS). A second emulsification step then takes place to form the double emulsion water-in-oil-in-water (w/o/w). Finally, the w/o/w is added to PVA or alternatively PL.

In another embodiment, the particles are generated using a continuous microfluidic assembly (e.g. NanoAssemblr® from Precision Nanosystems).

In another embodiment, lipids such as phospholipids (e.g. 1-palmitoyl-2-oleoyl-sn-glycero-3-phosphocholine (POPC) and 1,2-Dimyristoyl-sn-glycero-3-phospho-rac-(1-glycerol) sodium salt (DMPG)) or PEG-grafted phospholipids (1,2-distearoyl-sn-glycero-3-phosphoethanolamine-N-[amino (polyethylene glycol)-2000 (DSPE-PEG)) are added to the polymer solution.

Below is a table summarizing exemplary formulations of the nanoparticles described herein together with their contemplated use.

TABLE 1A

| Formulation | Polymeric core | DC targeting moiety ligand | Disease-specific TAA | Toll-like receptor ligands | siRNA | Polymer to complex siRNA |
|---|---|---|---|---|---|---|
| Man-PLGA/PLA NP_GlutCs_PL_HA | Man-PLGA (lactide:glycolide 50:50, Mw 24,000-38,000)/ PLA 2 kDa (2:8) | Man-PLGA (lactide:glycolide 50:50, Mw 24,000-38,000)) | α-lactalbumin (α-Lac) protein | CpG oligodeoxynucleotides (CpG ODN 1826 - SEQ ID NO: 3)) Poly (I:C) (HMW; average size 1.5-8 kb) vaccine grade | siTGF-β1 | Glutamate chitosan (GlutCs; Mw 50,000-150,000 g/mol) |
| Man-PLGA/PLA NP_GlutCs_PL_HA | Man-PLGA (lactide:glycolide 50:50, Mw 24,000-38,000)/ PLA 2 kDa (2:8) | Man-PLGA (lactide:glycolide 50:50, Mw 24,000-38,000) | OVA protein | CpG ODN 1826 Poly (I:C) (HMW; average size 1.5-8 kb) vaccine grade | siTGF-β1 | GlutCs (Mw 50,000-150,000 g/mol) |
| mlmp3 D81N-loaded Man-PLGA/PLA NP_TPGS_PL | Man-PLGA (lactide:glycolide 50:50, Mw 24,000-38,000)/ PLA 2 kDa (2:8) | Man-PLGA (lactide:glycolide 50:50, Mw 24,000-38,000) | mlmp3 D81N GL261 MHC class I neoantigen peptides | CpG ODN 1826 Monophosphoryl Lipid A (MPLA) | No | NA |
| p53$_{R172H}$-loaded Man- PLGA/PLA NP_TPGS_PL | Man-PLGA (lactide:glycolide 50:50, Mw 24,000-38,000)/ PLA 2 kDa (2:8) | Man-PLGA (lactide:glycolide 50:50, Mw 24,000-38,000) | p53$_{R172H}$ MHC class I neoantigen peptides | CpG ODN 1826 Poly (I:C) (HMW; average size 1.5-8 kb) vaccine grade | No | NA |
| MUT30 -loaded Man- PLGA/PLA NP_TPGS_PL | Man-PLGA (lactide:glycolide 50:50, Mw 24,000-38,000)/ PLA 2 kDa (2:8) | Man-PLGA (lactide:glycolide 50:50, Mw 24,000-38,000) | MUT 30 B16F10 neoantigen MHC class II peptides | CpG ODN 1826 Poly (I:C) (HMW; average size 1.5-8 kb) vaccine grade | siPD-L1 | Amphiphilic alkylated poly(α)glutamate amine (APA; Mw = 253 g/mol) |
| MART1 -loaded Man- PLGA/PLA NP_TPGS_PL | Man-PLGA (lactide: glycolide 50:50, Mw 24,000-38,000)/ PLA 2 kDa (2:8) | Man-PLGA (lactide:glycolide 50:50, Mw 24,000-38,000) | MART1 MHC class I peptides (Melan-A: 26-35(L27) or MART1 MHC class II peptides (Melan-A:51-73(RR-23) | CpG ODN 1826 Poly (I:C) (HMW; average size 1.5-8 kb) vaccine grade | No | NA |
| gp100 -loaded Man-PLGA/PLA NP_TPGS_PL | Man-PLGA (lactide:glycolide 50:50, Mw 24,000-38,000)/ PLA 2 kDa (2:8) | Man-PLGA (lactide:glycolide 50:50, Mw 24,000-38,000) | gp100: 25-33 MHC class I (EGSRNQDWL) peptides or gp100: 44-59 MHC class II peptides | CpG ODN 1826) Poly (I:C) (HMW; average size 1,5-8 kb) vaccine grade | No | NA |
| OVA-loaded Man-PLGA/PLA NP_TPGS_PL | Man-PLGA (lactide:glycolide 50:50, Mw 24,000-38,000)/ PEG-PLGA (lactide:glycolide 50:50, PEG average Mw 2,000, PLGA average Mw 11,500))/ PLGA (lactide:glycolide 50:50, molecular weight (Mw) range 7,000-17,000 g/mol) (2:1:7) | Man-PLGA (lactide:glycolide 50:50, Mw 24,000-38,000) | OVA MHC class I peptides (OVA 257-264 MHCI H-2Kb sequence or OVA MHC class II peptides (OVA 323-339 MHCIII-A(d) sequence | CpG ODN 1826 Poly (I:C) (HMW; average size 1.5-8 kb) vaccine grade | siPD-L1 | Amphiphilic alkylated poly(α)glutamate amine (APA; Mw = 253 g/mol) |

TABLE 1A-continued

| | | | | | | |
|---|---|---|---|---|---|---|
| Adpgk MC38 - loaded Man-PLGA/PEG-PLGA NP | Man-PLGA (lactide:glycolide 50:50, Mw 24,000-38,000)/ PEG-PLGA (lactide:glycolide 50:50, PEG average Mw 2,000, PLGA average Mw 11,500)/ PLGA (lactide: glycolide 50:50, molecular weight (Mw) range 7,000-17,000 g/mol) (2:1:7) | Man-PLGA (lactide:glycolide 50:50, Mw 24,000-38,000) | Adpgk MC38 neoantigens MHC class I or Adpgk MC38 MHC class II | CpG ODN 1826 Poly (I:C) (HMW; average size 1.5-8 kb) vaccine grade | siPD-L1 | Polyarginine (Mw ranging 3,000-3,400 g/mol) |
| Adpgk MC38 - loaded Man-PEG-PLGA NP | Man-PEG-PLGA (lactide: glycolide 50:50, Mw 24,000-38,000; PEG MW 3,000 Da)/PLGA (lactide: glycolide 50:50, molecular weight (Mw) range 7,000-17,000 g/mol) (2:8) | Man-PEG-PLGA (lactide: glycolide 50:50, Mw 24,000-38,000; PEG MW 3,000 Da) | Adpgk MC38 neoantigens MHC class I peptides or Adpgk MC38 MHC class II peptides | CpG ODN 1826 Poly (I:C) (HMW; average size 1.5-8 kb) vaccine grade | siPD-L1 | Polyarginine (Mw ranging 3,000-3,400 g/mol) |

| Formulation | Emulsifying active agents | Other immune active adjuvants | Cancer Disease | nanovaccine combinations | Nanovaccine route of administration |
|---|---|---|---|---|---|
| Man-PLGA/PLA NP_GlutCs_PL_HA | Poly(vinyl alcohol) (PV A) Mw 13,000-23,000 Da | Hyaluronic acid (HA) & Poloxamer 407 (Pluronic F-127-PL) | Triple negative breast cancer (TNBC) - 4T1 primary | Anti-OX40, anti-PD-1, ibrutinib | Subcutaneous (SC) |
| Man-PLGA/PLA NP_GlutCs_PL_HA | PVA (Mw 13,000-23,000 Da) | PL | Primary melanoma - B16MO5 | Anti-OX40 | SC |
| mlmp3 D81N-loaded Man-PLGA/PLA NP_TPGS_PL | d-α-Tocopheryl polyethylene glycol 1000 succinate (TPGS) | PL | Glioblastoma GL261 | P-Selectin knockdown (shSELP) | Nasal |
| p53ri72h -loaded Man- PLGA/PLA NP_TPGS_PL | TPGS | PL | Pancreatic ductal adenocarcinoma (PDAC)- KPC | NA | Nasal versus SC |
| MUT30 -loaded Man- PLGA/PLA NP_TPGS_PL | TPGS | PL | Primary melanoma - B16F10 | Anti- PD-L1 | Nasal |
| MARTI -loaded Man- PLGA/PLA NP_TPGS_PL | TPGS | PL | Melanoma brain metastases - B16F10 | NA | Nasal |
| gp100 -loaded Man-PLGA/PLA NP_TPGS_PL | TPGS | PL | Primary melanoma - D4M.3A | NA | Nasal |
| OVA-loaded Man-PLGA/PLA NP_TPGS_PL | TPGS | PL | Primary melanoma - B16MO5 | NA | Nasal |
| Adpgk MC38 - loaded Man-PLGA/PEG-PLGA NP | PVA (Mw 13,000-23,000 Da) | | Primary Colorectal cancer (CRC) - MC38 | | SC |
| Adpgk MC38 - loaded Man-PEG-PLGA NP | | | Primary Colorectal cancer (CRC) - MC38 | | SC |

In one embodiment, the nanoparticles are used as a vaccine.

As used herein, the term "vaccine" refers to a pharmaceutical preparation (pharmaceutical composition) or product that upon administration induces an immune response, in particular a cellular immune response, which recognizes and attacks a pathogen or a diseased cell such as a cancer cell.

Various regimens of administration are contemplated by the present invention. For example, an exemplary regimen comprises vaccinating on at least two separate occasions. According to one embodiment a period of time of about one week, two weeks, three weeks, four weeks or more is waited between each inoculation. The nanoparticles can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the nanoparticles accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, ocular, nasal, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (nanoparticles) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to ensure that levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The nanoparticles disclosed herein are capable of being used in combination with other therapeutics. Alternatively, the additional therapeutic may be formulated (e.g. entrapped) inside the nanoparticle.

Examples of therapeutics that can be used in conjunction with the nanoparticles disclosed herein (or may be formulated inside the nanoparticle) include, but are not limited to: immunomodulatory cytokines, including but not limited to, IL-2, IL-15, IL-7, IL-17, IL-21, GM-CSF as well as any other cytokines that are capable of further enhancing immune responses; and immunomodulatory drugs including, but not limited to, lenalidomide (Revlimid).

According to a particular embodiment, the nanoparticles of the present invention are administered together with (or formulated to include within) at least one immune checkpoint protein modulator (either a stimulatory immune checkpoint protein modulator or an inhibitory immune checkpoint protein modulator).

Examples of stimulatory immune checkpoint proteins include, but are not limited to OX40, CD27, CD40, GITR, CD137, CD28, HVEM and ICOS.

Examples of inhibitory immune checkpoint proteins include but are not limited PD-1, adenosine $A_{2A}$ receptor, B7-H3, B7-H4, BTLA, CTLA-4, IDO, KIR, LAG-3, PD-L1, TIM-3, TIGIT and VISTA (C10orf54).

The modulator may be an inhibitory antibody or small molecule directed against the immune checkpoint protein—e.g. anti-CTLA4, anti-CD40, anti-41BB, anti-OX40, anti-PD1 and anti-PDL1.

Additional agents that may be co-administered to the subject (together with the nanoparticles disclosed herein) or formulated inside the nanoparticles are inhibitors of myeloid derived suppressor cells (MDSCs). The inhibitors may act to inhibit infiltration, differentiation and/or polarization of MDSCs. Such inhibitors include Brutons tyrosine kinase (Btk) inhibitors including but not limited to ibrutinib or acalntunib (which are non-selective MDSC inhibitors), cyclophosphamide, curcumin, or RTK (receptor tyrosine kinases) inhibitors such as sunitinib, vatalanib and dovitinib.

Examples of such inhibitors include, but are not limited to ibrutinib, acalabrutinib, Evobrutinib, tirabrutinib and zanubrutinib, Naquotinib and Spebrutinib.

Yet additional agents that may be co-administered to the subject (together with the nanoparticles disclosed herein) or formulated inside the nanoparticles are modulators oligonucleotides, small molecules, enzymes) of cancer-related metabolic pathways (e.g. asparagine metabolism pathways, glutamine).

Yet additional agents that may be co-administered to the subject (together with the nanoparticles disclosed herein) or formulated inside the nanoparticles are modulators of genes/pathways that regulate the gut microbiome (e.g. mucin, inulin) with impact on TLRs and inflammasome components within dendritic cells.

In addition, the nanoparticles disclosed herein may be administered in combination with chemotherapy in regimens that do not inhibit the immune system including, but not limited to cyclophosphamide and taxol. The vaccines may also be administered for cancer in combination with therapeutic antibodies including, but not limited to, anti-HER2/neu (Trastuzumab), anti-EGFR (Cetuximab) and anti-CD20 (Rituximab). It will be appreciated that the present invention further contemplates formulating the nanoparticles to include (e.g. entrap) said agents.

The nanoparticles and the additional agent described herein above may be formulated in a single pharmaceutical composition or may be provided separately.

In the context of any of the combination therapies described herein above, the nanoparticles may be administered by the same route of administration (e.g. intranasal or subcutaneous) that the additional agent is administered. In the alternative, the nanoparticles may be administered by a different route of administration.

The nanoparticles can be administered immediately prior to (or after) the second agent, on the same day as, one day before (or after), one week before (or after), one month before (or after), or two months before (or after) the second agent and the like.

The nanoparticles and the second agent can be administered concomitantly, that is, where the administering for each of these reagents can occur at time intervals that partially or fully overlap each other. The nanoparticles and the second agent ination can be administered during time intervals that do not overlap each other. For example, the nanoparticles can be administered within the time frame of $t=0$ to 1 hours, while the second agent can be administered within the time frame of $t=1$ to 2 hours. Also, the nanoparticles can be administered within the time frame of $t=0$ to 1 hours, while the second agent can be administered somewhere within the time frame of $t=2$-3 hours, $t=3$-4 hours, $t=4$-5 hours, $t=5$-6 hours, $t=6$-7 hours, $t=7$-8 hours, $t=8$-9 hours, $t=9$-10 hours, and the like. Moreover, the nanoparticles can be administered somewhere in the time frame of $t=$minus 2-3 hours, $t=$minus 3-4 hours, $t=$minus 4-5 hours, $t=5$-6 minus hours, $t=$minus 6-7 hours, $t=$minus 7-8 hours, $t=$minus 8-9 hours, $t=$minus 9-10 hours.

The nanoparticles and the second agent are typically provided in combined amounts to achieve therapeutic or prophylactic effectiveness. This amount will evidently depend upon the particular agent selected for use, the nature of the nanoparticles used, the condition(s) to be treated or prevented, the species, age, sex, weight, health and prognosis of the subject, the mode of administration, effectiveness of targeting, residence time, mode of clearance, type and severity of side effects of the pharmaceutical composition and upon many other factors which will be evident to those of skill in the art. The nanoparticles will be used in an amount at which therapeutic or prophylactic effectiveness in combination with the second agent will be observed.

The second agent may be administered at a gold standard dosing as a single agent, below a gold standard dosing as a single agent or above a gold standard dosing as a single agent.

According to specific embodiments, the second agent is administered below gold standard dosing as a single agent.

As used herein the term "gold standard dosing" refers to the dosing which is recommended by a regulatory agency (e.g., FDA), for a given tumor at a given stage.

According to other specific embodiments the second agent is administered at a dose that does not exert at least one side effect which is associated with the gold standard dosing. Thus, in one preferred embodiment, the amount of the second agent is below the minimum dose required for therapeutic or prophylactic effectiveness when used as a single therapy (e.g. 10-99%, preferably 25 to 75% of that minimum dose). This allows for reduction of the side effects caused by the second agent, but the therapy is rendered effective because the combinations are effective overall.

As well as lowering the dose of the second agent, the present inventors contemplate that the amount of time over which the agents are administered may be reduced and/or the frequency of dosing may also be reduced.

In one preferred aspect of the present invention, the nanoparticles and the second agent are synergistic with respect to their dosages. That is to say that the effect provided by the combined treatment is greater than would be anticipated from the additive effects of the nanoparticles and second agent when used separately. In an alternative but equally preferred embodiment, the nanoparticles and the second agent are synergistic with respect to their side effects. That is to say that the side-effects caused by the nanoparticles in combination with the second agent are less than would be anticipated when the equivalent therapeutic effect is provided by either the nanoparticles or by the second agent when used separately.

The nanoparticles described herein can be used for treating/preventing diseases. In one embodiment, the disease is associated with cell growth including cancer.

Examples of cancer which may be treated include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, etc.

According to a particular embodiment the cancer is breast cancer (e.g. triple negative breast cancer), colorectal cancer, glioblastoma, pancreatic ductal adenocarcinoma or melanoma. As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Materials:

Poly(L-lactic acid) (PLA, 2000 Da) with an average molecular weight (Mw) of 2000 was purchased from PolySciences, Inc., UK. Tumor-associated peptides MHCI-restricted Melan-A:26-35(L27), ELAGIGILTV (SEQ ID NO: 1), (MHCI-ag), and MHCII-restricted Melan-A:51-73(RR-23), RNGYRALMDKSLHVGTQCALTRR (SEQ ID NO: 2; MHCII-ag) were purchased to GeneCust Europe. CpG ODN 1826 (SEQ ID NO: 3; TCCATGACGTTCCTGACGTT) was purchased from InvivoGen (San Diego, CA, USA). MEM a, nucleosides, no ascorbic acid was purchased from Invitrogen. RPMI 1640, heat inactivated fetal bovine serum (FBS), trypsin EDTA 0.05%, penicillin (10,000 Unit/ml) and streptomycin (10, 000 µg/ml) (Cat. #15140122), sodium pyruvate (100 mM), GM-CSF recombinant mouse protein (5 ng/ml), HEPES buffer (1 M), ACK lysing buffer, paraformaldehyde (PFA) 4% (v/v), Wheat Germ Agglutinin (WGA), Alexa Fluor® 633 Conjugate (Cat. #W21404), Hoechst® 33342 (Cat. #H3570) and AlamarBlue® reagent were purchased from Thermo Fisher Scientific. Proteome Profiler Mouse XL Cytokine Array Kit was purchased from R&D Systems, Inc. (Minneapolis, MN, USA). Matrigel Matrix (Cat. no. 356231) was purchased from BD Biosciences—Discovery Labware, Erembodegem, Europe. IncuCyte® Caspase-3/7 Apoptosis Assay Reagent (Cat No 4440) was acquired from Biological Industries Israel Beit-Haemek Ltd. PLGA (Resomer 503H; Mw 24 000-38 000), mannosamine.HCl, dimtehylformamide (DMF), 4-dimethylaminopyridine (DMAP), N,N-Dicyclohexylcarbodiimide (DCC), methanol, anhydrous sodium sulfate, Concanavalin A, FITC-labeled Concanavalin A from *Canavalia ensiformis* (Jack bean) Type IV lyophilized powder, Lipid A monophosphoryl from *Salmonella enterica* serotype minnesota Re 595 (Re mutant) (MPLA), bovine serum albumin, d-α-tocopherol polyethylene glycol 1000 succinate (TPGS), Poly(vinyl alcohol) (PVA) Mw 13,000 to 23,000 Da, 99% hydrolyzed, dichloromethane (DCM) and chloroform-d were purchased from Sigma Aldrich. PD-1 and OX40 monoclonal antibodies were acquired from Bio X cell. Rabbit monoclonal anti-caspase 3 was purchased from Epitomics (CA, USA). Antibodies anti-mouse CD4 (clone: CK1.5), CD8a (clone: 53-6.7) and DAPI were acquired from BioLegend (San Diego, CA, USA). Streptavidin-horseradish peroxidase conjugate was purchased from Histostain, Life Technologies (CA, USA). Fluorochrome labeled antibodies for flow cytometry were purchased from Miltenyi Biotech.

Synthesis and Characterization of Mannose-PLGA Polymer:

Mannose-PLGA (man-PLGA) was synthesized from PLGA (Resomer 503H; Mw 24,000-38,000 Da). Carboxylic acid terminal groups of PLGA were modified with mannosamine under nitrogen atmosphere in mild conditions (Alonso-Sande, M. et al. Biomacromolecules 14, 4046-4052, doi:10.1021/bm401141u (2013)). Briefly, Mannosamine.HCl (10.8 mg, 0.05 mmol, 3.5 eq.) and 4-dimethylaminopyridine (DMAP) (6.5 mg, 0.05 mmol, 4 eq.) were added to 4 ml of dimethylformamide (DMF). The mixture was stirred for 10 minutes at room temperature to achieve complete dissolution of mannosamine. PLGA (Resomer 503H; Mw 24 000-38 000) (400 mg, 0.0133 mmol, 1 eq.) was added to the previous solution and stirred for 10 minutes at room temperature. N,N'-Dicyclohexylcarbodiimide (DCC) (5.5 mg, 0.027 mmol, 2 eq.) was added to induce the reaction between PLGA and mannosamine. The reaction was allowed to stir for 48 h at room temperature under argon atmosphere. The polymer was precipitated with water and recovered by centrifugation. Man-PLGA was dissolved in DCM and anhydrous sodium sulfate was used to remove remaining water. The solution was filtered. DCM was evaporated through rotary evaporation until an oil was obtained. Methanol was added to precipitate the polymer and wash the reaction crude. Methanol was discarded. Man-PLGA was dissolved in DCM again and the procedure was repeated. Finally, man-PLGA was dried under vacuum overnight and weighed after 24 hours (186.7 mg; 11=47%). $^1$H NMR of man-PLGA was acquired at 300 K using a Bruker Avance NMR spectrometer at 300 MHz. Instrument was equipped with a 5 mm BBO probe including Z-axis pulse field gradients. NMR spectra were processed using Bruker NMR Suite 3.5 and MestReNova 10.0. Chemical shifts are reported relative to the deuterated solvent used (CDCl$_3$ δ 7.26 pmm).

Synthesis of NP and Man-NP:

PLGA/PLA NP were formulated by the double emulsion-solvent evaporation (w/o/w) method (Alonso-Sande, M. et al. 14, 4046-4052, doi:10.1021/bm401141u (2013)). PLGA/PLA (2:8) blend was dissolved in dichloromethane (DCM) at 50 mg/ml. MPLA (100 µg) was added to DCM polymer solution. A 10% (m/v) PVA aqueous solution (100 µl) containing CpG at 0.5 mg/ml and melan-A/MART-1 (26-35 (A27L) or melan-A/MART-1 (51-73) at 5 mg/ml was added to DCM. For empty NP, 100 µl of 10% PVA aqueous solution was added. The mixture was emulsified with a microprobe ultrasonic processor for 15 seconds at 20% amplitude. TPGS aqueous solution 2.5% (m/v) (400 µl) was added and the second emulsion was formed using the same conditions. The double emulsion was added dropwise into a 0.25% (m/v) PVA aqueous solution and stirred for 1 hour at room temperature. Particle suspension was collected by centrifugation at 20,000 g for 45 minutes, 4° C. (SOR-VALL® RC-5B PLUS Superspeed centrifuge). Particles were washed with ultrapure water, collected by centrifugation and finally resuspended in PBS or ultrapure water. Mannose-PLGA/PLA nanoparticles (man-NP) were prepared as described above, now with man-PLGA/PLA (2:8) blend instead. Cy5.5-labeled NP and man-NP were synthesized by adding 0.5 µg to the polymer blend.

Size Distribution and ζ-Potential Measurements:

Particle size was measured by Dynamic Light Scattering (DLS) with Malvern Nano ZS (Malvern Instruments, UK). Z-average size was determined by cumulative analysis. ζ-Potential of particles was measured by Laser Doppler Velocimetry (LDV) in combination with Phase Analysis Light Scattering (PALS) with the same equipment. Particles were diluted in ultrapure water and electrophoretic mobility was determined at 25° C. with the Helmholtz-von Smoluchowski model.

Particle morphology:

Atomic Force Microscopy (AFM). Particles were diluted at 5 mg/ml in ultrapure water. A drop of sample was placed onto freshly cleaved mica for 20 minutes and dried with pure $N_2$. Samples were analyzed by AFM in tapping mode in air at room temperature, using a Nanoscope Ma Multimode Atomic Force Microscope (Digital Instruments, Veeco), and etched silicon tips (ca. 300 kHz), at a scan rate of ca. 1.6 Hz.

Scanning Electron Microscopy (SEM). Particles were diluted in trehalose 5% (m/v) and fast frozen at –80° C. for 2 hours. Samples were dried under vacuum, first at –20° C. for 14 hours and then at 20° C. for 2 hours. Dried specimens were coated with gold on a Peltier-cold stage sputter-coater and examined using a FEI Quanta 200 FEG ESEM Phillips 500 scanning electron microscope at 5 kV accelerating voltage.

Transmission Electron Microscopy. Particles were diluted in PBS and placed on a carbon-coated copper grid and dried. Samples were analyzed by Philips CM 120 Bio-Twin TEM.

Entrapment Efficiency and Loading Capacity of Antigens and Immune Potentiators:

Supernatants collected from centrifugations were used for indirect quantification of entrapped antigens and immune potentiators. Entrapment efficiency (EE % (m/m), Eq. (1)) and loading capacity (LC µg/mg, Eq. (2)) of melan-A/MART-1 (26-35(A27L)) and melan-A/MART-1 (51-73) were determined with FAM-labeled melan-A/MART-1 (26-35(A27L)) and melan-A/MART-1 (51-73), respectively. Relative Fluorescence Units (RFU) were measured with SpectraMax M5e plate reader (Molecular Devices, CA, USA) at 498/518 nm, excitation/emission wavelengths. The amount of CpG in the supernatant was determined by the Oligreen® ssDNA quantitation kit (Silva, J. M. et al. J Control Release 198, 91-103, doi:10.1016/j.jconrel.2014.11.033 (2015)). RFU were measured using the fluorometer at 485 nm excitation and 530 nm emission wavelengths.

$$Entrapment\ Efficiency\ (EE\ \%) = \qquad (1)$$
$$\frac{initial\ amount\ of\ agent - amount\ of\ agent\ in\ the\ supernatant}{initial\ amount\ of\ agent} \times 100$$

-continued $$Loading\ Capacity\ (LC\ \mu g/mg) = \frac{initial\ amount\ of\ agent - amount\ of\ agent\ in\ the\ supernatant}{total\ amount\ of\ polymer} \qquad (2)$$

Mannose Detection on the Particles' Surface by the Lectin Recognition Assay:

Mannose residues at the surface of man-NP were detected by the Lectin Recognition Assay. Man-NP (1 mg/ml) were incubated under gentle stirring at 37° C. for 1 hour with Concanavalin A (Conc A, 0.7 mg/ml) in PBS (pH 7.2) supplemented with 1 mM $MnCl_2$, 1 mM $CaCl_2$ and 3% (m/v) BSA. Non-targeted NP were used as negative control. Particles were washed twice by centrifugation at 20,000 g for 45 minutes at 4° C., with supplemented PBS without BSA. The formation of aggregates was assessed by DLS, using a Malvern Nano ZS (Malvern Instruments, UK). The experiment was repeated with FITC-labeled Conc A. The formation of aggregates was detected by fluorescence microscopy.

Cell Lines:

Murine bone marrow dendritic cells (DC) JAWSII cell line (ATCC #CRL-11904) were cultured in MEM a, nucleosides, with no ascorbic acid, supplemented with 10% (v/v) FBS, 1% PEST (Penicillin 10,000 U/ml and -Streptomycin 10,000 µg/ml)), 1% Sodium Pyruvate (Sodium Pyruvate (100 mM)), 5 ng/ml GM-CSF Recombinant Mouse Protein. Ret melanoma cells were obtained from spontaneously occurring skin tumor in Ret transgenic mice and engineered to express mCherry reporter gene. Ret-mCherry melanoma cells (RMS) or unlabeled Ret melanoma cells were cultured in RMPI-1640 and supplemented with L-glutamine (2 mM), medium, with 10% FBS, 1% PEST (Penicillin 10,000 U/ml and Streptomycin 10,000 µg/ml), sodium pyruvate (1 mM) and HEPES (25 mM). B16-F10 cell line (ATCC® CRL-6475) was obtained from American Type Culture Collection (ATCC, Manassas, VA, USA). These cells were cultured in DMEM medium with 10% (v/v) inactivated FBS and 1% (v/v) penicillin/streptomycin solution.

In Vitro Cell Viability in the Presence of NP or Man-NP:

Cell viability of JAW SII DC was assessed by Alamar-Blue® assay. Briefly, $10^4$ cells were seeded in 96-well plates and incubated overnight. Cells were then treated with different concentrations of particles for 48 hours. Alamar-Blue® reagent was added at 10% (v/v) and incubated for 8 hours. Fluorescence measurements were performed at excitation wavelength of 530 nm and emission of 590 nm with a FLUOstar Omega microplate reader (BMG Labtech, Ortenberg, Germany). Triton X-100 0.5% (v/v) and cell culture medium were used as positive and negative controls, respectively.

Hemolysis Assay.

Mouse red blood cell (RBC) solution 2% (m/v) was incubated with serial dilutions of NP and man-NP for 1 hour at 37° C. The highest particle concentration (20 mg/ml) is the one used for injection in the in vivo experiments. Sodium dodecyl sulfate (SDS) was used as a positive control and dextran (Mw 70 kDa) as a negative control. Following centrifugation, the supernatant absorbance was measured at 550 nm using a SpectraMax M5e plate reader (Molecular Devices, CA, USA). The results were expressed as percentage of hemoglobin released by % (m/v) of Triton X100 (100% lysis).

43

44

In Vitro Particle Internalization by Dendritic Cells:

JAW SII DC ($5 \times 10^4$ cells/well) were seeded in 96-well plates and incubated overnight. Cells were then incubated with rhodamine-grafted NP or man-NP (500 µg/ml) for 4, 12 and 24 hours. Cells were then washed with DPBS and resuspended in flow cytometry buffer. Non-treated cells and non-labeled NP were used as negative controls. An excess of soluble mannose (5 mM) was added to medium, as a control to confirm its ability to compete with man-NP for CD206 at DC surface. The individual fluorescence JAW SII DC was collected for each sample using LSR Fortessa cytometer (BD Biosciences) by Facs Diva, and analyzed with FlowJo software version 7.6.5 for Microsoft (TreeStar, San Carlos, CA).

8-well Ibidi® microscopy chambers were incubated with 300 µL fibronectin (10 µg/mL) per well during 30 min in a humidified incubator with 5% $CO_2$, at 37° C.

After discarding the volume of fibronectin, JAW SII cells ($5 \times 10^4$ cells/well) were seeded in 8-well Ibidi® microscopy chambers for 6 hours in a humidified incubator with 5% $CO_2$, at 37° C. Cells were incubated with rhodamine-grafted NP or man-NP (500 µg/ml) for 3 hours. Non-treated cells and non-labeled NP were used as negative controls. Cells were washed and fixed at room temperature in 4% paraformaldehyde, containing Hoechst®332 at 2 µg/mL and WGA Alexa Fluor 633 at 5 µg/mL to stain the nucleus and the cell membrane, respectively. Each well was washed three times with PBS and 100 µL of fluoromount were added to each one. Particle internalization was observed by confocal microscopy using Zeiss LSM 710 with 63x amplification in oil. Images were processed with ImageJ software. Three-dimensional (3D) projection images were obtained from 0.4 µm Z-stacks and processed using the Leica Application Suite-Advanced Fluorescence (LAS-AF) software.

Animal Studies:

All animal procedures were completed in compliance with Tel Aviv University, Sackler Faculty of Medicine guidelines and protocols were approved by the institutional animal care and use committee (IACUC) and performed in accordance with NIH guidelines.

Male C57BL/6J mice (8 weeks old) were purchased from Envigo LTD (Jerusalem, Israel) and housed in the animal facility of Tel Aviv University. Mice body weight change was monitored 3 times per week. Mice were euthanized according to ethical protocol when showing signs of distress or with rapid weight loss (above 10% within a few days or 20% from the initial weight). For tumor-bearing mice, animals were also euthanized in case the tumor size exceeded 2000 $mm^3$ or if the tumor was necrotic or ulcerative. Mice were perfused intracardially with PBS, immediately after euthanasia, tumors were dissected and incubated in 4% PFA. Tumors were collected for histology.

In Vivo Study of Man-NP Internalization by DC in Draining Lymph Nodes:

Male C57BL/6, 8 weeks old mice (n=3/group) were injected into the right hind by the subcutaneous (s.c.) hock immunization with one of the Cy5.5 fluorescently-labeled plain and antigen-loaded NP formulations (2 mg of NP/mouse). Left non-injected hind served as negative control. All formulations contained MART-1 antigens and TLR ligands. Popliteal and inguinal lymph nodes were harvested 16 hours post-immunization (p.i.). A single-cell suspension was stained with fluorescent-labeled anti-mouse antibodies against CD11c, MHCII (I-Ab), MHCI (H-2Kb), CD80 and CD86, for 20 min at 4° C. Samples were acquired with an LSR II Fortessa flow cytometer (BD Bioscience) and analyzed with FlowJo software (Treestar).

Immunization of Animals with Tumor-Associated Antigens:

For immunization studies, 8 weeks old C57BL/6J male mice were randomized into 8 groups (N=6) (Table 1B).

TABLE 1B

| Immunization study design | |
| --- | --- |
| Group | Treatment |
| 1 | PBS |
| 2 | NP (empty) |
| 3 | MHCI-ag/CpG/MPLA (free) |
| 4 | MHCI-ag/MHCII-ag (free) |
| 5 | NP MHCI-ag |
| 6 | NP MHCI-ag/NP MHCII-ag |
| 7 | man-NP MHCI-ag |
| 8 | man-NPMHCI-ag/man-NP MHCII-ag |

Obs: Groups from 3 to 8 included the administration of both melanoma-associated peptides (MHCI-ag or MHCI-ag/MHCII-ag) and Toll-like receptor ligands (CpG and MPLA).

Treatments (100 µl) were injected into each mouse by hock immunization, via subcutaneous injection proximal to popliteal and axillary LN. Half dose was injected into the right side and the other half into the left side. When the two peptide antigens melan-A/MART-1 (26-35(A27L)) and melan-A/MART-1 (51-73) were administered to the same mouse (groups 4, 6, and 8), 25 µl of each treatment was administered on each side. Each dose contained 100 µg of antigen (50 µg of melan-A/MART-1 (26-35(A27L)) and 50 µg of melan-A/MART-1 (51-73), when two antigens were used), plus 20 µg of CpG and 20 µg of MPLA, either free in solution or entrapped in 2 mg of particles (20 mg/ml).

Tumor Antigen Specific Proliferation of Splenocytes from Immunized Mice:

Splenocytes from whole spleens of treated mice (N=6) were harvested and seeded in sterile 60 mm petri dishes, 10 days after the last immunization. Splenocytes were seeded for 6 days in complete RPMI medium, in the presence of melan-A/MART-1 (26-35(A27L)) or melan-A/MART-1 (26-35(A27L))+melan-A/MART-1 (51-73) (0.1 mg/ml) (for groups 4, 6 and 8) and CD28 (2 µg/ml).

Splenocyte Cytokine and Chemokine Secretion from Immunized Mice:

A membrane-based sandwich immunoassay was performed according to the manufacturer protocol of Proteome Profiler Mouse Cytokine Array Panel A Kit (catalog number: R&D-ARY0068; R&D Systems Inc., Minneapolis, USA). Splenocyte's culture media from each group (Table 1) were pooled (n=6) and concentrated in concentration tubes (Amicon). Each sample was applied on a nitrocellulose membrane containing capture antibodies that bind to specific target protein. After overnight incubation at 4° C., streptavidin-HRP and chemiluminescent reagents were added and incubation steps were performed according to the protocol provided by the analysis kit. Membranes were exposed to X-rays for 10 minutes. Results were detected by a transmission-mode scanner proportionally to the quantity of analyte and determined by protein array analyzer software.

Ex Vivo Immune Cell Killing Assay:

Immune cell cytotoxic activity was assessed using IncuCyte® ZOOM live-cell instrument. RMS cells ($6 \times 10^3$ cells/well) were seeded in 96-well tissue culture plates in complete RMPI without phenol red, on the day before the addition of splenocytes. Pre-stimulated splenocytes were added to RMS cells in a 1:100 ratio. IncuCyte™ Caspase-3/7 Apoptosis Assay Reagent (Cat. No. 4440) was diluted in RPMI without phenol red and added to each well to final concentration of 5 µM. Data was collected every 2 hours for 12 hours. Triton X-100 0.5% (v/v) and cell culture medium were used as positive and negative controls, respectively.

Figure 3A:
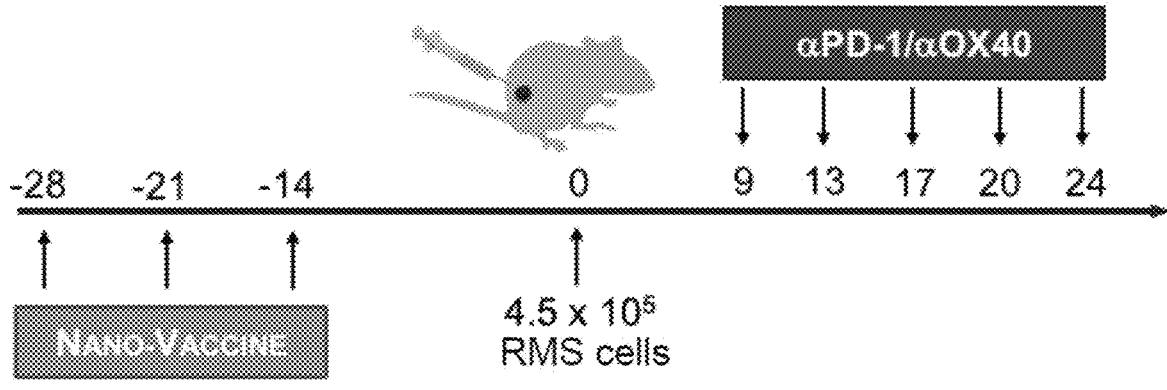
Figure 3B:
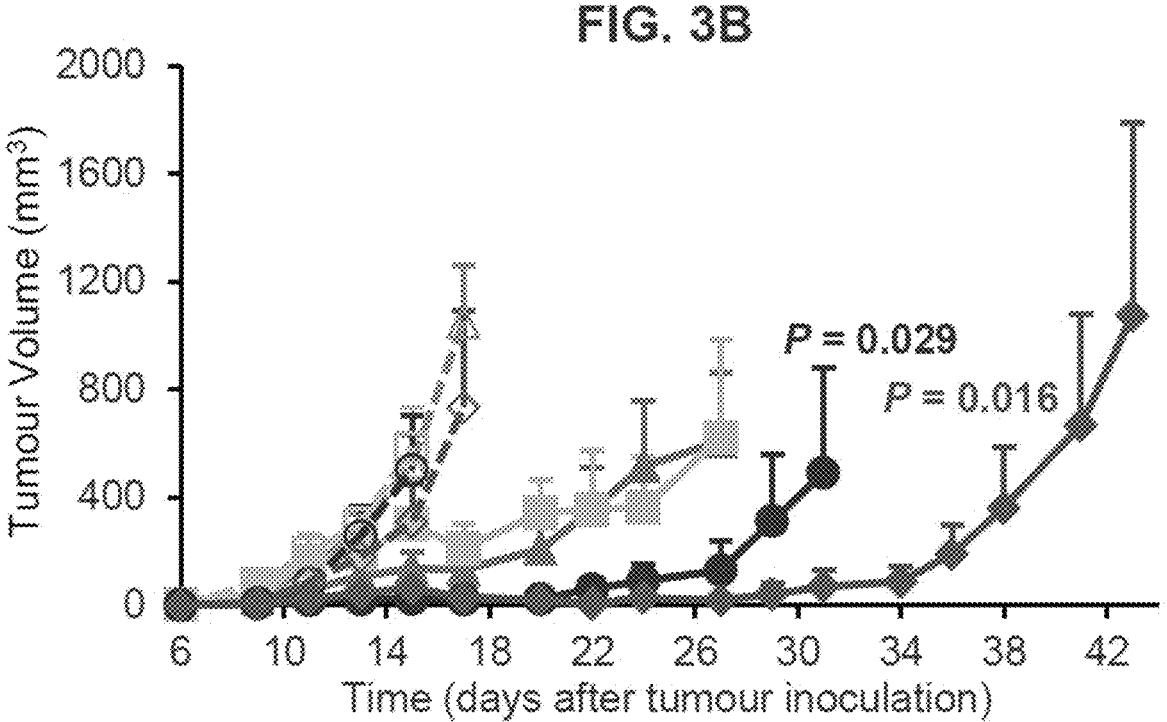

Tumor Inoculation, Combination Therapies, and Tumor Volume Measurements:

Male C57BL/6J mice (8 weeks old) were randomized into different groups (N=4-5) according to Table 2 for the prophylactic combination study. Different schedules were used for the prophylactic (FIG. 3A) and intervention combinatorial studies without or with the addition of ibrutinib (FIG. 4A and FIG. 5A, respectively). For the prophylactic study, on day 0, 50 μl of cell suspension containing $4.5 \times 10^5$ murine RMS cells mixed with growth-factor reduced matrigel (1:1) were inoculated on the right dorsal region as reported before (Schwartz, H. et al. *Cancer Research* 76, 4359-4371, doi: 10.1158/0008-5472.can-16-0485 (2016)). For the intervention studies, the amount of murine RMS and unlabeled Ret melanoma cells that were inoculated on day 0 was $3 \times 10^5$ instead. For intervention study on a second model, 100 μl of saline with $1 \times 10^5$ B16-F10 cells in suspension were inoculated in the right flank. For both models, mice were anesthetized with ketamine (100 mg/kg) and xylazine (12 mg/kg). The right dorsal area was treated with depilatory cream before the injection. αPD-1 and αOX40 were administered intraperitoneally (i.p.) at 10 mg/kg. Ibrutinib was also administered i.p. at 6 mg/kg. Tumor size was measured every 3 days with a caliper. Tumor volume was determined by $X^2$—Y. 0.5 (X—small diameter; Y—large diameter) and body weight was monitored twice a week.

TABLE 2

Prophylactic regimen study design

| Group | Immunization | Immune checkpoint therapy |
|---|---|---|
| 1 | PBS | — |
| 2 | PBS | αPD – 1/αOX40 |
| 3 | MHCI-ag/CpG/MPLA (free) | — |
| 4 | MHCI-ag/CpG/MPLA (free) | αPD – 1/αOX40 |
| 5 | MHCI-ag/MHCII-ag/CpG/MPLA (free) | — |
| 6 | MHCI-ag/MHCII-ag/CpG/MPLA (free) | αPD – 1/αOX40 |
| 7 | NP (empty) | — |
| 8 | NP (empty) | αPD – 1/αOX40 |
| 9 | NP MHCI-ag | — |
| 10 | NP MHCI-ag | αPD – 1/αOX40 |
| 11 | NP MHCI-ag/NP MHCII-ag | — |
| 12 | NP MHCI-ag/NP MHCII-ag | αPD – 1/αOX40 |
| 13 | man-NP (empty) | — |
| 14 | man-NP (empty) | αPD – 1/αOX40 |
| 15 | man-NP MHCI-ag | — |
| 16 | man-NP MHCI-ag | αPD – 1/αOX40 |
| 17 | man-NP MHCI-ag/man-NP MHCII-ag | — |
| 18 | man-NPMHCI-ag/man-NP MHCII-ag | αPD – 1/αOX40 |

Obs.: groups from 3 to 6, 9-12 and 15-18 included the administration of both melanoma-associated peptides (Melan-A/Mart-1MHCI-ag or MHCI-ag/MHCII-ag) and Toll-like receptor ligands (CpG and MPLA).

Immunohistochemistry:

Formalin-fixed paraffin embedded (FFPE) samples of melanoma tumors were sectioned at 5 μm thickness, mounted on positively charged glass slides and dried for 30 minutes at 37° C. After deparaffinization, samples were rehydrated and stained with haematoxylin and eosin (H&E). Immuno-staining was performed with the automated immunohistochemistry (IHC) and in situ hybridization staining system Bond RX (Leica Biosystems, Germany). First, sections were submitted to heat-induced epitope retrieval with Epitope Retrieval solution 1 (ER1, AR9961, Leica Biosystems) for 20 minutes. Hydrogen peroxide 3-4% (v/v) (part of DS9263, Leica Biosystems) was used for 12 minutes to block endogenous peroxidase activity. Sections were then incubated with goat blocking serum (Biological Industries, Israel) for 35 minutes. Afterwards, staining was performed using Intense R Detection system (Leica Biosystems) according to the manufacturer's protocol. Primary antibody incubation time was 1 hour. Tumor sections were stained for apoptotic cells with rabbit anti-cleaved caspase 3 antibody (1:50), for CD4$^+$ T cells with rat anti-mouse CD4 antibody (1:100) and for CD8$^+$ T cells with rat anti-mouse CD8a antibody (1:50). Anti-caspase 3, anti-CD4 and anti-CD8a antibodies were applied in 1% BSA at RT for 1 hour. A broad spectrum biotinylated secondary antibody was added for 1 hour. Slides were then incubated with streptavidin-horseradish peroxidase conjugate for 30 minutes. Staining intensities of cleaved caspase 3, CD4 and CD8a from two tumor sections per treatment group were determined using ImageJ software.

Flow Cytometric Analysis of Tumor-Infiltrated Immune Populations:

Tumors were isolated from the animals directly after euthanasia. Tumor single-cell suspensions were obtained by mechanical disruption of the tissues and enzymatic digestion for 1 hour at 37° C. Enzymatic digestion solution was prepared in RMPI medium with 0.5% BSA, 0.1% collagenase type II (LS004177, Worington), 0.1% dispase (LS02109, Worthington) and DNase (LS002007, Worington). After digestion, the suspension was filtered through a 70 μm filter (BD Biosciences) to remove the debris. The obtained single-cell suspension was then stained with fluorochrome labeled antibodies and analyzed using a LSR Fortessa (BD Biosciences) and FlowJo software (Tree Star Inc.). Intracellular staining was performed with the Inside stain kit (Miltenyi Biotec, Cat. #130-090-477), according to the manufacturer's protocol.

Lymphocyte Panel:

CD3ε-APC (Miltenyi Biotec, Cat. #130-109-240, mouse, clone: REA606—1:10), CD4-FITC (Miltenyi Biotec, Cat. #130-109-419, mouse, clone: REA604—1:10), CD8α-PE (Miltenyi Biotec, Cat. #130-109-247, mouse, clone: REA601—1:10).

Treg Panel:

CD3ε-APC (Miltenyi Biotec, Cat. #130-109-240, mouse, clone: REA606—1:10), CD4-FITC (Miltenyi Biotec, Cat. #130-109-419, mouse, clone: REA604—1:10), CD25-PE (Miltenyi Biotec, Cat. #130-109-051, mouse, clone: REA568—1:10).

Intracellular staining: FoxP3-Vio515 (FITC), (Miltenyi Biotec, Cat. #130-111-681, mouse, clone: REA788, 1:50).

Myeloid Panel:

CD11c-FITC (Miltenyi Biotec, Cat. #130-102-466, mouse, clone: N418—1:10), CD11b-APC-Cy7 (Miltenyi Biotec, Cat. #130-109-288, mouse, clone: REA592—1:10), MHC Class II-Pac. Blue (Miltenyi Biotec, Cat. #130-102-145, mouse, clone: M5/114.15.2—1:10) Gr-1-APC (Miltenyi Biotec Cat. #130-112-307, mouse.

Cytokine Panel:

CD3-PerCP-Cy5.5 (Miltenyi Biotec, Cat. #130-109-841, mouse, clone: REA641—1:10), CD8a-APC-Cy7 (Miltenyi Biotec, Cat. #130-109-328, mouse, clone: REA601—1:10); and intracellular staining of IFN-γ-FITC (Miltenyi Biotec, Cat. #130-109-768, mouse, clone: REA638, 1:10).

Functional Assessment of T-Cells:

For the ELISpot assay, on day 0, 50 μl of cell suspension containing $4.5 \times 10^5$ murine RMS cells were inoculated subdermally. Starting on day 7, mice were treated with two weekly doses as reported in Table 3.

TABLE 3

Elispot study design

| Group | Treatment |
|---|---|
| 1 | PBS |
| 2 | MHCI-ag/MHCII-ag/CpG/MPLA (free) |
| 3 | MHCI-ag/MHCII-ag/CpG/MPLA (free) + αPD −1 /αOX40 + Ibrutinib |
| 4 | NP MHCI-ag/NP MHCII-ag + αPD −1 /αOX40 + Ibrutinib |
| 5 | man-NP MHCI-ag/man-NP MHCII-ag + αPD − 1 /αOX40 + Ibrutinib |

Obs: Groups from 2 to 5 included the administration of both melanoma-associated peptides (Melan-A/MART-1 MHCI-ag or MHCI-ag/MHCII-ag) and the Toll-like receptor ligands (CpG and MPLA).

On day 21, mice were euthanised and spleens harvested and splenocytes isolated. Splenocytes were seeded at $2\times10^5$ cells per well in 96-well plates coated with IFN-γ antibody (R&D Systems Inc.) and incubated for 20 hours with 1 mg/mL of Melan-A/MART-1 MHCI-ag peptide. The secreted and captured IFN-γ was subsequently detected using a biotinylated antibody specific for IFN-γ and an alkaline-phosphatase conjugated to streptavidin. Following the addition of substrate solution, a blue coloured precipitate forms and appears as spots at the sites of cytokine localization. Automated spot quantification was performed using a UV ImmunoSpot® S6 Ultra-V.

For the tetramer staining assay, male C57BL/6J, 8-week-old mice were s.c. immunised into both right and left inguinal area, 2 times, once a week, with 100 μL of man-NP or NP (100 μg of gp100 antigens/20 μg of CpG/20 μg of MPLA per mouse; 50 μL in each side), free gp100 antigens with adjuvants CpG and MPLA, or PBS. Inguinal LN were harvested 10 days after the 2nd injection, homogenized in a single-cell suspension, and plated in 96-well plate for staining. First, the peptide-MHC tetramer tagged with PE (H-2D[b]-restricted EGSRNQDWL (SEQ IIS NO: 7) PE-labelled tetramer (Quimigen S.L., Madrid, Spain)) was added to the single cell suspension, including FcR blocking, following supplier instructions. After 30 min of incubation at 4° C., the cells were washed to remove unbound tetramers, and centrifuged at 1300 rpm, for 10 min, 10° C. Cells were resuspended in ice-cold sorter buffer and plated in 96-well plates. After adding a mix of the antibodies CD3-APC-Cy7 and CD8α-PE-Cy7, cells were incubated for 15 min, at 4° C. protected from light. Cells were washed, centrifuged and resuspended in 200 μl of ice-cold sorter buffer to determine the percentages of tumor antigen-specific CD3[+] CD8α[+] T cells by FACS.

Statistical Methods:

Data are presented as mean±standard deviation (SD) for in vitro assays and as mean±standard error of the mean (SEM) for ex vivo and in vivo assays. Statistical analyses were performed with Student's t-test, one-way and two-way analysis of variance (ANOVA), followed by Bonferroni post hoc test or Tukey test for comparison of multiple groups with IBM SPSS® Statistics (Version 21, Microsoft). Statistical significance in overall survival was determined with log-rank test using SigmaPlot software (Systat Software Inc.) and GraphPad Prism 5® or 7® (GraphPad Software, Inc., La Jolla, CA) P<0.05 was considered statistically significant.

Results

Polymeric Nanoparticles as Anti-Tumor Nano-Vaccines:

The synthesis of mannose-grafted PLGA polymer was confirmed by the multiplet signal between 3.2 and 3.8 ppm in the $^1$H NMR spectra, which indicates the presence of mannose.

NP and man-NP presented a near-neutral surface charge and similar average hydrodynamic diameters (166±5 nm to 181±8 nm), depending on the entrapped molecules, with low polydispersity index (0.13±0.04 to 0.18±0.04) (Table 4). For each formulation, 5 independent batches were prepared (N=5) and measured in triplicate (n=3).

TABLE 4

Particle size, polydispersity index (PdI) and ζ-Potential

| Particles[d] | Size[a] (nm ± SD[b]) | PDI[c] ± SD[b] | ζ-Potential (mV ± SD[b]) |
|---|---|---|---|
| NP (empty) | 168 ± 10 | 0.15 ± 0.05 | −2.17 ± 0.40 |
| NP MHCI-ag | 178 ± 6 | 0.16 ± 0.03 | −3.11 ± 0.50 |
| NP MHCII-ag | 170 ± 5 | 0.18 ± 0.03 | −2.34 ± 0.65 |
| man-NP (empty) | 169 ± 16 | 0.13 ± 0.05 | −2.11 ± 0.40 |
| man-NP MIICI-ag | 181 ± 8 | 0.15 ± 0.04 | −3.02 ± 0.46 |
| man-NP MHCII-ag | 166 ± 5 | 0.18 ± 0.04 | −1.72 ± 0.47 |

[a]Z-average hydrodynamic diameter.
[b]SD, standard deviation, obtained from 5 independent batches (N = 5).
[c]PdI, polydispersity index.
[d]CpG and MPLA were entrapped in all NP and man-NP, with exception of empty nanoparticulate systems.

Electron microscopy and atomic force microscopy showed homogenous spherical particles, with slight roughness on the surface (FIGS. 1B-D). Concanavalin A (Conc A) binds to exposed mannose residues, forming aggregates. After incubation of man-NP, Conc A induced particle aggregation, revealed by a 5-fold increase in average size and confirmed by fluorescence microscopy.

NP and man-NP carried Melan-A/MART-1 (26-35 (A27L)) major histocompatibility complex (MHC) class I (MHCI)-restricted peptide (MHCI-ag) and melan-A/MART-1 (51-73) MHCII-restricted peptide (MHCII-ag), aiming for the class I and class II antigen presentation pathways, respectively. These were shown to potentiate active vaccination strategies, by engagement of both CD4[+] and CD8[+] T cells[18]. NP and man-NP showed high levels of entrapment efficiency (EE) and loading capacity (LC) (Table 5). For the MHCI-ag, EE >97.5±0.2% and LC >48.8±0.1 μg/mg, while for the MHCII-ag EE >74.6±3.5% and LC >37.3±1.7 μg/mg. The EE of CpG was above 80.8±2.5%, corresponding to LC of 8.1±0.3 μg/mg.

TABLE 5

Entrapment Efficiency (EE) and Loading Capacity (LC) of antigens in NP and man-NP

| Particles | EE (% ± SD[a]) | LC (μg/mg ± SD[a]) |
|---|---|---|
| NP MHCI-ag | 99.1 ± 0.1 | 49.6 ± 0.05 |
| NP MHCII-ag | 82.4 ± 0.6 | 41.2 ± 0.3 |
| man-NP MHCI-ag | 97.5 ± 0.2 | 48.8 ± 0.1 |
| man-NP MHCII-ag | 74.6 ± 3.5 | 37.3 ± 1.7 |

[a]SD, standard deviation obtained from 4 independent batches (N = 4).

For each formulation, 4 batches were prepared (N=4) and measurements were made in triplicate (n=3).

NP and man-NP did not affect DC viability (>90%) in the concentration range tested, supporting their physiological biocompatibility. Also, NP and man-NP did not disrupt red blood cell membranes at concentrations up to 20 mg/ml.

Figure 1F:
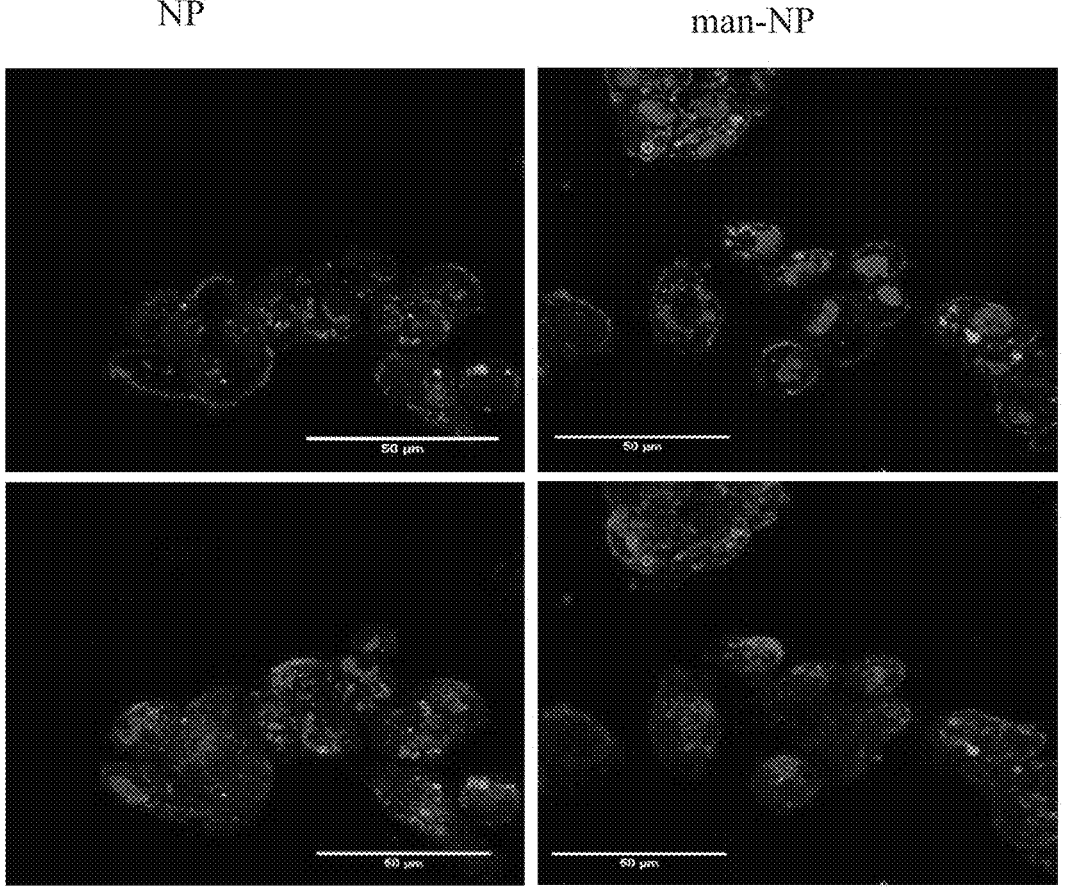

Man-NP exhibited higher internalization levels (P=0.001) on murine immature DC (JAW SII) than non-mannosylated NP (FIG. 1E). Confocal microscopy corroborated these FACS results (FIG. 1F). An increase in Cy5.5-labeled NP and man-NP uptake was observed while using TPGS to prepare these formulations, compared with PVA (FIGS. 7A-C). The higher uptake obtained for mannosylated NP (TPGS) was reduced in the presence of soluble mannose. Therefore, the higher internalisation obtained for mannose-decorated NP was mediated by the interaction of mannose with CD206 receptor at the DC surface.

Figure 1G:
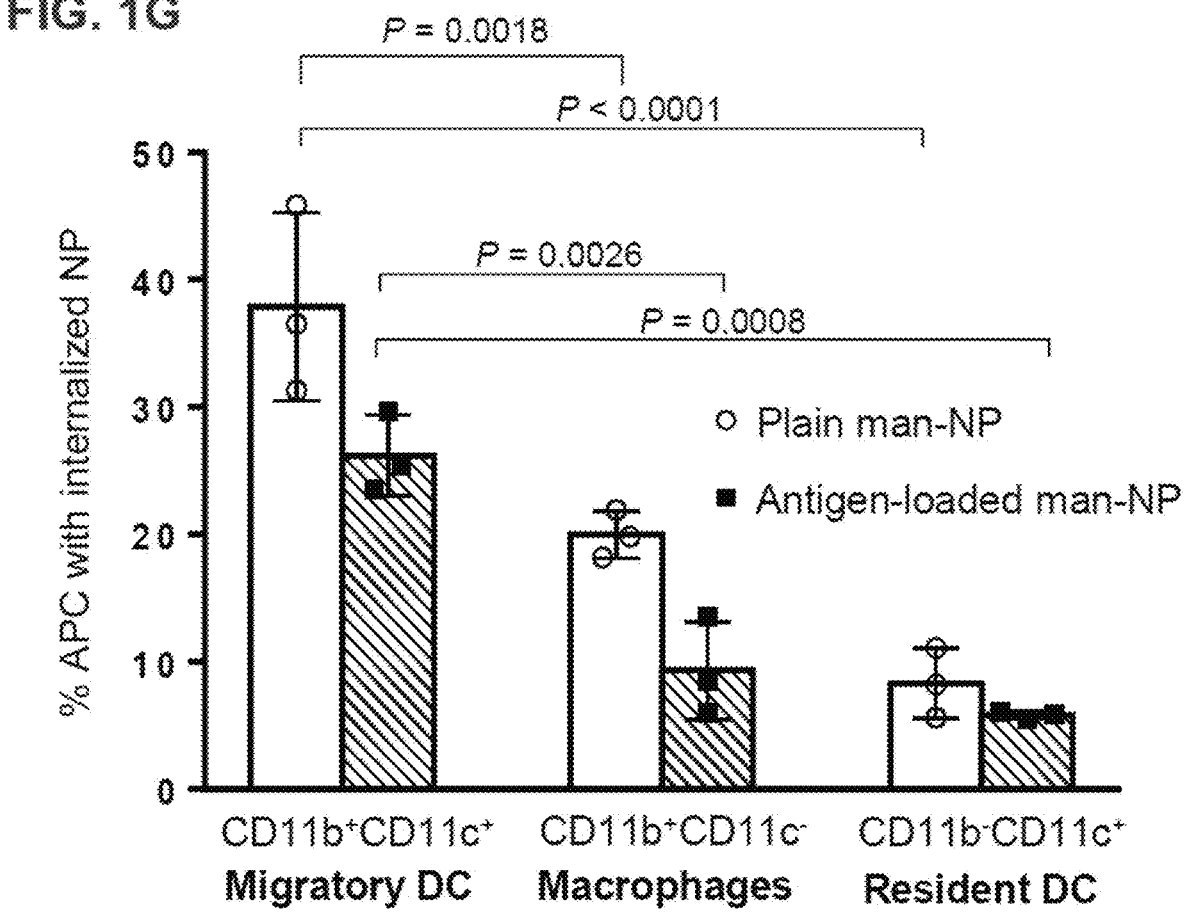
Figure 1H:
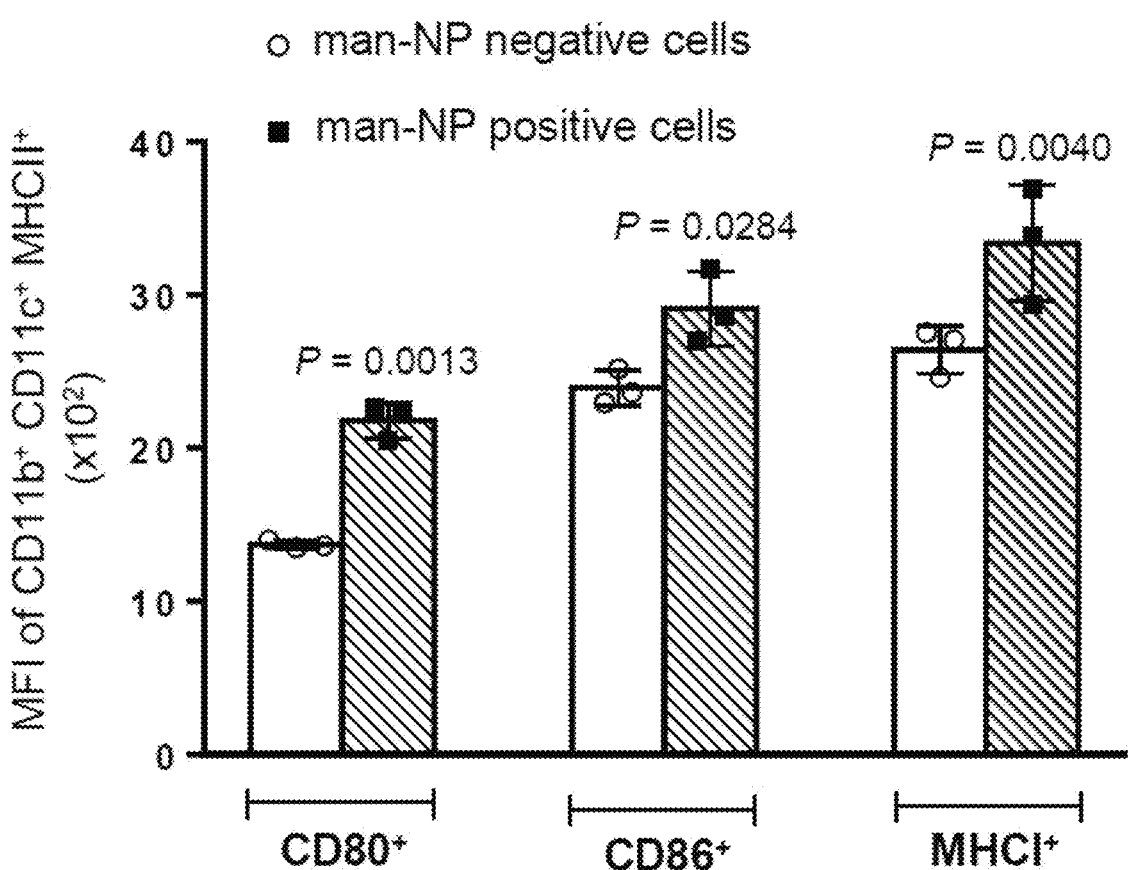

The man-NP (TPGS) were preferentially taken-up in vivo by circulating DC, compared to macrophages and resident DC (FIG. 1G). The nano-vaccine was able to significantly increase the expression of activation/maturation markers at DC surface (FIG. 1H).

Figure 2A:
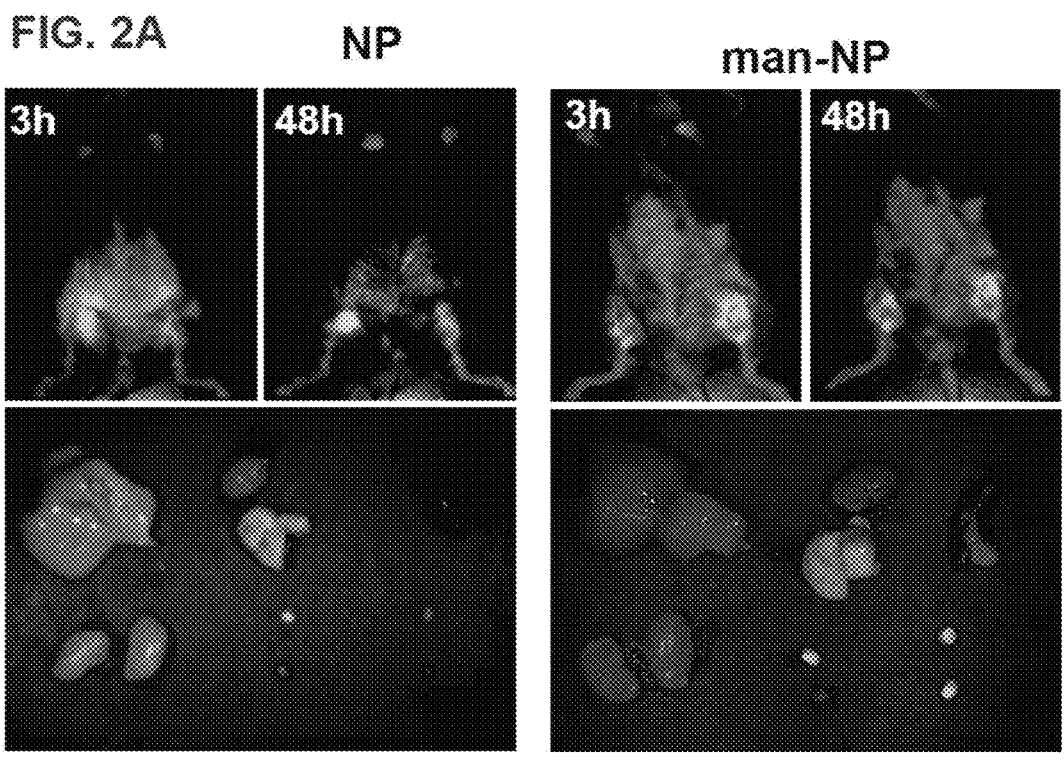
Figure 2B:
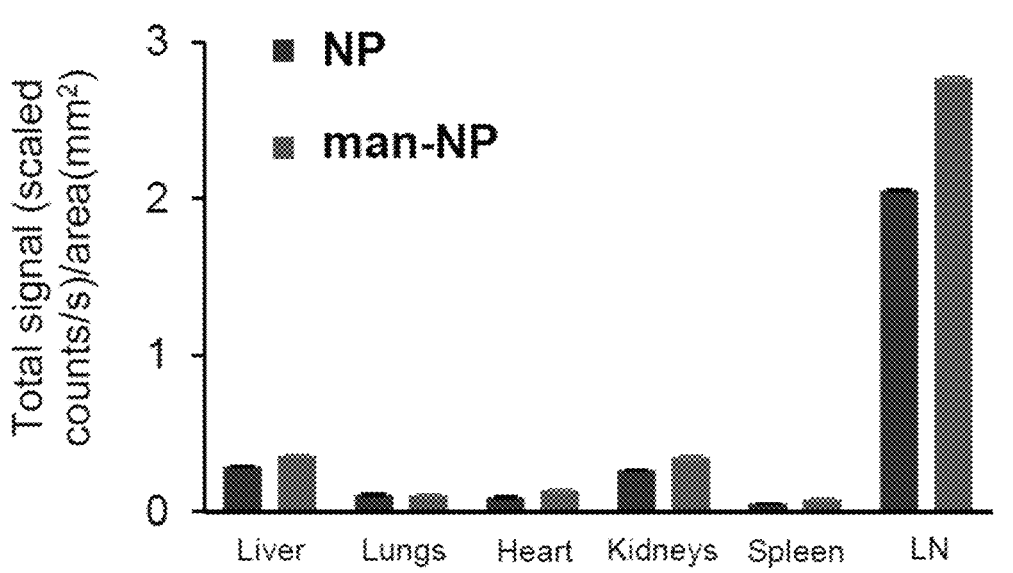

Cytotoxic Activity Induced by Nano-Vaccines:

Cy5.5-labeled NP or man-NP remained at the site of immunisation 48 hours following subcutaneous (s.c.) injection, promoting contact with DC at the periphery (inguinal lymph node (LN)), as well as proximity to the popliteal and axillary LN. This preferential accumulation in LN is important for the induction of antigen-specific adaptive immune responses and vaccine efficacy[20]. Additionally, by presenting a mean average diameter below 200 nm, these nano-vaccines may also be suitable for trafficking through the lymphatic drainage directly to the lymphoid organs[21]. Residual accumulation was detected in the liver and the kidney, due to the excretion of metabolic particle derivatives (FIGS. 2A-B).

Figure 2D:
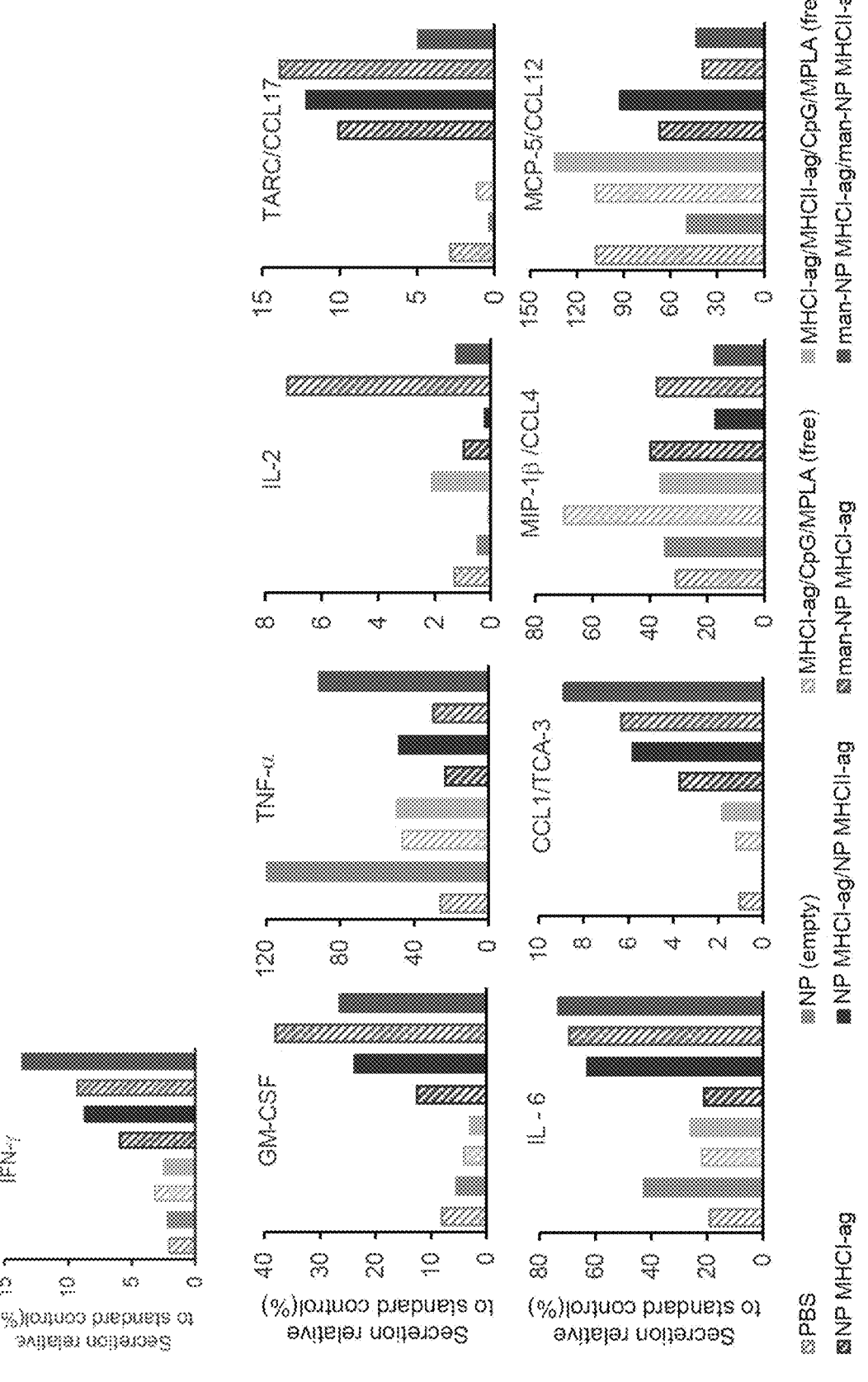

The groups treated with man-NP showed the highest levels of IFN-γ and GM-CSF, which are associated with enhanced antigen priming and subsequent presentation by antigen-presenting cells (APC)[22,23]. IFN-γ is a predictor of antigen-specific cytotoxic CD8+ T-cell (CTL)-mediated responses[24] (FIG. 2D). The nano-vaccines also increased the secretion of IL-6, which is involved in T-cell recruitment and differentiation, and in the suppression of regulatory T (Treg) cells[25,26]. Additionally, the nano-vaccines also led to a lower secretion of the Th2 cytokines MIP-1β/CCL4 and CCL12, which has also been associated with the inhibition of Treg cells, reduction of tumor angiogenesis and enhanced anti-tumor efficacy[27,28].

Figure 2E:
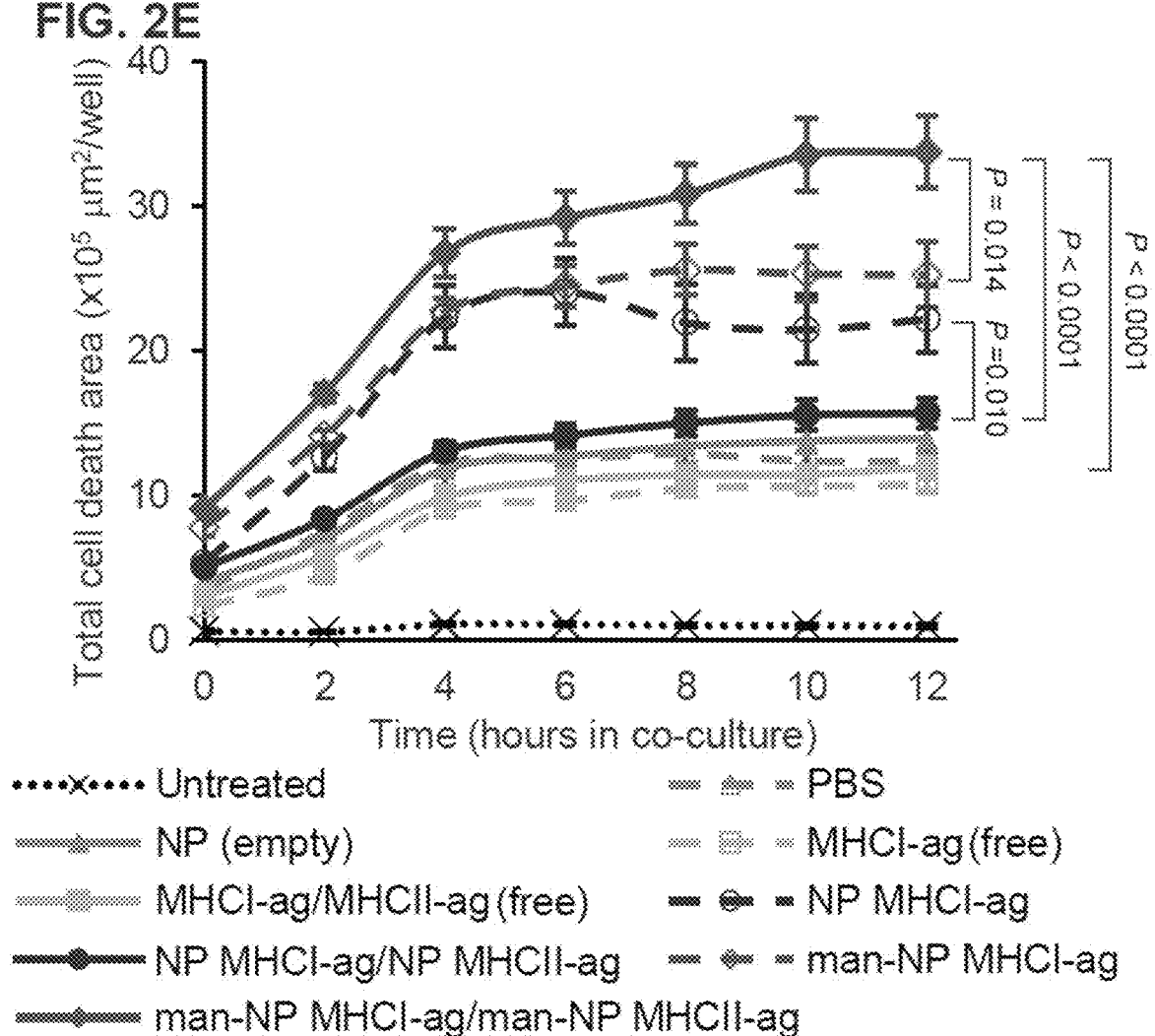

Splenocytes collected from mice immunised with man-NP MHCI-ag/man-NP MHCII-ag exhibited the highest ex vivo cytotoxicity when co-cultured with mCherry-labelled murine Ret melanoma cells (RMS) (FIG. 2E). Man-NP MHCI-ag/man-NP MHCII-ag elicited superior CTL activity compared to man-NP MHCI-ag (P=0.014), to non-mannosylated NP MHCI-ag (P=0.02), and to NP MHCI-ag/NP MHCII-ag (P=9.6×10⁻⁶). MHCI-ag/MHCII-ag/CpG/MPLA (free antigen/immune potentiators) or empty particles induced a CTL activity similar to PBS (FIG. 2E).

The CTL activity induced by man-NP MHCI-ag/man-NP MHCII-ag is clearly shown by the increased fluorescent staining related to caspase 3/7 activation, a marker of apoptosis (FIG. 2F).

The pro-inflammatory cytokine secretion profile induced by the nano-vaccines clearly correlated with this enhanced ex vivo CTL activity. Importantly, the presence of mannose on the surface and the particulate nature of the nano-vaccines co-entrapping the antigens and TLR agonists were crucial for the recognition and destruction of target cells, by activating splenocytes in healthy animals.

There was no evidence of body weight change in all groups, attesting to vaccine tolerability and safety.

Combination of Nano-Vaccines with Immune Checkpoint Modulators:

The combination man-NP MHCI-ag/man-NP MHCII-ag with αPD-1/αOX40 (FIG. 3A) induced a strong and safe tumor growth inhibition (FIGS. 3B-E).

At day 17 after tumor inoculation, the tumor volume in animals treated only with αPD-1/αOX40, or with the combination of non-mannosylated (NP MHCI-ag/NP MHCII-ag) plus αPD-1/αOX40 or mannosylated nano-vaccines (man-NP MHCI-ag/man-NP MHCII-ag) plus αPD-1/αOX40 was much lower compared to animals treated with PBS (P<0.0016) (FIG. 3D). At day 27, the tumor volume intra-group variability increased for all the groups, except for the one treated with man-NP MHCI-ag/man-NP MHCII-ag+αPD-1/αOX40, in which the tumors remained small (FIG. 3E).

Figure 3C:
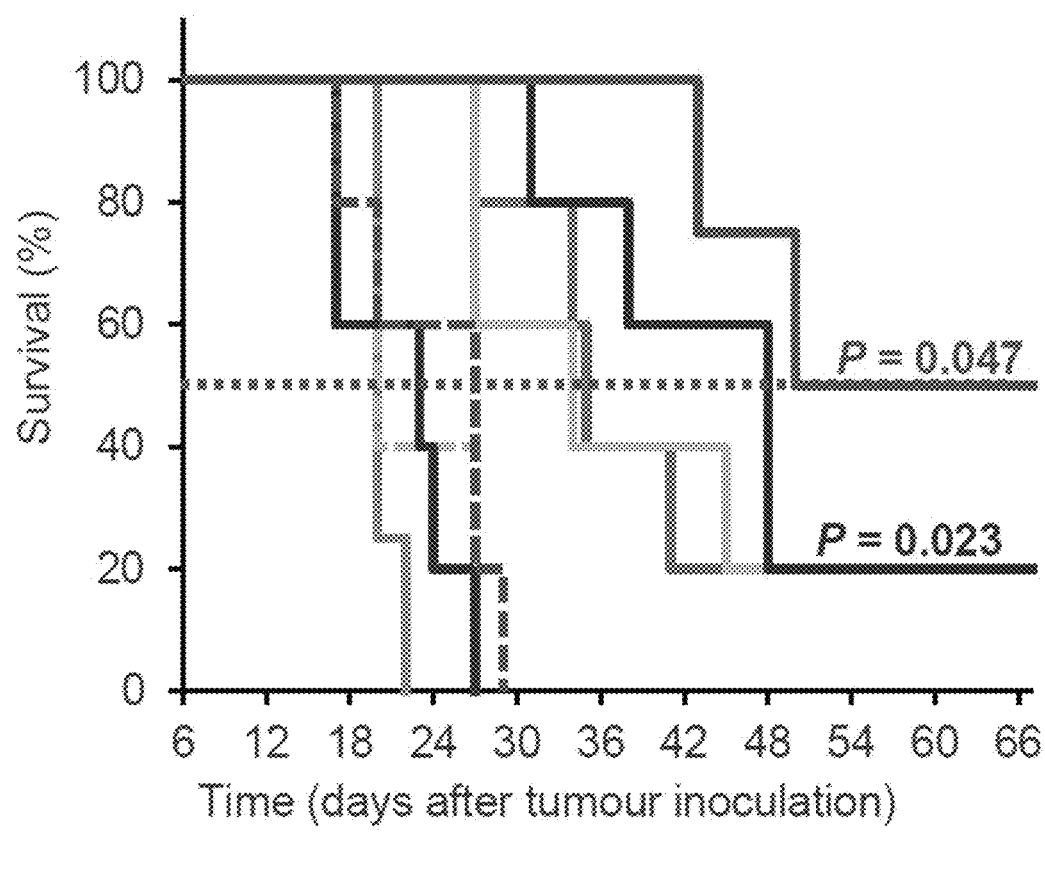

The combination man-NP MHCI-ag/man-NP MHCII-ag+αPD-1/αOX40 resulted in 100% survival 42 days following tumor inoculation, with a survival rate of 50% at day 60. The treatment with αPD-1/αOX40 resulted in only 20% survival (FIG. 3C).

In clinical trials, the use of MHC class II peptides in cancer vaccination has been associated with poor prognosis, due to increased activity of CD4+CD25+ Treg cells or apoptosis of activated CD8+ T cells[29,30]. In the present study, the use of MHCI-ag and MHCII-ag peptides was essential for the induction of a robust anti-tumor response[31], but only when delivered by the present nano-platform, as the free administration of the same antigens induced much lower efficacy. This is an indication that the anti-tumor immune-mediated effect resulted from the epitopes' increased immunogenicity conferred by the adjuvant effect of the nano-vaccine.

Immunohistochemistry staining revealed high levels of caspase-3 and tumor-infiltrating CD4+ and CD8+ T cells in all groups immunised with nano-vaccines.

The highest level of tumor infiltrating-CD8+ T cells was observed in groups treated with mannosylated nano-vaccines, alone or in combination with αPD-1/αOX40, and non-mannosylated nano-vaccines alone. Therefore, the nano-vaccines are capable of reactivating cell-mediated cytotoxicity in the tumor microenvironment (TME), as previously observed ex vivo.

The synergism observed with the combination of prophylactic nano-vaccines with αPD-1/αOX40 prompted the design of a therapeutic intervention strategy in mice inoculated with Ret melanoma cells or RMS cells (FIG. 4A), which induced similar tumor growth profiles.

The groups αPD-1/αOX40 and man-NP MHCI-ag/man-NP MHCII-ag+αPD-1/αOX40 showed similar average tumor volume at day 18, which was 6-fold significantly smaller compared to the PBS-treated group (P<0.0012) (FIG. 4B), with negligible systemic toxicity. The animals treated with the combination had the highest levels of tumor infiltrating-CD8+ T cells (P<0.001) (FIG. 4D), supporting the synergism previously observed in the prophylactic regimen.

The treatment with αPD-1/αOX40 induced the lowest levels of CD4+ T-cell infiltrates (FIG. 4E), displaying reduced infiltration of Treg cells (FIG. 4F). Animals treated with mannosylated nano-vaccines, alone or in combination, had higher levels of Treg cells compared to αPD-1/αOX40-treated group. Therefore, the highest CD8:Treg ratio was observed for αPD-1/αOX40 treatment, followed by the combination of mannosylated nano-vaccines with αPD-1/αOX40 (FIG. 4G).

At the final endpoint, the animals treated with αPD-1/αOX40 remained with the highest CD8:Treg ratio. This was 7-fold higher compared to the groups treated with mannosylated nano-vaccines, alone or in combination with αPD-1/αOX40 ($P<0.01$).

Figure 4D:
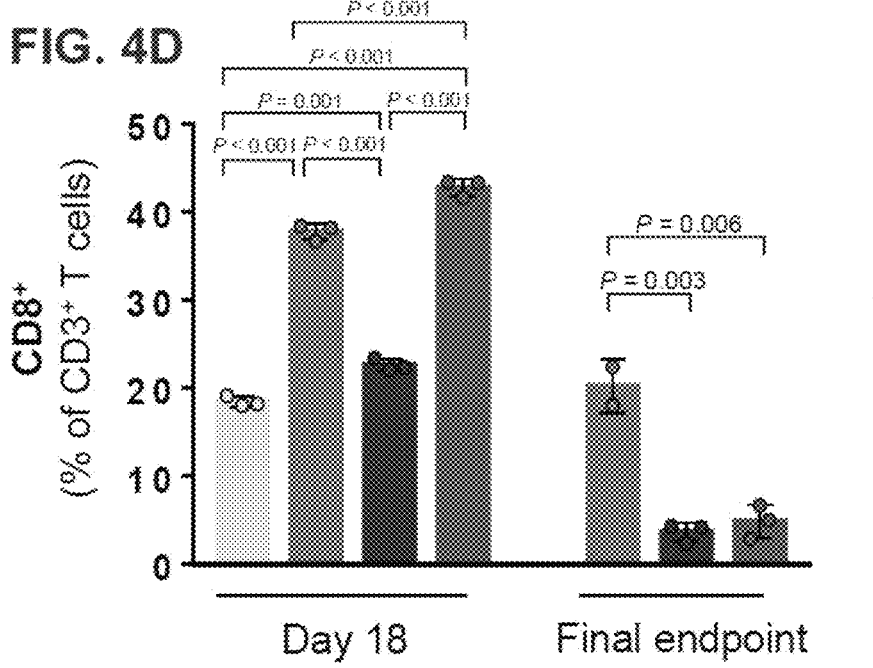
Figure 4E:
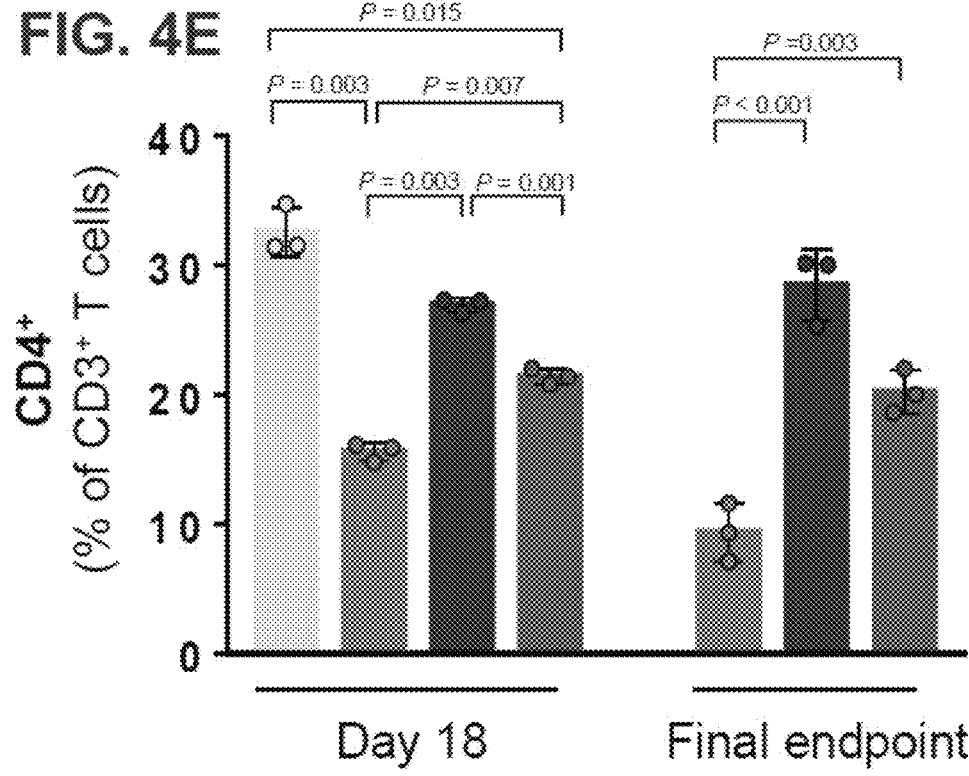
Figures 5A, 5B:
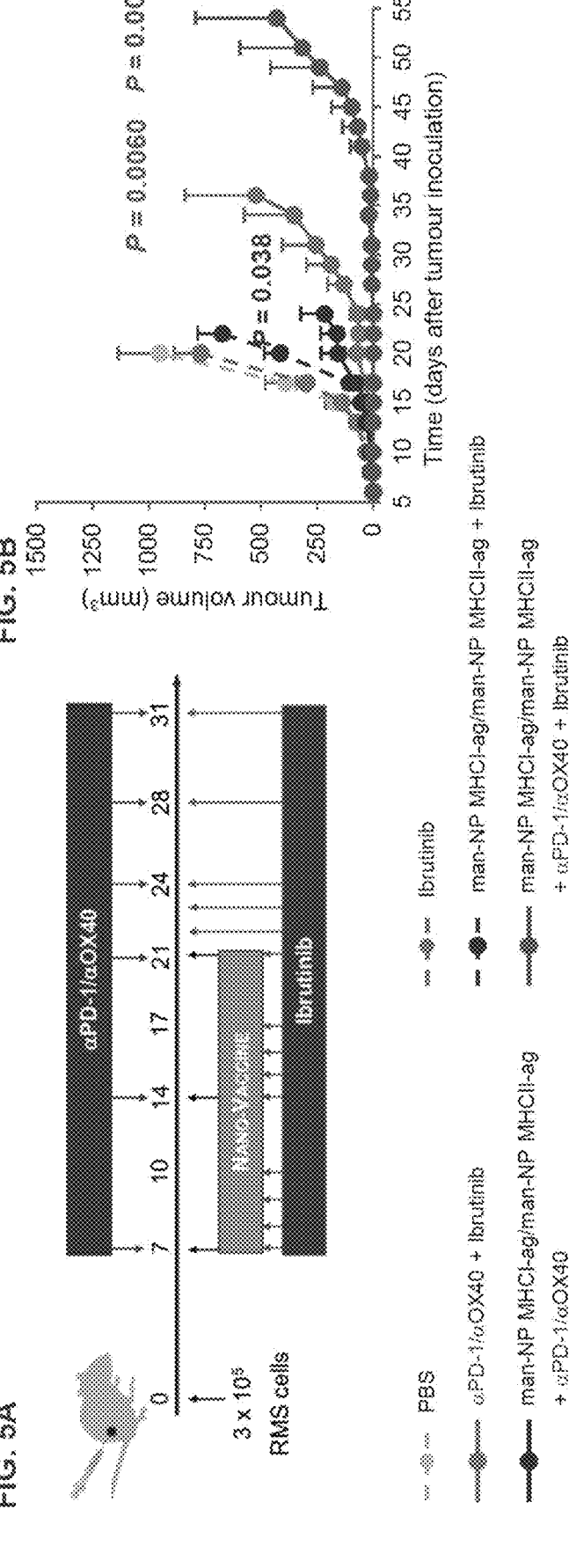
FIGS. 5A-N. Trivalent combination of mannosylated nano-vaccines with ibrutinib and $\alpha$PD-1/$\alpha$OX40 strongly restricts melanoma growth, leading to long-term survival. A, Timeline of tumor inoculation and treatments. B, Tumor growth curve. Data are presented as mean±SEM (N=7 animals). One-way ANOVA. P values correspond to tumor volume at day 20 after tumor inoculation. C, Percent of EGSRNQDWL (SEQ ID NO: 7) (gp100)-specific CD8$^+$ T cells in the lymph nodes. Data presented as mean±SEM. Unpaired, two-tailed t test. D, ELISpot representative images of IFN-$\gamma$ spot forming cells among splenocytes after ex vivo re-stimulation with melan-A/MART-1 peptides on day 22. Each condition was repeated at least 3 times. E, Kaplan-Meier overall survival over time graph, for mice inoculated with $3 \times 10^5$ RMS (N=13 animals for PBS and N=15 animals for the remaining groups), replicated in 2 independent experiments. F, Individual tumor volume at days 27, 36 and 43 after tumor inoculation, with mean±SEM represented (N=13 animals for PBS and N=15 animals for the remaining groups), replicated in 3 independent experiments. G-N, Tumor-infiltrating immune cell populations, Tumors were isolated on the first endpoint, day 20 after tumor cell inoculation that corresponds to the day of the first death in the PBS-treated group, whereas the second endpoint was tumor size-matched: day 27 for PBS, ibrutinib only and mannosylated nano-vaccines+ibrutinib; day 35 for $\alpha$PD-1/$\alpha$OX40+ibrutinib and mannosylated nano-vaccines+$\alpha$PD-1/$\alpha$OX40. Quantification was performed by flow cytometry. During this period, the tumors of animals treated with mannosylated nano-vaccines+$\alpha$PD-1/$\alpha$OX40+ibrutinib were very small and therefore, those were kept for the immunohistochemistry analysis. Data are presented as mean±SD, N≥3 animals. Unpaired, two-tailed t test.

Interestingly, from day 18 to the final endpoint, the infiltration of $CD11b^+Gr-1^+$ Myeloid-derived Suppressor Cells (MDSC) increased significantly in the two groups treated with mannosylated nano-vaccines, alone or in combination (FIG. 4H). At the final endpoint, the levels of MDSC in those groups were approximately 4-fold higher than those obtained for the αPD-1/αOX40-treated group. These extremely elevated levels of MDSC seem to correlate with the marked decrease of $CD8^+$ T-cell infiltration (FIG. 4D) and with the high percentage of Treg cells (FIG. 4F) at the final endpoint.

The infiltration of MDSC hindered the early effect of $CD8^+$ T-cell stimulation and proliferation, inhibiting T-cell infiltration and CTL activity[32,33]. This imbalance promoted an immunosuppressive TME, and the combination of mannosylated nano-vaccines+αPD-1/αOX40 failed to show benefit in comparison with αPD-1/αOX40 alone.

Ibrutinib was shown to limit the generation and migration of MDSC, and was proposed as a strategy to enhance cancer immunotherapeutic strategies[15,34]. It was hypothesized that the inhibition of these MDSC with ibrutinib could improve the clinical outcomes of our strategy.

Combination of Nano-Vaccines with Immune Checkpoint Modulators and an MDSC-Inhibitor:

Melanoma-bearing mice were treated according to the schedule in FIG. 5A. On day 20 after tumor inoculation, the average tumor volume of groups treated with ibrutinib or with mannosylated nano-vaccines+ibrutinib were identical to the PBS-treated group. However, groups treated with the trivalent therapy (mannosylated nano-vaccines+αPD-1/αOX40 or αPD-1/αOX40+ibrutinib) showed a significantly reduced tumor volume by more than 5-folds ($P=0.038$ and $P=0.0060$, respectively) (FIG. 5B). Importantly, there was no difference between this anti-tumor response induced by the triple combination therapy in animals inoculated with Ret melanoma cells or RMS.

Figures 8A, 8B:
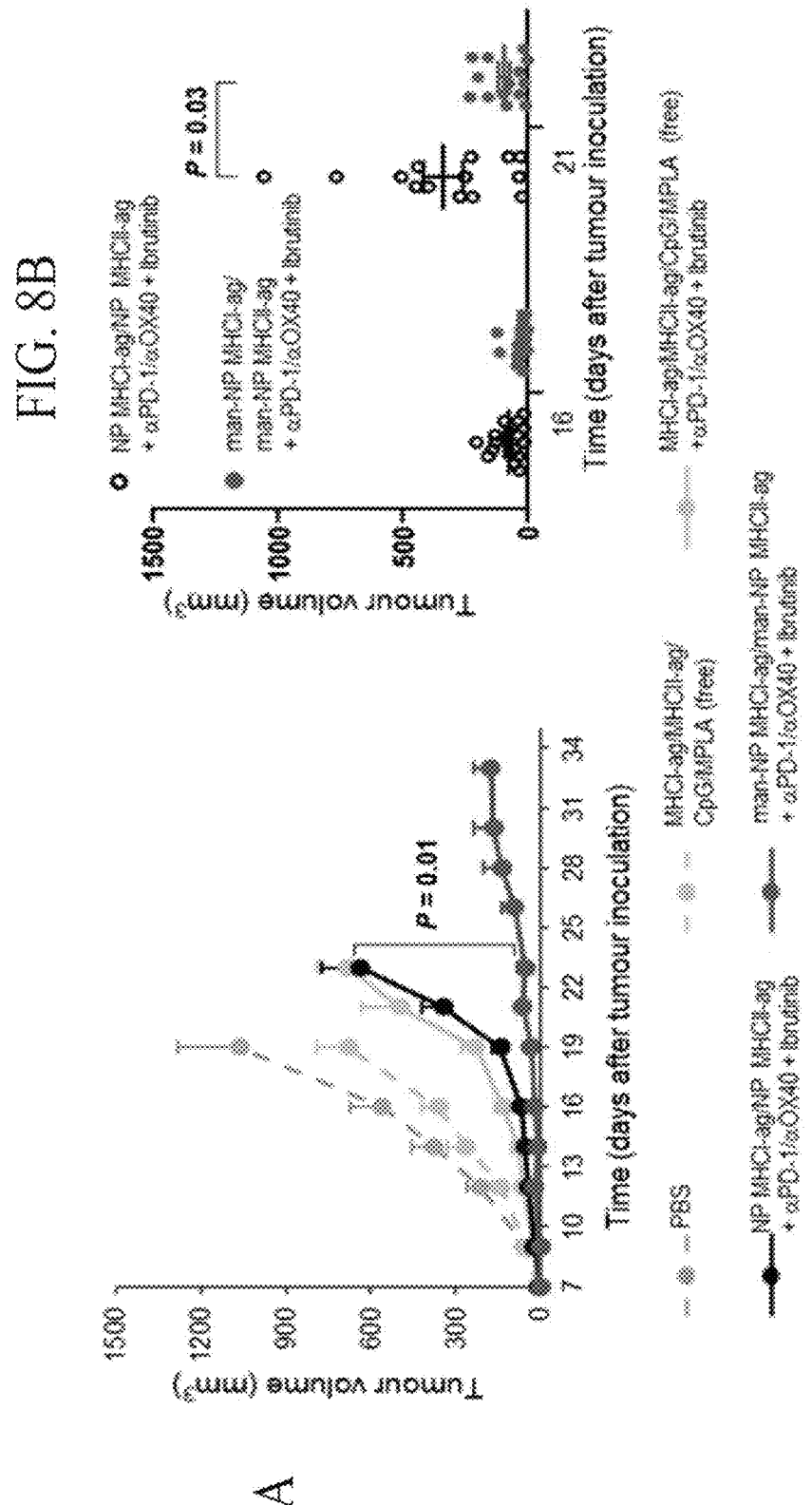
FIGS. 8A-Q. Trivalent combination of mannosylated and non-mannosylated nano-vaccines with ibrutinib and $\alpha$PD-1/$\alpha$OX40. A, Tumor growth curve. Data are presented as mean±SEM (N=13 animals for PBS group and N=15 animals the remaining groups). P values correspond to tumor volume at day 23 after tumor inoculation. 13, Individual tumor volume at days 16 and 21 after tumor inoculation, with mean±SEM (N=13 animals for PBS group and N=15 animals the remaining groups) represented. One-way ANOVA. C, Representative scatter plots on day 24. The experiment was repeated at least 3 times with similar results. D, Frequency of EGSRNQDWL (SEQ ID NO: 7)-specific CD8$^+$ T cells in the lymph nodes. Data presented as mean±SD (N=3 animals). One-way ANOVA. E, ELISpot analysis of IFN-$\gamma$ spot forming cells among splenocytes after ex vivo re-stimulation with melan-A/MART-1 peptides on day 22. Each condition was repeated at least 3 times. F, Frequency of IFN-$\gamma^+$CD8$^+$ CTL tumor single-cell suspension gated for CD3e, CD8a and IFN-$\gamma$. Data are presented as mean±SD (N=3 animals). One-way ANOVA. G. Kaplan-Meier overall "survival" after 1000 mm$^3$ over time graph, for mice inoculated with $3 \times 10^5$ RMS. All data are presented as mean of at least 3 independent replicates. Mean±SD; N=13 animals for PBS group and N=15 animals for the remaining groups. Log-rank test.

In addition, man-NP were significantly superior to the non-mannosylated nano-vaccines from day 19 onwards ($P=0.005$), demonstrating the crucial role of the mannose targeting moieties for achieving an effective immune-mediated control of tumor growth (FIGS. 8A-B). In fact, on day 23, the man-NP-treated group had an average tumor volume of 54 mm$^3$, in contrast to the NP-treated group, which had an average tumor volume of 638 mm$^3$.

Figures 5C, 5D:
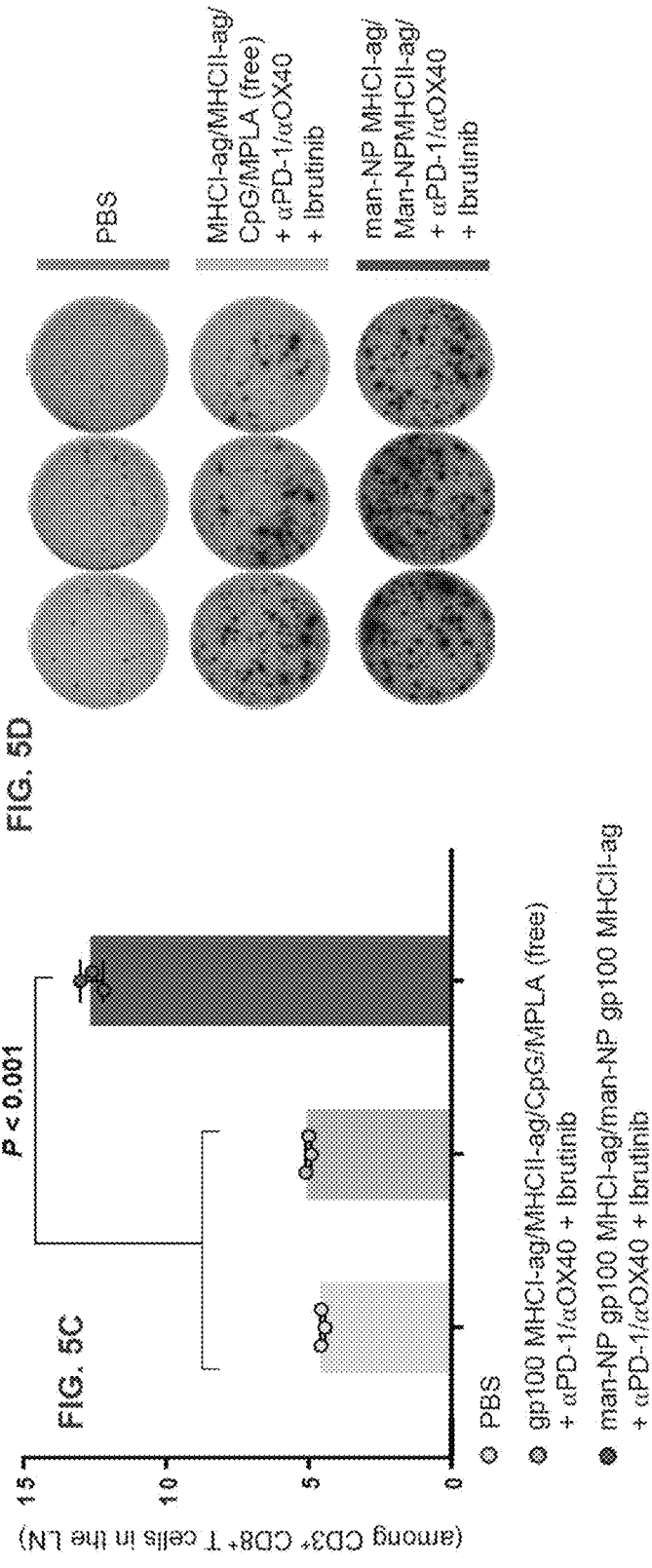
Figure 8C:
Figure 8F:
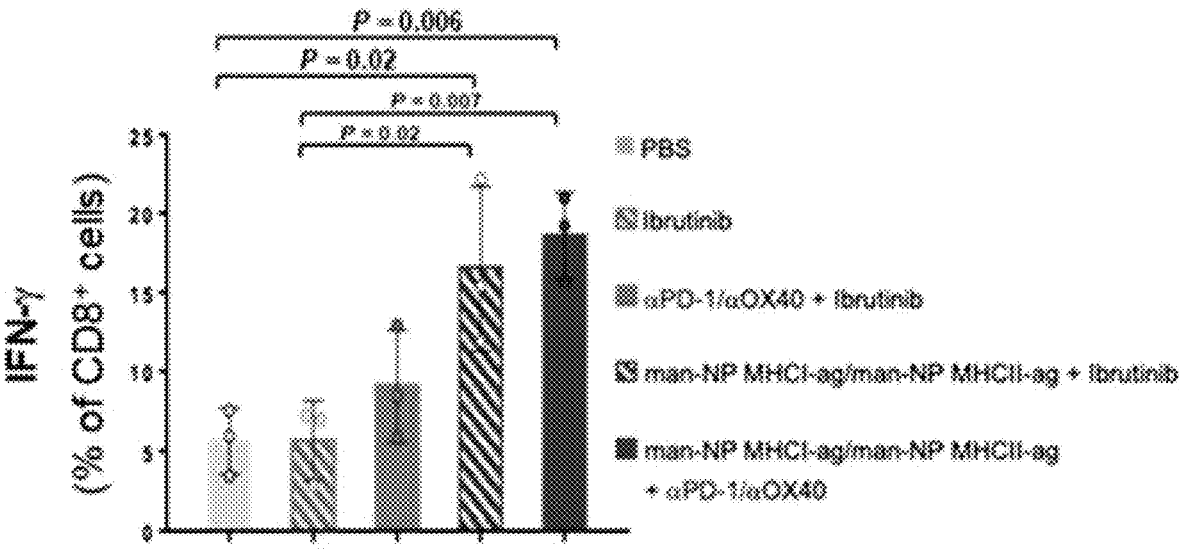

The trivalent therapy including the mannosylated nano-vaccines induced the most potent antigen-specific anti-tumor immune response ($P=0.001$) (FIGS. 5C-D, FIGS. 8C-D). The superior antigen-dependent immune response was irrespective of the antigen used (gp100 or melan-A/MART-1), as shown by a tetramer staining assay (FIG. 5C, 8C-D). Melan-A/MART-1 specificity was further confirmed by the IFN-γ ELISpot assay (FIG. 8E). RMS-bearing mice treated with mannosylated nano-vaccines presented the highest levels of antigen-specific intracellular IFN-γ+stained in tumor-infiltrating cytotoxic $CD8^+$ T lymphocytes, at the 1$^{st}$ endpoint (FIG. 8F).

Figure 8G:
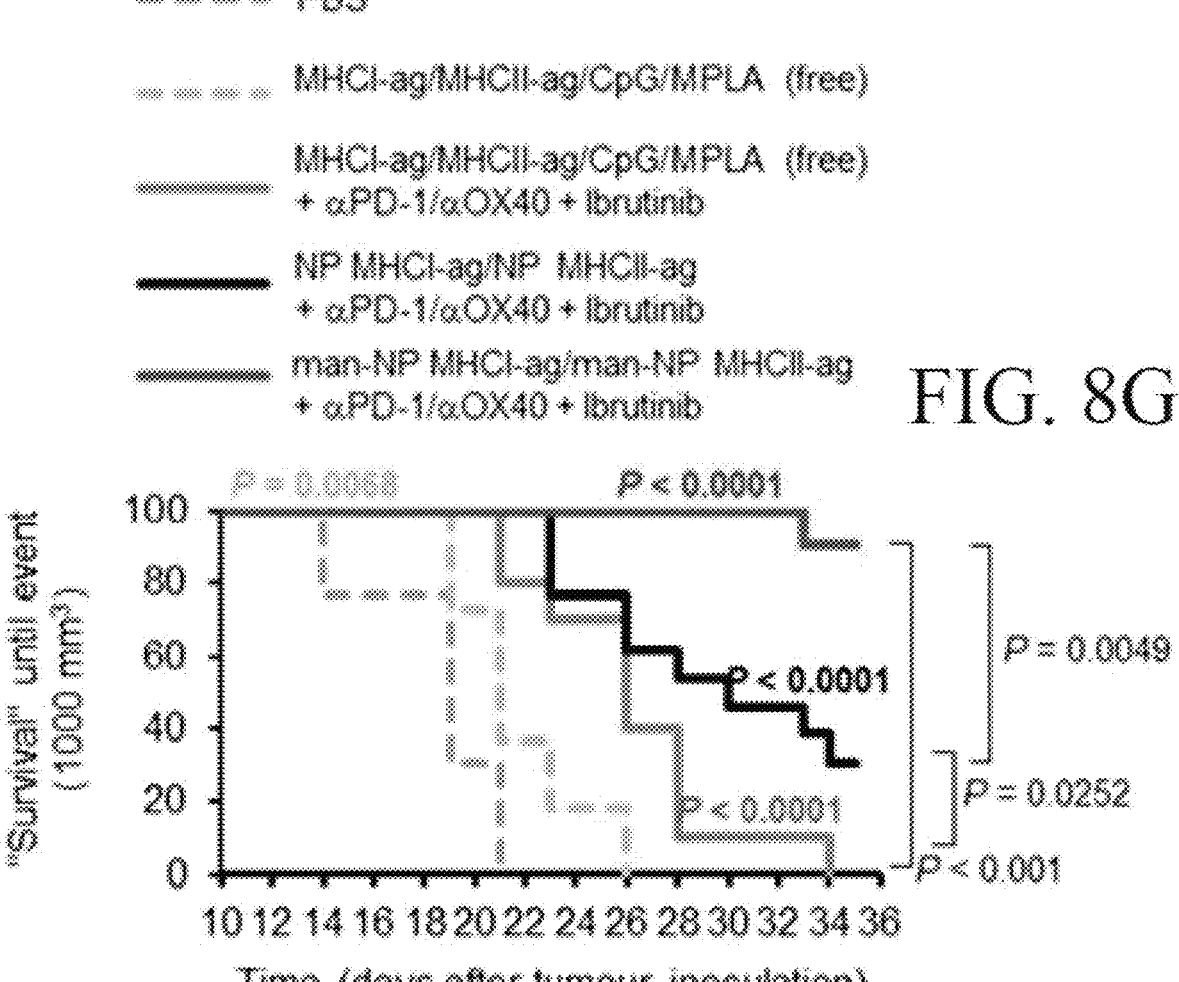

On day 33, animals treated with the man-NP MHCI-ag/man-NP MHCII-ag+αPD-1/αOX40+ibrutinib presented a 3-fold higher survival percentage ($P=0.0049$) compared to animals treated with NP MHCI-ag/NP MHCII-ag+αPD-1/αOX40+ibrutinib, among which 8 out of 13 already reached a tumor volume of at least 1000 mm$^3$ (FIG. 8G).

Figure 5E:
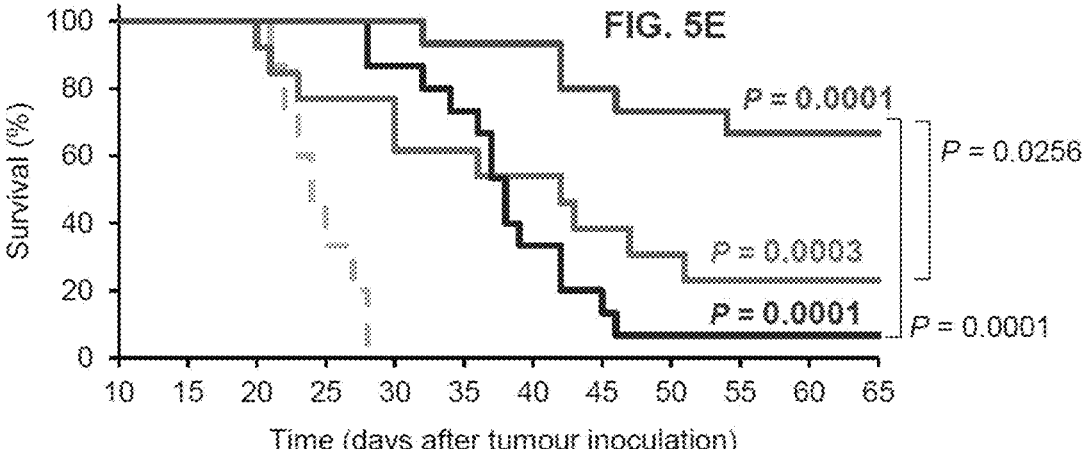
Figure 5F:
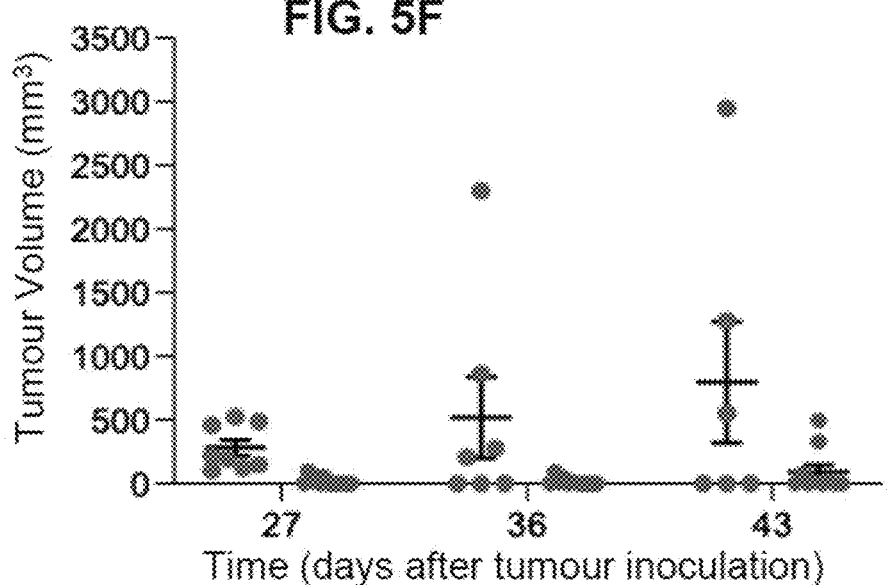

Fourteen out of 15 animals of the group mannosylated nano-vaccine+αPD-1/αOX-40+ibrutinib remained alive at day 40, in comparison to 7 out of 15 animals of the group αPD-1/αOX-40+ibrutinib (FIG. 5E). The latter presented higher variability in terms of tumor size (FIG. 5F). Moreover, 7% of the animals treated with mannosylated nano-vaccine+αPD-1/αOX-40 and 23% of the animals treated with αPD-1/αOX-40+ibrutinib remained alive after 65 days, while 67% of animals treated with the trivalent combination mannosylated nano-vaccine+αPD-1/αOX-40+ibrutinib survived during that period. The survival curves of the triple regimen are statistically different from those obtained for PBS ($P=0.0001$), man-NP+αPD-1/αOX-40 ($P=0.0001$) and αPD-1/αOX-40+ibrutinib ($P=0.0256$) treatments. Only slight body weight changes relative to the initial body weight were detected throughout the study, reflecting negligible systemic toxicity.

Figures 5G, 5H:
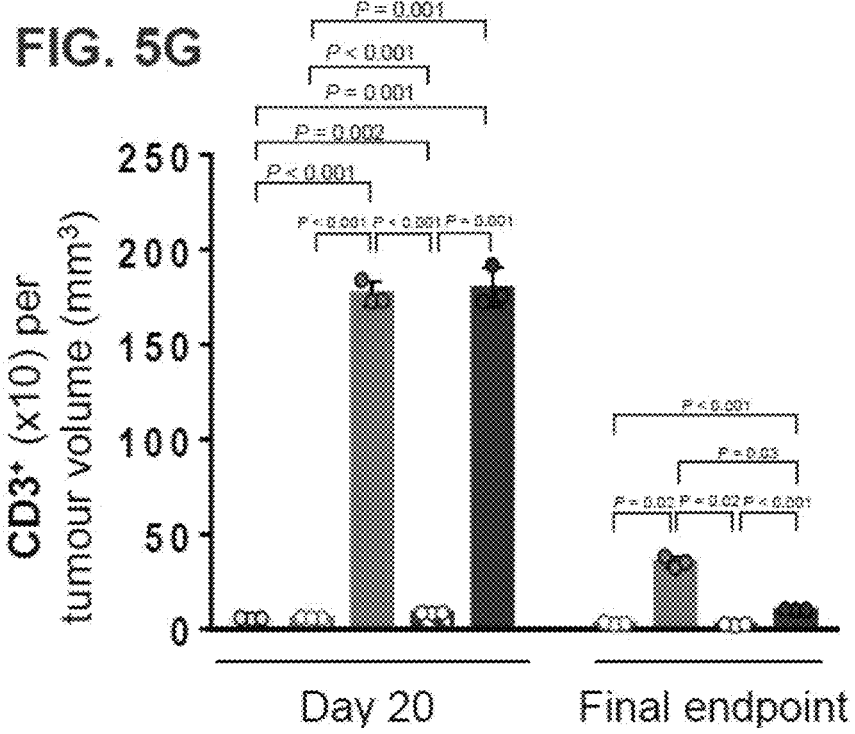

Higher infiltration of T lymphocytes, as expected, was associated with stronger tumor growth inhibition (FIG. 5G). The number of $CD8^+$ T lymphocytes was more than 20-fold higher for mice treated with αPD-1/αOX40+ibrutinib or with mannosylated nano-vaccines+αPD-1/αOX40, compared to the PBS-treated group (FIG. 5H).

Figure 5I:
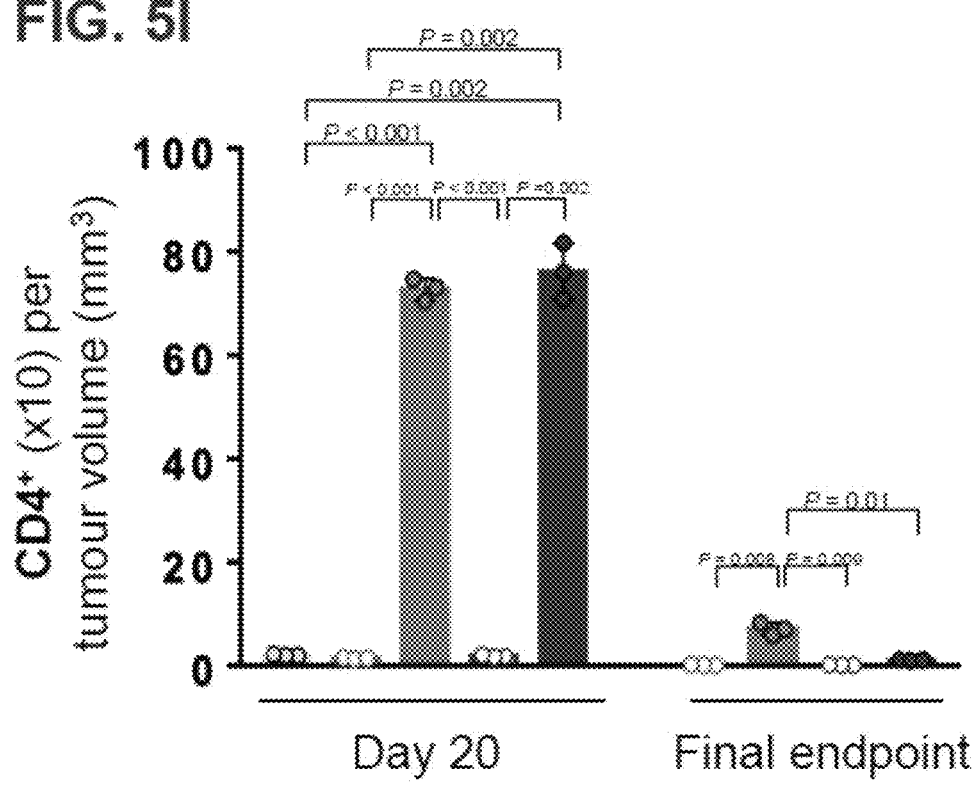

The highest level of $CD8^+$ TIL, at the second endpoint, was induced by αPD-1/αOX40+ibrutinib. At this time point, low levels of Treg cells were observed within the tumors of animals treated with αPD-1/αOX40+ibrutinib or mannosylated nano-vaccines+αPD-1/αOX40 (FIGS. 5I-J). Both treatments also resulted in high CD8:Treg ratios, which correlated with the enhanced therapeutic efficacy (FIG. 5K).

The prominent infiltration of $CD8^+$ T cells at day 20 after tumor inoculation, in groups that received the mannosylated nano-vaccines with αPD-1/αOX40 was further confirmed by immunohistochemistry staining of RMS tumor sections for CD4 and CD8. The mannosylated nano-vaccines also induced higher expression of the OX40 receptor, as shown in the groups treated with man-NP MHCI-ag/man-NP MHCII-ag+ibrutinib and man-NP MHCI-ag/man-NP MHCII-ag+αPD-1/αOX40. The co-stimulatory OX40 was then available at higher extent to be targeted by the immune checkpoint therapy.

It should be noted that the expression of PD-1/PD-L1 was the lowest for the tumors of animals treated with man-NP MHCI-ag/man-NP MHCII-ag+αPD-1/αOX40+ibrutinib, even compared to those immunised with the non-mannosylated NP.

High levels of caspase-3 were observed in the tumors of the groups that received man-NP MHCI-ag/man-NP MHCII-ag+ibrutinib, man-NP MHCI-ag/man-NP MHCII-ag+αPD-1/αOX40 and αPD-1/αOX40+ibrutinib, although only man-NP MHCI-ag/man-NP MHCII-ag+αPD-1/αOX40 and αPD-1/αOX40+ibrutinib strongly inhibited tumor growth and significantly prolonged survival of the mice (FIGS. 5B, E).

Figure 5L:
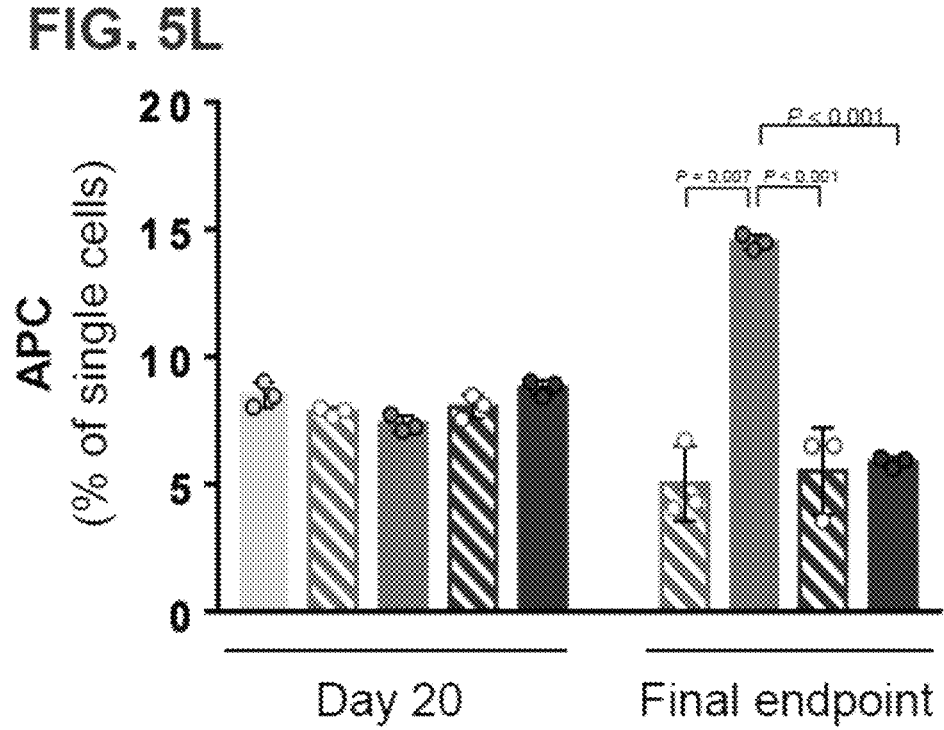
Figure 5M:
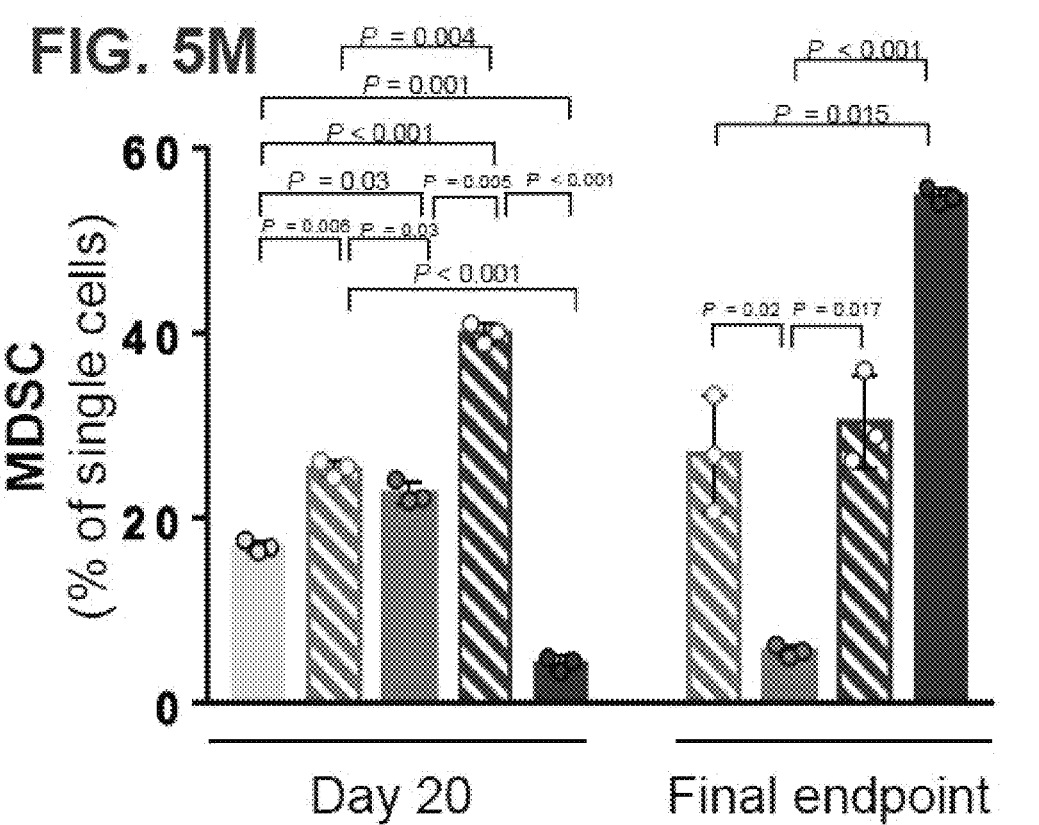
Figure 5N:
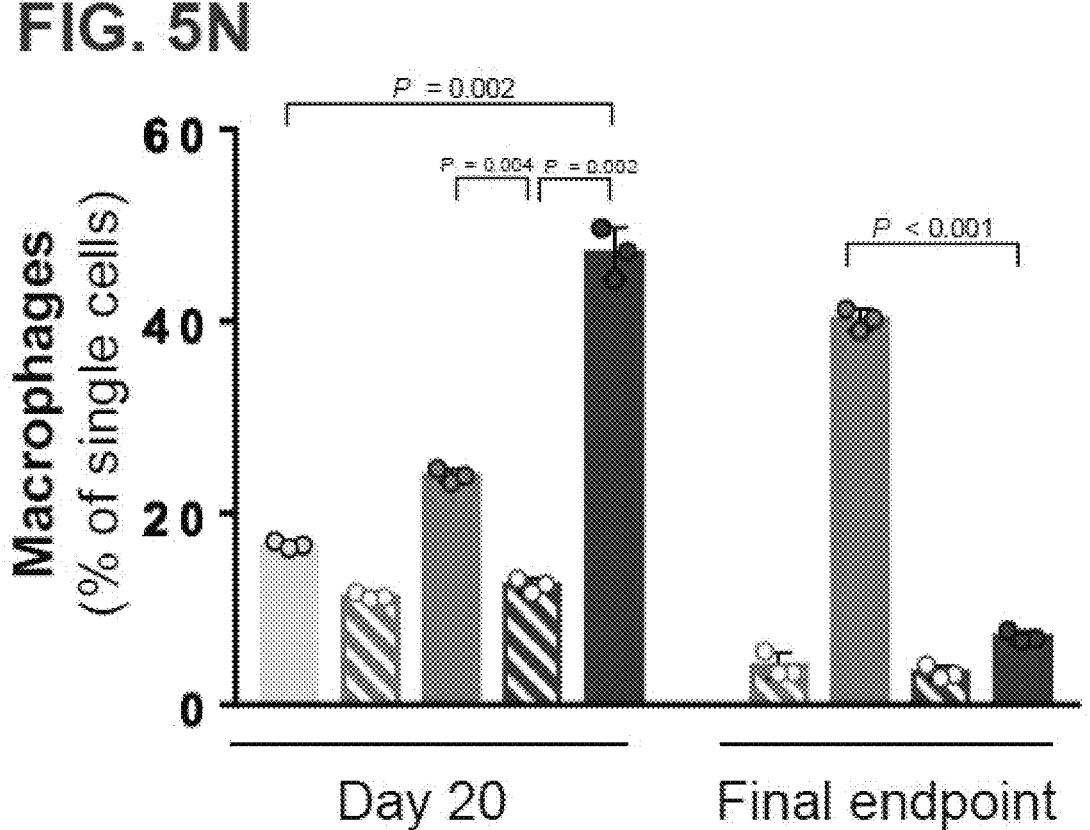
Figure 6:
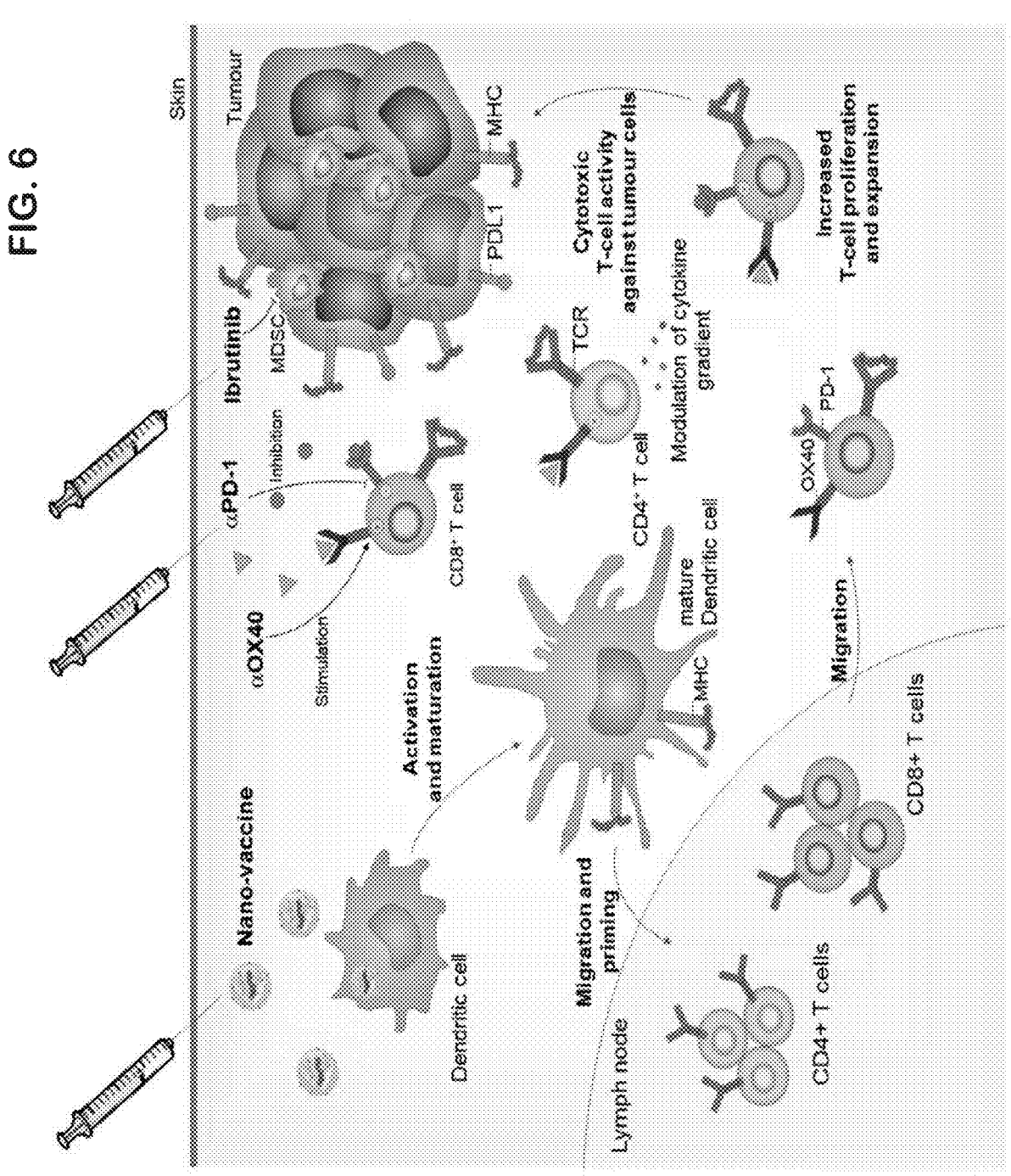
FIG. 6. Proposed model for the trivalent therapeutic strategy combining mannosylated nano-vaccines with ibrutinib and $\alpha$PD-1/$\alpha$OX40.

In groups treated with αPD-1/αOX40+ibrutinib, and mannosylated nano-vaccines+ibrutinib, a decrease in MDSC infiltrates was observed from the first to the second endpoint. This suggests that ibrutinib was restricting the migration of MDSC into the TME (FIG. 5M). No clear effect was observed on tumor-infiltrating APC and macrophages (FIG. 5L, N).

The trivalent combination showed superior anti-tumor efficacy also in two independent studies using a second mouse model bearing orthotopic s.c. B16-F10 melanoma

53

Figure 9C:
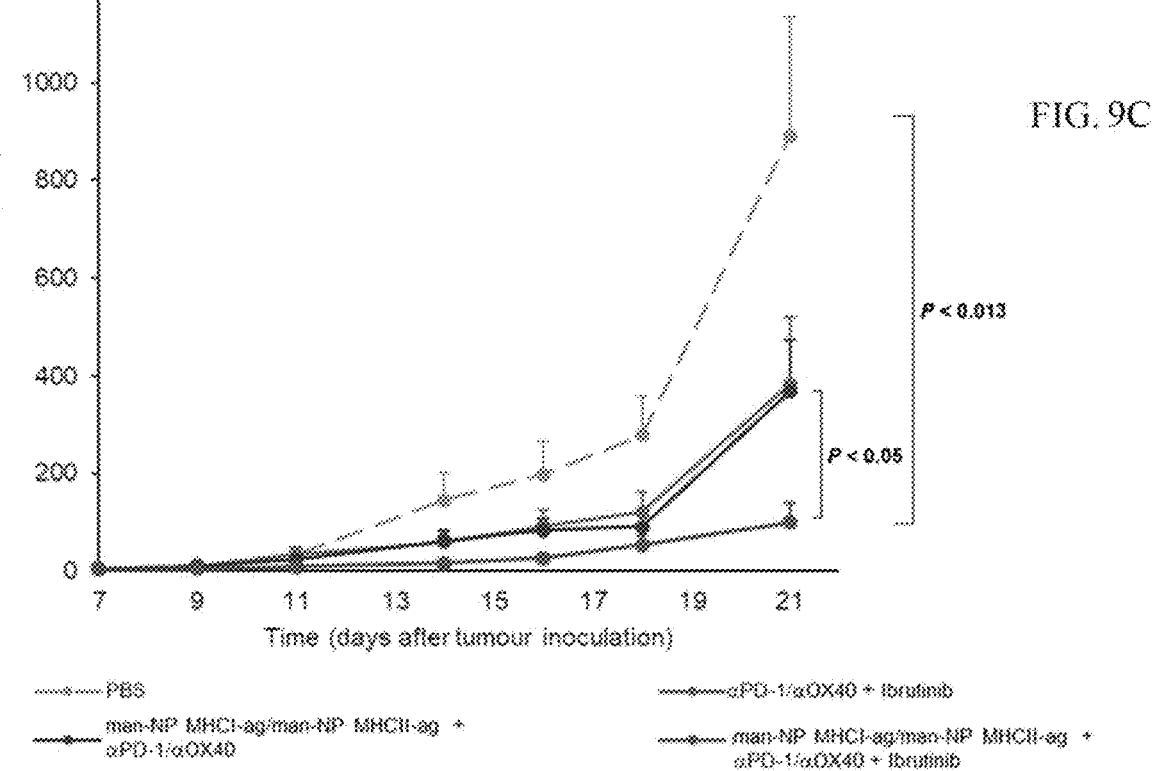
Figure 10A:
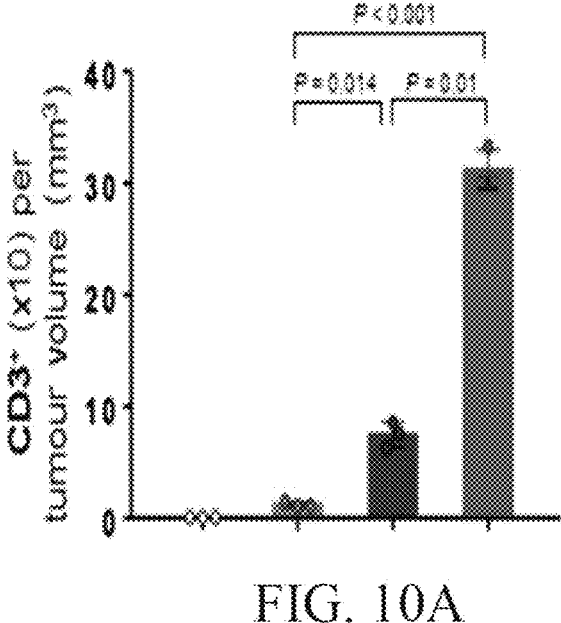
FIGS. 10A-H. High infiltration of T lymphocytes and inhibition of MDSC are associated with improved therapeutic efficacy in B16-F10 model. A-H. Tumor-infiltrating immune cell populations. Tumors were isolated on the first endpoint, day 22 after tumor cell inoculation. Quantification was performed by flow cytometry (FACS). Data are presented as mean±SD (N=3 animals). Unpaired, two-tailed t test.
Figure 10B:
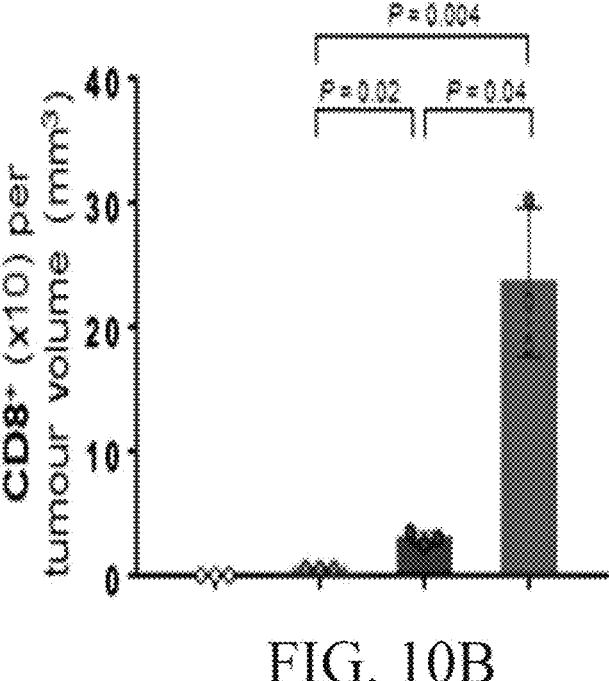
Figure 10C:
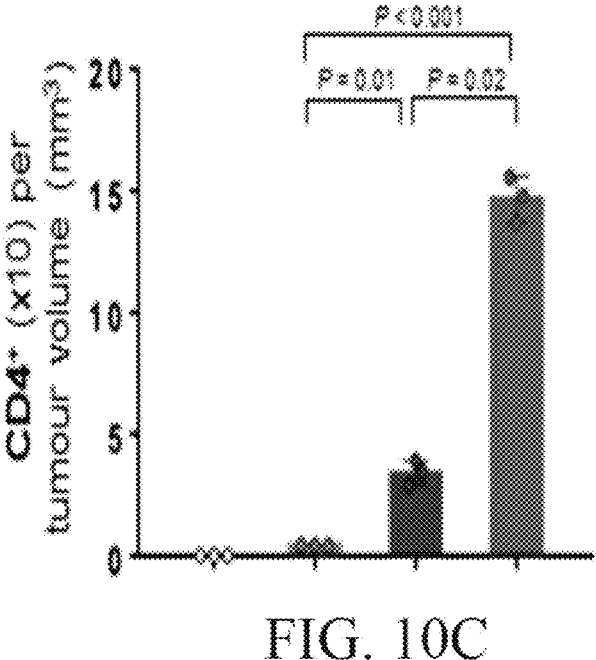
Figure 10D:
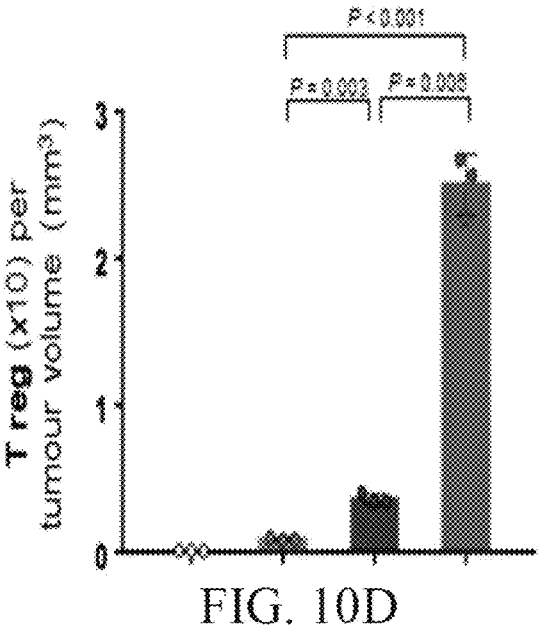
Figure 10E:
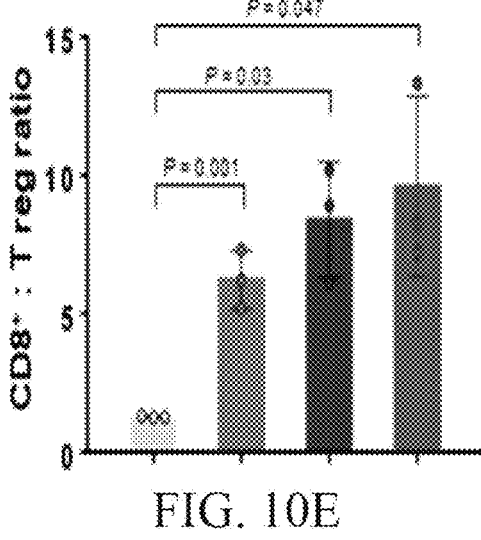
Figure 10F:
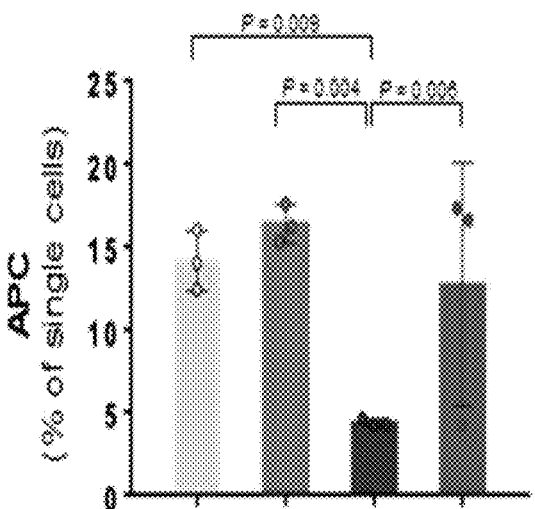
Figure 10G:
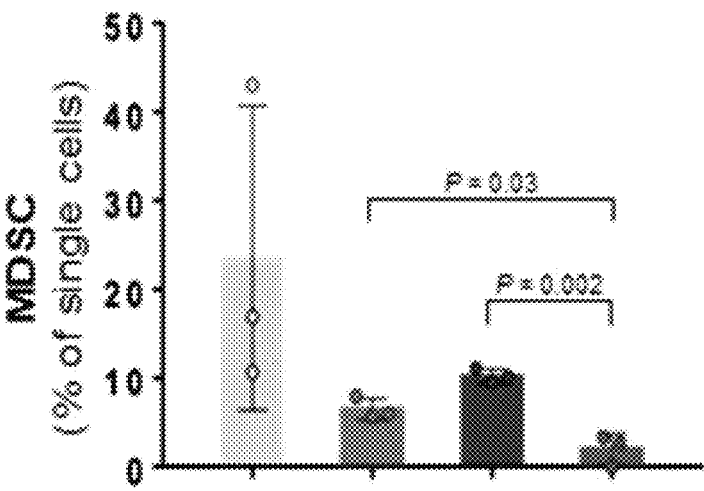
Figure 10H:
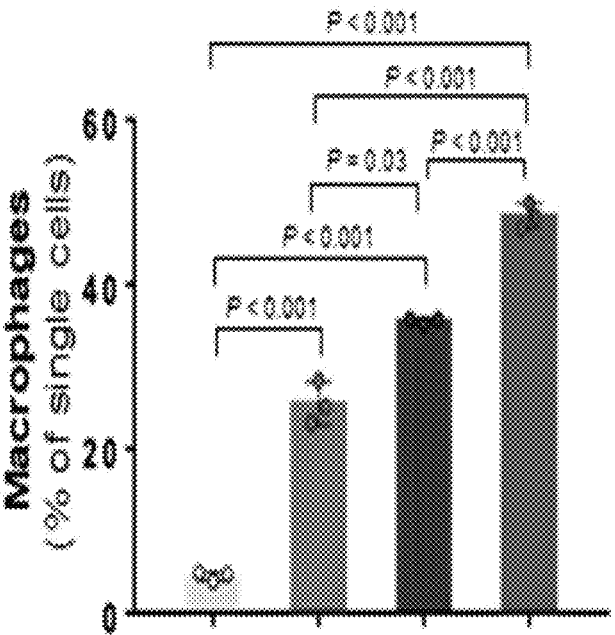

(FIG. 9A). In this case, the dosing regimen started once the animals presented palpable tumors, leading to 79% (first study FIG. 9B) and 81% (second study FIG. 9C) tumor growth inhibition at day 19 for the combination of mannosylated nano-vaccines with ibrutinib and αPD-1/αOX40, versus 67% (FIG. 9B) and 68% (FIG. 9C) for the nano-vaccines+αPD-1/αOX40 combination, and 70% (FIG. 9B) and 57% (FIG. 9C) for the αPD-1/αOX40+ibrutinib combination. The proposed mechanism was confirmed in this second melanoma model by the reduction of infiltrating MDSC and the increase of infiltrating T cells in the TME (FIGS. 10A-H). We selected Day 19 for comparison as this is the last day of the studies at which all the animals in all the groups were still present.

REFERENCES FOR EXAMPLE 1

1 Topalian, S. L. et al. Safety, Activity, and Immune Correlates of Anti-PD-1 Antibody in Cancer. New England Journal of Medicine 366, 2443-2454, doi:doi:10.1056/NEJMoa1200690 (2012).

2 Hodi, F. S. et al. Improved survival with ipilimumab in patients with metastatic melanoma. N Engl J Med 363, 711-723, doi:10.1056/NEJMoa1003466 (2010).

3 Gramaglia, I. et al. The OX40 costimulatory receptor determines the development of CD4 memory by regulating primary clonal expansion. J Immunol 165, 3043-3050 (2000).

4 Arch, R. H. & Thompson, C. B. 4-1BB and OX40 are members of a tumor necrosis factor (TNF)-nerve growth factor receptor subfamily that bind TNF receptor-associated factors and activate nuclear factor kappaB. Mol Cell Biol 18, 558-565 (1998).

5 Aspeslagh, S. et al. Rationale for anti-OX40 cancer immunotherapy. Eur J Cancer 52, 50-66, doi:10.1016/j.ejca.2015.08.021 (2016).

6 Sarff, M. et al. OX40 (CD134) expression in sentinel lymph nodes correlates with prognostic features of primary melanomas. Am J Surg 195, 621-625; discussion 625, doi:10.1016/j.amjsurg.2007.12.036 (2008).

7 Vetto, J. T. et al. Presence of the T-cell activation marker OX-40 on tumor infiltrating lymphocytes and draining lymph node cells from patients with melanoma and head and neck cancers. Am J Surg 174, 258-265 (1997).

8 Spranger, S. et al. Mechanism of tumor rejection with doublets of CTLA-4, PD-1/PD-L1, or IDO blockade involves restored IL-2 production and proliferation of CD8+ T cells directly within the tumor microenvironment. Journal for ImmunoTherapy of Cancer 2, 3, doi:10.1186/2051-1426-2-3 (2014).

9 Gajewski, T. F. The Next Hurdle in Cancer Immunotherapy: Overcoming the Non-T-Cell-Inflamed Tumor Microenvironment. Semin Oncol 42, 663-671, doi:10.1053/j.seminoncol.2015.05.011 (2015).

10 Minn, A. J. & Wherry, E. J. Combination Cancer Therapies with Immune Checkpoint Blockade: Convergence on Interferon Signaling. Cell 165, 272-275, doi:10.1016/j.cell.2016.03.031 (2016).

11 Tumeh, P. C. et al. PD-1 blockade induces responses by inhibiting adaptive immune resistance. Nature 515, 568-571, doi:10.1038/nature13954 (2014).

12 van Kooyk, Y. C-type lectins on dendritic cells: key modulators for the induction of immune responses. Biochem Soc Trans 36, 1478-1481, doi:10.1042/BST0361478 (2008).

13 Kodumudi, K. N., Weber, A., Sarnaik, A. A. & Pilon-Thomas, S. Blockade of myeloid-derived suppressor cells after induction of lymphopenia improves adoptive T cell therapy in a murine model of melanoma. J Immunol 189, 5147-5154, doi:10.4049/jimmunol.1200274 (2012).

14 Meyer, C. et al. Frequencies of circulating MDSC correlate with clinical outcome of melanoma patients treated with ipilimumab. Cancer Immunol Immunother 63, 247-257, doi:10.1007/s00262-013-1508-5 (2014).

15 Stiff, A. et al. Myeloid-Derived Suppressor Cells Express Bruton's Tyrosine Kinase and Can Be Depleted in Tumor-Bearing Hosts by Ibrutinib Treatment. Cancer Research 76, 2125-2136, doi:10.1158/0008-5472.Can-15-1490 (2016).

16 Natarajan, G. et al. A Tec kinase BTK inhibitor ibrutinib promotes maturation and activation of dendritic cells. OncoImmunology 5, doi:10.1080/2162402x.2016.1151592 (2016).

17 Alonso-Sande, M. et al. Development of PLGA-mannosamine nanoparticles as oral protein carriers. Biomacromolecules 14, 4046-4052, doi:10.1021/bm401141u (2013).

18 Silva, J. M. et al. In vivo delivery of peptides and Toll-like receptor ligands by mannose-functionalized polymeric nanoparticles induces prophylactic and therapeutic anti-tumor immune responses in a melanoma model. J Control Release 198, 91-103, doi:10.1016/j.jconrel.2014.11.033 (2015).

19 Wang, X., Ramstrom, 0. & Yan, M. Dynamic light scattering as an efficient tool to study glyconanoparticle-lectin interactions. Analyst 136, 4174-4178, doi:10.1039/c1an15469a (2011).

20 De Koker, S. et al. Engineering Polymer Hydrogel Nanoparticles for Lymph Node-Targeted Delivery. Angew Chem Int Ed Engl 55, 1334-1339, doi:10.1002/anie.201508626 (2016).

21 Azzi, J. et al. Targeted Delivery of Immunomodulators to Lymph Nodes. Cell Rep 15, 1202-1213, doi:10.1016/j.celrep.2016.04.007 (2016).

22 Seliger, B., Ruiz-Cabello, F. & Garrido, F. IFN inducibility of major histocompatibility antigens in tumors. Adv Cancer Res 101, 249-276, doi:10.1016/S0065-230X(08)00407-7 (2008).

23 Dranoff, G. et al. Vaccination with irradiated tumor cells engineered to secrete murine granulocyte-macrophage colony-stimulating factor stimulates potent, specific, and long-lasting anti-tumor immunity. Proc Natl Acad Sci USA 90, 3539-3543 (1993).

24 Kowalczyk, D. W. et al. Vaccine-induced CD8+ T cells eliminate tumors by a two-staged attack. Cancer Gene Ther 10, 870-878, doi:10.1038/sj.cgt.7700653 (2003).

25 Pasare, C. & Medzhitov, R. Toll-like receptors: balancing host resistance with immune tolerance. Curr Opin Immunol 15, 677-682 (2003).

26 Scheller, J., Chalaris, A., Schmidt-Arras, D. & Rose-John, S. The pro- and anti-inflammatory properties of the cytokine interleukin-6. Biochim Biophys Acta 1813, 878-888, doi:10.1016/j.bbamcr.2011.01.034 (2011).

27 Fridlender, Z. G. et al. CCL2 blockade augments cancer immunotherapy. Cancer Res 70, 109-118, doi:10.1158/0008-5472.CAN-09-2326 (2010).

28 Tsui, P. et al. Generation, characterization and biological activity of CCL2 (MCP-1/JE) and CCL12 (MCP-5) specific antibodies. Hum Antibodies 16, 117-125 (2007).

29 Phan, G. Q. et al. Immunization of patients with metastatic melanoma using both class I- and class II-restricted peptides from melanoma-associated antigens. J Immunother 26, 349-356 (2003).

30 Slingluff, C. L., Jr. et al. A randomized phase II trial of multiepitope vaccination with melanoma peptides for cytotoxic T cells and helper T cells for patients with metastatic melanoma (E1602). Clin Cancer Res 19, 4228-4238, doi:10.1158/1078-0432.CCR-13-0002 (2013).

31 Shedlock, D. J. & Shen, H. Requirement for CD4 T cell help in generating functional CD8 T cell memory. Science 300, 337-339, doi:10.1126/science.1082305 (2003).

32 Gabrilovich, D. I. & Nagaraj, S. Myeloid-derived suppressor cells as regulators of the immune system. Nat Rev Immunol 9, 162-174, doi:10.1038/nri2506 (2009).

33 Nagaraj, S., Schrum, A. G., Cho, H. I., Celis, E. & Gabrilovich, D. I. Mechanism of T cell tolerance induced by myeloid-derived suppressor cells. J Immunol 184, 3106-3116, doi:10.4049/jimmunol.0902661 (2010).

34 Sagiv-Barfi, I. et al. Therapeutic antitumor immunity by checkpoint blockade is enhanced by ibrutinib, an inhibitor of both BTK and ITK. Proceedings of the National Academy of Sciences 112, E966-E972, doi:10.1073/pnas.1500712112 (2015).

35 Swart, M., Verbrugge, I. & Beltman, J. B. Combination Approaches with Immune-Checkpoint Blockade in Cancer Therapy. Front Oncol 6, 233, doi:10.3389/fonc.2016.00233 (2016).

36 Guo, Z. et al. PD-1 blockade and OX40 triggering synergistically protects against tumor growth in a murine model of ovarian cancer. PLoS One 9, e89350, doi:10.1371/journal.pone.0089350 (2014).

37 Woods, D. M., Ramakrishnan, R., Sodré, A. L., Berglund, A. & Weber, J. Abstract A067: PD-1 blockade enhances OX40 expression on regulatory T-cells and decreases suppressive function through induction of phospho-STAT3 signaling. Cancer Immunology Research 4, A067-A067, doi:10.1158/2326-6066.imm2016-a067 (2016).

38 Zhu, Q. et al. Using 3 TLR ligands as a combination adjuvant induces qualitative changes in T cell responses needed for antiviral protection in mice. J Clin Invest 120, 607-616, doi:10.1172/JCI39293 (2010).

39 Chen, L. & Flies, D. B. Molecular mechanisms of T cell co-stimulation and co-inhibition. Nat Rev Immunol 13, 227-242, doi:10.1038/nri3405 (2013).

40 Hanahan, D. & Coussens, L. M. Accessories to the crime: functions of cells recruited to the tumor microenvironment. Cancer Cell 21, 309-322, doi:10.1016/j.ccr.2012.02.022 (2012).

41 Burkholder, B. et al. Tumor-induced perturbations of cytokines and immune cell networks. Biochim Biophys Acta 1845, 182-201, doi:10.1016/j.bbcan.2014.01.004 (2014).

42 Fang, H. et al. TLR4 is essential for dendritic cell activation and anti-tumor T-cell response enhancement by DAMPs released from chemically stressed cancer cells. Cellular & Molecular Immunology 11, 150-159, doi:10.1038/cmi.2013.59 (2013).

43 Beyersdorf, N., Kerkau, T. & Hunig, T. CD28 co-stimulation in T-cell homeostasis: a recent perspective. Immunotargets Ther 4, 111-122, doi:10.2147/ITT.S61647 (2015).

44 Sagiv-Barfi, I. et al. Eradication of spontaneous malignancy by local immunotherapy. Sci Transl Med 10, doi:10.1126/scitranslmed.aan4488 (2018).

45 Maher, E. A., Mietz, J., Arteaga, C. L., DePinho, R. A. & Mohla, S. Brain metastasis: opportunities in basic and translational research. Cancer Res 69, 6015-6020, doi:10.1158/0008-5472.CAN-08-4347 (2009).

46 Santarelli, J. G., Sarkissian, V., Hou, L. C., Veeravagu, A. & Tse, V. Molecular events of brain metastasis. Neurosurg Focus 22, E1 (2007).

47 van den Eertwegh, A. J. et al. Combined immunotherapy with granulocyte-macrophage colony-stimulating factor-transduced allogeneic prostate cancer cells and ipilimumab in patients with metastatic castration-resistant prostate cancer: a phase 1 dose-escalation trial. Lancet Oncol 13, 509-517, doi:10.1016/S1470-2045(12)70007-4 (2012).

48 Hodi, F. S. et al. Ipilimumab plus sargramostim vs ipilimumab alone for treatment of metastatic melanoma: a randomized clinical trial. JAMA 312, 1744-1753, doi:10.1001/jama.2014.13943 (2014).

49 Kaiser, A. D. et al. Towards a commercial process for the manufacture of genetically modified T cells for therapy. Cancer Gene Ther 22, 72-78, doi:10.1038/cgt.2014.78 (2015).

50 Wilson, D. S. et al. Antigens reversibly conjugated to a polymeric glyco-adjuvant induce protective humoral and cellular immunity. Nat Mater 18, 175-185, doi:10.1038/s41563-018-0256-5 (2019).

51 Schwartz, H. et al. Incipient Melanoma Brain Metastases Instigate Astrogliosis and Neuroinflammation. Cancer Research 76, 4359-4371, doi:10.1158/0008-5472.can-16-0485 (2016).

Example 2

Preparation and Characterization of Mannose-Grafted PLGA/PLA Nano-Vaccine Co-Entrapping GL261 Neoantigen and TLR Ligands Mannose-grafted PLGA/PLA nano-vaccines were developed using TPGS and PL as surfactants, in addition to the internal PVA, in order to improve the mucoadhesive nature of the carrier, while enabling the co-entrapment of mImp3 D81N MHC class I neoantigen of GL261 with CpG and MPLA. The entrapment of the bioactive molecules did not change the physicochemical properties of the Man-NP (Table 6).

TABLE 6

| Physicochemical properties of different batches of GL261 neoantigenloaded man-PLGA/PLA nano-vaccine prepared with TPGS and PL as surfactants | | | | | |
|---|---|---|---|---|---|
| Formulation | Z-Ave (nm) | PdI | ZP (mV) | EE (%, w/w) | LC (µg antigen/mg polymer) |
| Man-PLGA/PLA NP_TPGS_PL | 188 ± 1.8 | 0.13 ± 0.01 | −14.5 ± 0.53 | — | — |
| mImp3 D81N-loaded Man-PLGA/PLA NP_TPGS_PL | 186 ± 12.1 | 0.13 ± 0.03 | −12.3 ± 0.27 | 84.77 ± 9.09 | 42.38 ± 4.55 |

(mean ± SD; N = 3, n = 6)

Example 3

Preparation and Characterization of Mannose-Grafted PLGA/PLA Nano-Vaccine Co-Entrapping Mutated p53R172H Antigen and TLR Ligands Against Pancreatic Ductal Adenocarcinoma (PDAC)

Mannose-grafted PLGA/PLA nano-vaccines were developed using TPGS and PL as surfactants, in addition to the internal PVA, in order to improve the mucoadhesive nature of the carrier, while enabling the co-entrapment of the peptide antigen of mouse mutated $p53_{R172H}$ MHC class I, sequence VVRHCPHHER (SEQ ID NO: 4) (human mutated $p53_{R175H}$ (sequence EVVRHCPHHE (SEQ ID NO: 5)) with TLR ligands (CpG and poly(I:C)). The entrapment of the bioactive molecules did not change the physicochemical properties of the Man-NP (Table 7).

TABLE 7

Physicochemical properties of different batches of $p53_{R172H}$ antigen-loaded man-PLGA/PLA nano-vaccine prepared with TPGS and PL as surfactants

| Formulation | Z-Ave (nm) | PdI | ZP (mV) | EE (%, w/w) | LC (µg antigen/mg polymer) |
|---|---|---|---|---|---|
| Man-PLGA/PLA NP_TPGS_PL | 185.2 ± 2.10 | 0.2 ± 0.03 | −9.6 ± 2.71 | — | — |
| $p53_{R172H}$-loaded Man- PLGA/PLA NP_TPGS_PL | 170.9 ± 3.35 | 0.17 ± 0.03 | −15.3 ± 2.36 | 71.6 ± 1.14 | 35.8 ± 0.57 |

(mean ± SD; N = 3, n = 5)

Figure 11B:
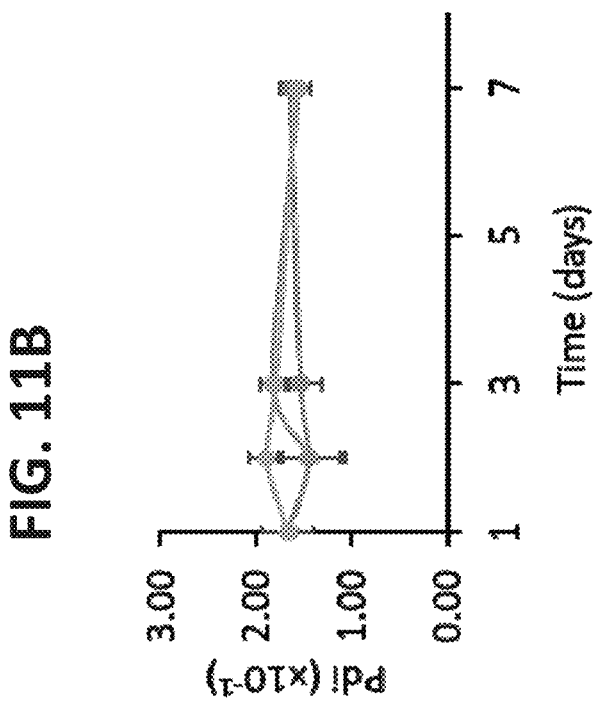
FIGS. 11A-B. Analysis of man-PLGA/PLA nano-vaccine (Man-PLGA/PLA NP_TPGS_PL) physicochemical stability in PBS pH 7.4 at 4° C., 24° C. and 37° C. (mean±SD; N=2, n=3). Nano-vaccine size and surface charge were analyzed by DLS and Laser Doppler Electrophoresis (LDE), respectively.
Figure 11A:
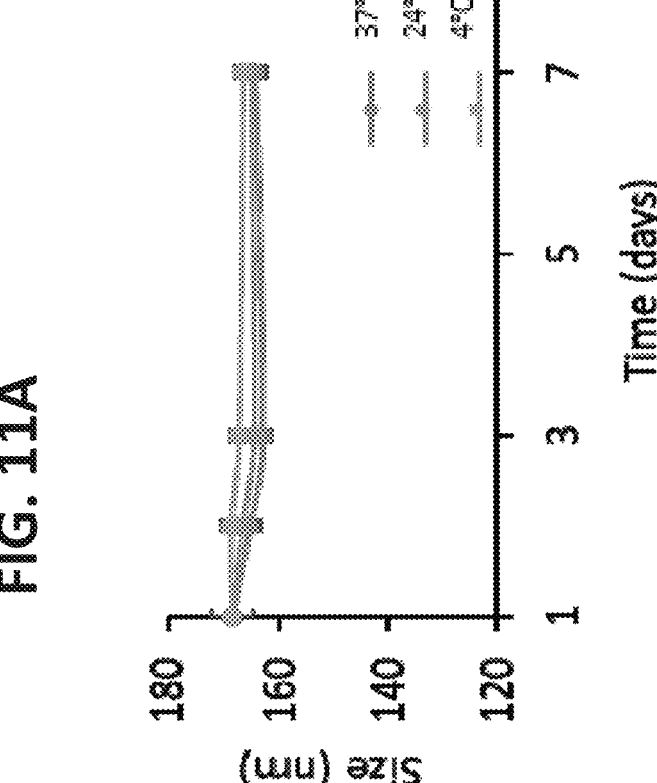

As illustrated in FIGS. 11A-B, the size and PdI of $p53_{R172H}$-loaded Man-PLGA/PLA NP_TPGS_PL was maintained at 4° C., 24° C. and 37° C.

Example 4

Preparation and Characterization of PLGA Nano-Vaccines Co-Entrapping Polyarginine-siRNA Polyplexes, TAA and TLR Ligands Non-targeted NP (no targeting moiety) were produced with a polymer core of PLGA or a polymer blend of PLGA/PLGA-PEG at different ratios (Table 8). A mixture of mannose-derivative polymers (PLGA-Man/PLGA-PEG-Man) was used to prepare DC-targeted NP.

Different emulsifying/surface active agents (e.g. PVA, PL, TPGS and hydrophilic stabilizers/viscosity enhancers with adjuvant properties (e.g. cationic cell penetrating peptide polyarginine) were used also to optimize nano-vaccine formulations, in order to achieve a stability suitable for the co-entrapment of polyarginine-siRNA polyplexes with combinations of (i) TAA (colorectal cancer (CRC)-associated peptide (CEA, Adpgk MC38 short (MHCI) and long (MHCII) neoantigen peptides) and (ii) immune regulators (ligands of TLR, including CpG, poly(I:C) and/or MPLA).

50 µg of CEA or Adpgk MC38 (neo)antigen and 1 µg of siRNA anti-PDL1 per mg of polymer was entrapped into nano-vaccine. The cell penetrating peptide, polyarginine was included in NP formulation also to improve (neo) antigen/siRNA entrapment and, as a membrane fusion potentiator, also to improve the NP internalization, as well as the endolysosomal escape and (neo)antigen/siRNA processing within the cytosol.

Blank and cargo-loaded nano-vaccine containing polyarginine at internal phase to complex 10 and 40 µg of siRNA presented a mean size diameter of about 200 nm (ranged between 207 and 236 nm), PdI values below 0.2, a surface charge close to neutrality with ZP values close to −1 mV (Table 9). Nano-vaccine presented a spherical shape and had a slightly rough surface.

The entrapment of antigen and siRNA into nano-vaccine did not change their stability, since no differences in the physicochemical properties were detected among blank and cargo-loaded NP. These multivalent delivery systems presented high EE and LC for antigen and siRNA. PLGA-based nano-vaccine were able to entrap a considerable amount of CEA, presenting EE % (w/w) ranging from 62±4% and 67±3% (w/w), and LC values ranging from 31±2 µg and 33±1 µg of CEA per mg of nano-vaccine. Moreover, siRNA anti-PDL1 was fully entrapped into PLGA-based nano-vaccine.

TABLE 8

Summary of physicochemical properties of PEG-PLGA/man-PLGA nano-vaccine (with the polypeptide polyarginine) and loading capacity for combinations of CEA antigen or Adpgk MC38 short (MHCI) and long (MHCII) neoantigen peptides, siRNA and TLR ligands, (mean ± SD; N ≥ 6, n = 3)

| Formulation | | Z-Ave (nm) | PdI | ZP (mV) | EE % | LC (µg/mg) |
|---|---|---|---|---|---|---|
| PLGA | plain | 225 ± 8 | 0.123 ± 0.026 | −0.76 ± 0.06 | — | — |
| NP_ARG | CEA | 236 ± 6 | 0.173 ± 0.022 | −0.67 ± 0.21 | 62.68 ± 4.7 | 31.34 ± 2.4 |
| PEG- | plain | 214 ± 11 | 0.09 ± 0.01 | −0.89 ± 0.11 | — | — |

TABLE 8-continued

Summary of physicochemical properties of PEG-PLGA/man-PLGA nano-vaccine
(with the polypeptide polyarginine) and loading capacity for combinations
of CEA antigen or Adpgk MC38 short (MHCI) and long (MHCII) neoantigen
peptides, siRNA and TLR ligands, (mean ± SD; N ≥ 6, n = 3)

| Formulation | | Z-Ave (nm) | PdI | ZP (mV) | EE % | LC (μg/mg) |
|---|---|---|---|---|---|---|
| PLGA | CEA | 207 ± 16 | 0.117 ± 0.078 | −0.83 ± 0.16 | 62.28 ± 4.3 | 31.14 ± 2.2 |
| NP | CEA | 216 ± 10 | 0.096 ± 0.025 | −0.59 ± 0.12 | 66.60 ± 3.5 | 33.30 ± 1.7 |
| (10% w/w) | siRNA anti-PDL1 | | | | 99.92 ± 0.1 | 1.00 ± 0.0 |
| Man-PLGA/PEG-PLGA NP (20% w/w) | plain | 205 ± 5 | 0.09 ± 0.02 | −0.76 ± 0.06 | — | — |
| | MHCI-Adpgk | 229 ± 5 | 0.18 ± 0.01 | −2.01 ± 0.46 | 51.2 ± 1.0 | 25.6 ± 0.5 |
| | MHCII-Adpgk | 226 ± 9 | 0.14 ± 0.01 | −6.96 ± 0.93 | 66.9 ± 0.9 | 33.5 ± 0.5 |
| Man-PEG-PLGA NP (20% w/w) | plain | 216 ± 8 | 0.11 ± 0.03 | −0.86 ± 0.22 | — | — |
| | MHCI-Adpgk | 231 ± 16 | 0.17 ± 0.01 | −2.46 ± 1.20 | 55.6 ± 1.1 | 27.8 ± 0.6 |
| | MHCII-Adpgk | 239 ± 5 | 0.16 ± 0.05 | −6.64 ± 1.07 | 70.5 ± 1.4 | 35.2 ± 0.7 |
| PEG-PLGA NP (100% w/w) | plain | 169 ± 3 | 0.18 ± 0.02 | −0.67 ± 0.21 | — | — |
| Man-PLGA-PEGNP (10% w/w) | plain | 208 ± 7 | 0.12 ± 0.02 | −0.92 ± 0.13 | — | — |
| Man-PLGA/PEG-PLGA NP (30% w/w) | plain | 208 ± 2 | 0.09 ± 0.01 | −0.92 ± 0.26 | — | — |
| Man-PEG-PLGA NP (10% w/w) | plain | 217 ± 10 | 0.12 ± 0.02 | −0.98 ± 0.07 | — | — |
| Man-PEG-PLGA NP (30% w/w) | plain | 206 ± 1 | 0.14 ± 0.01 | −0.84 ± 0.12 | — | — |

CEA: carcinoembriogenic antigen; CpG: cytosine phosphorothioate-guanine motifs; DC: dendritic cell; EE: entrapment efficiency; LC: loading capacity; Man: mannose; MHC: major histocompatibility complex; NP: nanoparticle; ODN: oligodeoxynucleotides; PdI, polydispersity index; PEG: poly(ethylene glycol); Poly(I:C): polyinosinic: polycytidylic acid; PLGA: poly(lactic-co-glycolic) acid; SD: standard deviation; siRNA: small interfering RNA; All NP contain TLR ligands CpG, Poly (I:C).

Different levels of entrapment efficiency (EE) and loading capacity (LC) were obtained for MHCI-Adpgk, MHCII-Adpgk and CEA antigens, according to NP composition and type of antigen (Table 8). In general, nano-vaccines displayed high loading levels for the CEA peptide (EE >62.3±4.3%, LC >31.1±2.2 Wing). Even though, higher EE and LC values were obtained for the large peptide MHCII-Adpgk.

Example 5

Preparation and Characterization of PLGA/PLA Nano-Vaccines Co-Entrapping Amphiphilic Alkylated Poly(a)Glutamate Amine (APA)-siRNA Polyplexes, TAA and TLR Ligands Different emulsifying/surface active agents (e.g PVA, PL and TPGS) were used to co-entrap PGA-siRNA polyplexes with combinations of TAA (MART-1 and OVA short (MHCI) and long peptides (MHCII), MUT30 B 16F10 neoantigens) and immune regulators (ligands of TLR, as CpG, poly(I:C) and/or MPLA). The proportion of 50 μg antigen (Mart-1, MUT30 B 16F10 neoantigen and OVA MHC class 1 and OVA MHC class II antigens) and 1:2 siPD-L1:APA ratio were entrapped into nano-vaccine. APA was included in the nano-vaccine to improve antigen and oligonucleotides entrapment and delivery by DC-targeted carriers, but also to assess its potential adjuvant effect on DC-targeted NP.

1. Mannose-Grafted PLGA/PLA Nano-Vaccine Co-Entrapping siRNA and TLR Ligands.

Blank and MART-1-loaded nano-vaccine containing APA at internal phase to complex siRNA presented a mean size diameter close to 200 nm (ranged between 184 and 220 nm), PdI values below 0.2, a surface charge close to neutrality with ZP values close to −1 mV (Table 9).

The entrapment of antigen and siRNA into PLGA/PLA nano-vaccine platform did not change their stability, since no differences in the physicochemical properties were detected among blank and cargo-loaded nano-vaccine. siPD-L1 was mostly entrapped into PLGA/PLA-based nano-vaccine.

TABLE 9

Summary of physico-chemical properties of PLGA/PLA nano-vaccine
entrapping APA-siRNA complexes and loading capacity for combinations
of siRNA and TLR ligands, (mean ± SD; N = 3, n = 3).

| Formulation | | Z-Ave (nm) | PdI | ZP (mV) | EE % | LC (µg siRNA/µg polymer) |
|---|---|---|---|---|---|---|
| PLA NP | PVA | 209 ± 4.3 | 0.06 ± 0.01 | −1.08 ± 0.19 | — | — |
| | TPGS | 189 ± 5.6 | 0.12 ± 0.003 | −4.82 ± 0.49 | — | — |
| APA-loaded PLA NP_TPGS | H2O | 184 ± 0.2 | 0.12 ± 0.01 | −0.68 ± 0.29 | — | — |
| | siPD-L1 | 185 ± 1.5 | 0.14 ± 0.003 | −1.03 ± 0.12 | 95.91 ± 0.25 | 0.959 ± 0.002 |
| APA-loaded PLA NP_PVA | H2O | 220 ± 7.4 | 0.06 ± 0.01 | −0.88 ± 0.12 | — | — |
| | siPD-L1 | 206 ± 1.9 | 0.09 ± 0.02 | −0.79 ± 0.2 | 94.04 ± 0.28 | 0.940 ± 0.003 |

2. Mannose-Grafted PLGA/PLA Nano-Vaccine Co-Entrapping OVA MHCI and MHCII Peptides, siRNA and TLR Ligands NPs were developed from a blend of four aliphatic polyester copolymers: PLGA, PLA, pegylated PLGA (PEG-PLGA) and/or mannose-grafted PLGA (man-PLGA). Two different types of NP were formulated, one being based on PLGA co-polymer and the other on the PLA co-polymer (Table 10). Different surfactants (PVA, PL, TPGS) were used to improve NP stability, while looking at the entrapment of combinations of bioactive molecules (e.g. protein antigens, adjuvants and siPD-L1 polyplexes), as well as to the mucoadhesive nature of the nano-vaccine for nasal administration (Table 11).

TABLE 10

Composition of the different Man-grafted PLGA/PLA NP formulations

| Formulation | Polymers ratios | IP[a] | EP[b] | FP[c] |
|---|---|---|---|---|
| Man-PLGA[d]/PEG-PLGA NP_PVA_PVA | PLGA: man-PLGA: PEG[f]-PLGA 7:2:1 | 15%(w/v) PVA[g] | 5% (w/v) PVA | 0.25% (w/v) PVA |
| Man-PLGA/PEG-PLGA NP_TPGS_PVA | | | 2.5% (w/v) TPGS[b] | 0.25% (w/v) PVA |
| Man-PLGA/PEG-PLGA NP_TPGS_PL | | | | 0.125% (w/v) PL[i] |
| Man-PLGA/PEG-PLGA/PLA NP_TPGS_PVA | PLA: man-PLGA: PEG-PLGA 7:2:1 | | | 0.25% (w/v) PVA |
| Man-PLGA/PEG-PLGA/PLA NP_TPGS_PL | | | | 0.125% (w/v) PL |

[a]internal aqueous phase;
[b]external aqueous phase;
[c]final aqueous phase;
[d]poly (lactic-co-glycolic-acid);
[e]poly (L-lactic-acid);
[f] poly (lactic-co-glycolic-acid) conjugated with polyethylene glycol;
[g]poly (vinyl alcohol);
[h]a-Tocopherol polyethylene glycol 1000 succinate;
[i]poloxamer 407 (pluronic F-127).

TABLE 11

Physicochemical characterization of empty man-NP. .

| Formulation | Size (nm) | PdI[a] | ZP[b]/mV |
|---|---|---|---|
| Man-PLGA[c]/PEG-PLGA NP_PVA[d]_PVA | 239.36 ± 34.37 | 0.16 ± 0.07 | −1.96 ± 0.11 |
| Man-PLGA/PEG-PLGA NP_TPGS_PVA | 204.20 ± 9.11 | 0.14 ± 0.03 | −2.65 ± 0.36 |
| Man-PLGA/PEG-PLGA NP_TPGS_PL[e] | 187.63 ± 6.45 | 0.12 ± 0.04 | −3.70 ± 0.47 |
| Man-PLGA/PEG-PLGA/PLA[f] NP_TPGS_PVA | 210.30 ± 20.57 | 0.22 ± 0.08 | −8.05 ± 0.67 |
| Man-PLGA/PEG-PLGA/PLA NP_TPGS_PL | 182.80 ± 4.63 | 0.14 ± 0.02 | −12 ± 0.85 |

Mean ± SD, 3≤ n ≤ 6
[a]polydispersity index;
[b]zeta Potential;
[c]poly (lactic-co-glycolic acid);
[d]poly (vinyl-alcohol);
[e]poloxamer 407 (pluronic F-127);
fpoly (L-lactic acid);

TPGS decreased NP mean average diameter from 239.36±34.37 nm to 204.20±9.11 nm for PLGA-based NP (Man-PLGA/PEG-PLGA NP_TPGS_PVA), and to 210.30±20.57 nm for PLA-based NP (Man-PLGA/PEG-PLGA/PLA NP_TPGS_PVA). Man-PLA-based NP developed using both PL and TPGS showed the most favourable physicochemical properties for DC targeting, especially following its nasal administration. Therefore, the nano-vaccine Man-PLGA/PEG-PLGA/PLA NP_TPGS_PL (herein after Man-PLGA/PLA NP_TPGS_PL) was further used to entrap the combination of distinct biomolecules.

Different bioactive molecules were entrapped within NP: MHCI-OVA (MHCI-ag), MHCII-OVA (MHCII-ag), the oligonucleotide CpG, poly(I:C) and the siPD-L1. All nano-vaccines presented a size range between 190 nm and 215 nm, and the PdI was always lower than 0.2 (Table 12). The NP surface charge increased to values close to −30 mV for all nano-vaccines, in comparison with empty NP. In addition, the lower SD obtained for the three physicochemical parameters under discussion demonstrates that the double-emulsion solvent evaporation method used for NP preparation was highly reproducible.

TABLE 12

| Man/PEG-PLGA/PLA Nano-vaccine physico-chemical properties. | | | |
|---|---|---|---|
| Formulations | Size (nm) | PdI[a] | ZP[b]/mV |
| Man-PLGA/PLA[c] NP_TPGS_PL[d] (empty) | 182.80 ± 4.63 | 0.14 ± 0.02 | −12 ± 0.85 |
| MHCI-ag[e] — loaded Man-PLGA/PLA NP_TPGS_PL | 209.93 ± 0.12 | 0.14 ± 0.01 | −31.55 ± 5.02 |
| MHCII-ag[f] — loaded Man-PLGA/PLA NP_TPGS_PL | 199.50 ± 1.18 | 0.12 ± 0.01 | −30.90 ± 2.40 |
| MHCI-ag/siPD-L1[g] — loaded Man-PLGA/PLA NP_TPGS_PL | 214.73 ± 5.25 | 0.13 ± 0.02 | −30.85 ± 9.12 |
| MHCII-ag/siPD-L1[g] — loaded Man-PLGA/PLA NP_TPGS_PL | 188.90 ± 2.13 | 0.13 ± 0.01 | −26.65 ± 1.63 |

Mean ± SD; n = 3.

[a]polydispersity index;

[b]zeta potential;

[c]poly (L-lactic-acid);

[d]poloxamer 407 (pluronic F-127);

[e]MHCI-OVA;

[f]MHCII-OVA;

[g]siRNA PD-L1 (siPD-L1). CpG and poly(I:C) were entrapped in all NP, with exception of empty nanoparticulate system.

The EE and LC of the nano-vaccine regarding the different bioactive molecules co-entrapped depended on the properties of the entrapped bioactive molecule, being high for both OVA peptide antigens (Table 13).

TABLE 13

Entrapment efficiency (EE, % (w/w) and loading capacity (LC, μg/mg) of MHCI-ag, MHCII-ag, CpG, Poly(I:C) and siPD-L1-APA polyplex entrapped in Man-PLGA/PLA NP TPGS PL NP.

| Formulations | Antigens EE[a] LC[b] | CpG EE LC | Poly(I:C) EE LC | siPD-L1 EE LC |
|---|---|---|---|---|
| MHCI-ag[c]/siPD-Ll[e] — loaded Man-PLGA/PLA NP_TPGS_PL | 101.84 ± 3.79 50.90 ± 1.90 | 88.15 ± 1.50 24.68 ± 0.42 | 66.02 ± 13.35 21.13 ± 4.27 | 99.10 ± 0.19 31.70 ± 0.06 |
| MHCII-ag[d]/siPD-L1 — loaded Man-PLGA/PLA NP_TPGS_PL | 99.40 ± 6.02 49.73 ± 3.01 | 88.48 ± 1.56 24.77 ± 0.44 | 62.16 ± 3.36 19.89 ± 1.07 | 96.60 ± 0.45 11.60 ± 0.05 |

[a]Entrapment efficiency (%);

[b]Loading capacity (μg/ml);

[c]MHCI-OVA;

[d]MHCII-OVA;

[e]siRNA anti-PD-L1.

Mean ± SD; 3 ≤ n ≤ 5.

Figures 12A, 12B, 12C:
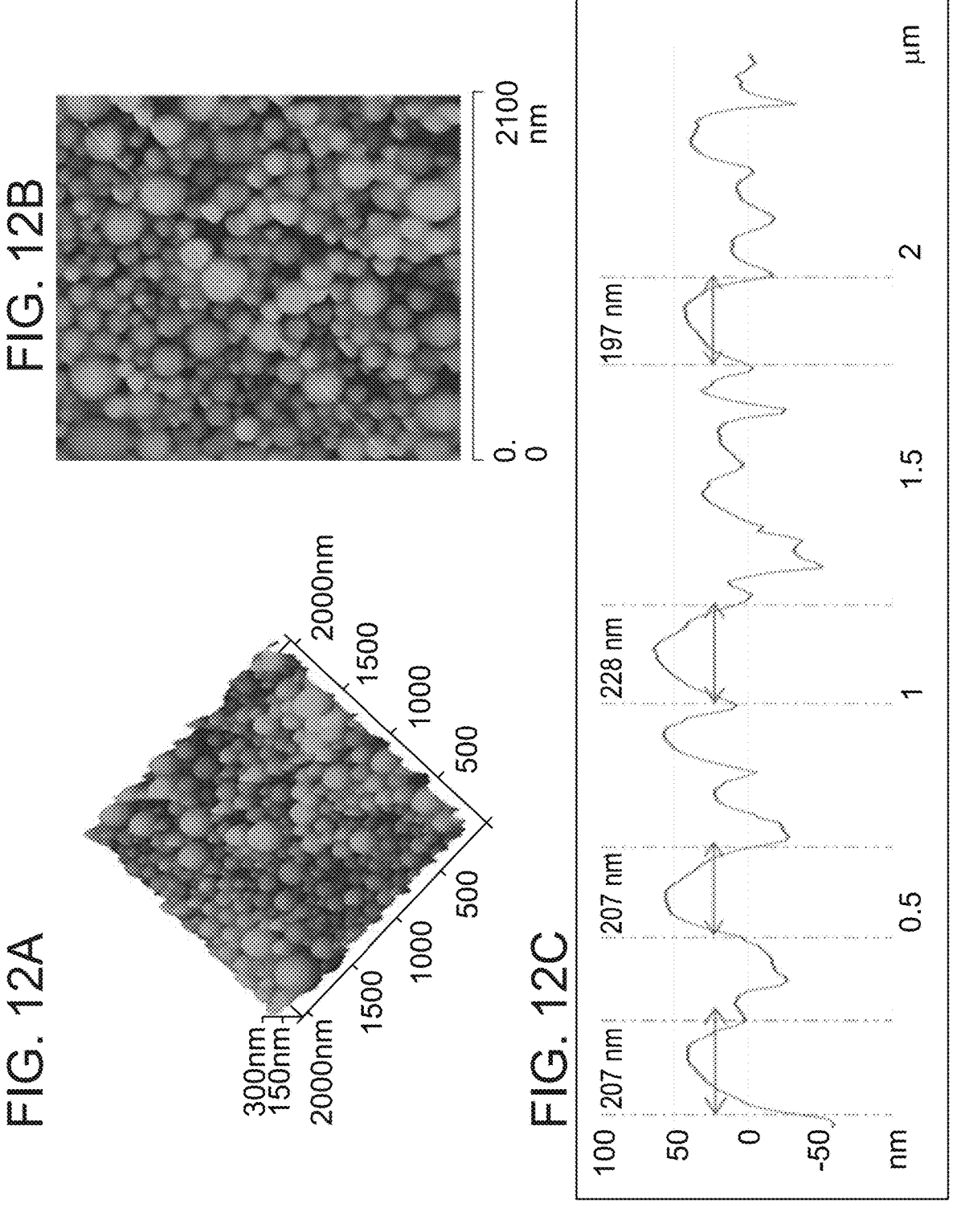
FIGS. 12A-C. Nanoparticle (NP) (Man-PLGA/PLA NP_TPGS_PL) surface morphology by atomic force microscopy (AFM). (A) and (B) show topography images of spherical NP, showing narrow size polydispersity; (C) NP diameter obtained from section analysis.

Nano-vaccine platform surface morphology was analyzed by Atomic Force Microscopy (AFM). AFM images (FIGS. 12A-C) show a low variability in terms of NP size. In addition, man-Man-PLGA/PLA NP_TPGS_PL presented a smooth surface with slight roughness and a spherical-shaped topography. This nanoplatform presented an acceptable size range of 197-228 nm, according to our targeted specification looking at their internalization by DC, which correlated with the data obtained by DLS (182.80±4.63 nm, Table 12).

There were no significant deviations in terms of size, PdI and surface charge for the Man-PLGA/PLA NP_TPGS_PL suspension in PBS pH 7.4 over the 5 weeks of storage at 4° C. or 37° C.

3. Mannose-Grafted PLGA/PLA Nano-Vaccine Co-Entrapping MUT30, siRNA and TLR Ligands The nano-vaccine presented physico-chemical properties suitable for DC targeting, even when co-entrapping high loadings of combinations of antigens and TLR ligands with APA-siPD-L1 complexes (Tables 14 and 15).

TABLE 14

Summary of physico-chemical properties of nano-vaccine (Man-PLGA/PLA NP TPGS PL) entrapping PGA-siPD-L1 complexes of MUT30 antigen, siRNA and TLR ligands.

| Formulation | Z-Ave(nm) | PdI | ZP (mV) |
|---|---|---|---|
| Man-PLGA/PLA NP_TPGS_PL (empty) | 188 ± 1.8 | 0.13 ± 0.02 | −3.29 ± 0.34 |
| MUT30/siPD-L1 — loaded Man-PLGA/PLA NP_TPGS_PL | 216 ± 4.7 | 0.2 ± 0.01 | −3.43 ± 0.20 |

(mean ± SD; N = 3, n = 3).

TABLE 15

Summary of loading capacities and entrapment efficiencies (%) of nano-vaccine entrapping PGA- siPD-L1 complexes of MUT30 antigen, siRNA and TLR ligands, (mean ± SD; N = 3, n = 3).

| Formulation | EE MUT30 (%) | EC (μg MUT30/ mg polymer) | EE siRNA (%) | LC (μg siRNA/ μg polymer) | EE PGA (%) | LC (μg PGA/ μg polymer) |
|---|---|---|---|---|---|---|
| MUT30/siPD-L1 - loaded Man-PLGA/PLA NP_TPGS_PL | 60.83 ± 6.54 | 30.42 ± 3.27 | 97.5 ± 0.34 | 11.7 ± 0.04 | 99.4 ± 0.20 | 31.8 ± 0.06 |

PGA- siPD-L1 complexes of MUT30 antigen, siRNA and TLR ligands, (mean ± SD; N = 3, n = 3).

Example 6

In Vitro Evaluation of Nano-Vaccine Interaction with Targeted Cells

Mannose-grafted PLGA/PLA nano-vaccines (co-entrapping OVA, MHCI and MHCII peptides, APA-siRNA and TLR) were prepared.

JAWSII DC ($25 \times 10^3$ cells/well) were seeded in 96-well plates and incubated at 37° C. in a humidified incubator containing 5% $CO_2$. The cell viability of DC in the presence of Cy5-labeled NP at 0.50 mg/ml was evaluated by propidium iodide (PI) assay. After the incubation period, cells were washed with PBS and PI at 2 μg/ml in cytometry buffer (PBS sterile buffer+2% FBS) was added to each well. Fluorescence measurements were performed at excitation wavelength of 530 nm and emission of 590 nm using an LSRFortessa2 cytometer (BD Biosciences) with HTS. Untreated cells were used as control and the results were analyzed with FlowJo software version 9.8 for Microsoft (TreeStar, San Carlos, CA). The viability of JAWSII DC was not affected by the developed NP, since cell viability remained above 88%.

Example 7

In Vivo Intervention Study Using Mannose-Grafted PLGA Nano-Vaccine Platform (Co-Entrapping Polyarginine, MC38 Neoantigens and TLR Ligands) in MC38 Colorectal Carcinoma Mouse Model To select the nano-vaccine with the greatest anti-tumor effect against CRC, orthotopic MC38-bearing C57BL/6J mice were treated with three doses of the nano-vaccines synthesized using 20% (w/w) Man-PLGA/PEG-PLGA (Table 8, herein above), seven days apart according to the dosing schedule described in FIG. 13A. Anti-tumor immune-mediated response was strongly enhanced by man-grafted nano-vaccines (FIG. 13C, D), with minimal systemic toxicity (FIG. 13B). 20 days following tumor inoculation, the average tumor volume of mice groups treated with both man-grafted nano-vaccine formulations was significantly lower from those treated with PBS (P<0.0001) (FIG. 13C). Although different from PBS-treated group, the nano-vaccine-treated groups also presented significantly different tumor volumes. Of note, mice treated with Man-PLGA/PEG-PLGA NP presented significantly smaller average tumor volume than those presented by mice treated with Man-PEG-PLGA NP (P=0.0050) (FIG. 13C). Even though, no significant differences (P >0.05) were observed between the average tumor volumes obtained for mice treated with Man-PLGA/PEG-PLGA NP or Man-PEG-PLGA NP at day 24 after tumor inoculation (FIG. 13D).

Example 8

In Vivo Intervention Study Using Mannose-Grafted PLGA/PLA Nano-Vaccine Platform (Co-Entrapping OVA MHC Class I and MHC Class H Peptides, APA-PD-L1 siRNA Polyplexes and TLR Ligands) in B16MO5 Melanoma Mouse Model Man-PLGA/PLA nano-vaccine was synthesized using TPGS and PL127.

To determine the anti-tumor effect of nasal administration of the nano-vaccine against melanoma, three doses of the nano-vaccine were administered, seven days apart, to the orthotopic B16F10 mouse model.

On day 0, male C57BL/6 mice (8 weeks old) were subcutaneously inoculated with 100 µl of cell suspension containing $3\times10^5$ B16-OVA cells. Mice were anesthetized with isoflurane vaporizer. The right dorsal area was shaved before the injection. Mice were randomized into four groups (n=6): (1) PBS; (2) Free antigens and adjuvants control mixture (OVA antigen peptide (MHC I e II), CpG and Poly(I:C)); (3) NP (NP with OVA MHC I or MHC II, CpG, Poly(I:C)) and (4) NP_siPD-L1 (NP with siPD-L1, OVA MHC I or MHC II, CpG, Poly(I:C)).

Mice were immunized with the respective treatment on day 11, 18 and 25, following tumor inoculation. Immunization treatments (50 µl) were administered in each mouse via nasal route. Since the two antigens were administered to the same mouse, 25 µl of each OVA peptide loaded-NP was administered. Therefore, half dose of each treatment (12.5 µl) was given in the right nostril and the other half on the left nostril. Each dose contained 100 µg of antigens (50 µg of OVA-MHCI and 50 µg of OVA-MHCII), 20 µg of CpG, 40 µg of Poly(I:C) and/or 25 µg of siPD-L1, either in free solution or entrapped in nano-vaccine.

Tumor size was measured 3 days a week with a caliper. Tumor volume was determined by $X^2 \cdot Y \cdot 0.5$ (X·smaller diameter; Y·larger diameter) and body weight was monitored. The animals were euthanized 39 days after tumor inoculation.

Groups treated with the nano-vaccine only or the nano-vaccine entrapping siPD-L1 showed a similar average tumor volume at day 31, which was significantly lower than those presented by animals from the control group PBS (*P<0.05) (FIG. 14). In addition, the administration of antigens and adjuvants in free solution also restricted the tumor growth compared with PBS group, however, with lower efficacy than the nano-vaccines.

Example 9

In Vivo Intervention Study Using Mannose-Grafted PLGA/PLA Nano-Vaccine Platform (Co-Entrapping MUT 30 Neopeptide, APA-PD-L1 siRNA Polyplexes and TLR Ligands) in B16F10 Melanoma Mouse Model Man-PLGA/PLA nano-vaccine was synthesized using TPGS and PL, entrapping combinations of siPD-L1 with MUT30 peptide and TLR ligands (CpG and poly (I:C)). The immune-mediated anti-tumor effect induced by the intranasal administration of the nano-vaccine (20 µL containing 100 µg of antigens, 20 µg of CpG and 40 µg poly (I:C): 10 µL in each nostril) was evaluated, either alone or in combination with the intra-tumoral administration of nano-vaccines entrapping siPD-L1+TLR ligands (CpG and poly (I:C)) (days 7, 14 and 21). The modulation of the PD-L1 pathway synergized with the nano-vaccine, leading to an enhanced effect, stronger than the one induced by each of the treatments alone (FIG. 15).

Example 10

In Vivo Intervention Study Using Mannose-Grafted PLGA/PLA Nano-Vaccine Platform (Co-Entrapping GL261 Neoantigen and TLR Ligands) in Glioblastoma Mouse Model P-Selectin (SELP) is expressed by glioblastoma cells and induces a microglia activation state. When binding to P-Selectin ligand (PSGL) expressed by microglia cells, SELP alters the microglia phenotype toward M2-like state which allows them to support tumor growth and suppress cytotoxic T cells. It was hypothesized that by combining SELP knockdown with a nano-vaccine containing glioblastoma neoantigen peptide, it would be possible to harness both innate and adoptive immune systems against the tumor. Hence, mannose-grafted nanoparticles were synthesized encapsulating neoantigens expressed by murine GL261 glioblastoma cells (m1mp3 D81N MHC I (AALLNKLYA—SEQ ID NO: 6)

Human embryonic kidney 293T (HEK 293T) cells were co-transfected with the plasmids of murine SELP shRNA and murine negative control shRNA, and with the compatible packaging plasmids (pMD.G.VSVG and pGag-pol.gpt). Forty-eight hours following transfection, the retroviral particle-containing supernatants were collected. Murine GL261 glioblastoma cells were incubated with the virus for 48 h and positive cells were selected by puromycin resistance. Untreated or SELP knockdown (shSELP) GL261 cells ($5\times10^4$ cells) were stereotactically implanted into the striatum of 6-weeks old male C57BL/6 mice. Mice were untreated or treated with the nano-vaccine intranasally (20 µl containing 100 µg of antigens, 20 µg of CpG and 20 µg MPLA: 10 µl in each nostril) once a week for three weeks, starting at day 3 post tumor inoculation. Tumor volume and development were followed by MRI (MR solutions). FIG. 16 illustrates a reduction in tumor volume for SELP knockdown and the vaccinated groups, the effect stronger and synergistic when combining both treatments.

Example 11

In Vivo Intervention Study Using Mannose-Grafted
PLGA/PLA Nano-Vaccine Platform (Co-Entrapping
MART-1 Peptides and TLR Ligands) in B16F10
Melanoma Brain Metastases Mouse Model It was recently found that the MCP-1/CCL2 chemokine is upregulated by activated-astrocytes in melanoma brain metastasis, which in turn triggers the infiltration of tumor-associated macrophages (TAM) during the early stage of melanoma brain metastasis colonization. Inhibition of astrocyte chemokine-secretion together with the administration of an anti-inflammatory small molecule inhibitor of CCL2 (bindarit) impaired the progression of the metastatic disease by significantly reducing astrocyte activation and consequently inhibiting the migration and infiltration of TAMs. This occurred at the early stage of metastatic colonization and not during the advanced progression of the disease. Flow cytometry and histological analyses revealed an enhanced infiltration of adoptive immune cells in the proximity of the tumor in mice treated with bindarit. Hence, it was hypothesized that the combination of an intranasal MART-1 vaccine with the CCL2 secretion-blockage could sensitize both innate and adoptive immune systems to fight against tumor development in the brain.

Therefore, man-PLGA/PLA nano-vaccine was synthesized using TPGS and PL (to increase nano-vaccine mucoadhesiveness), entrapping combinations of MART1 MHC class I or MHC class II peptides and TLR ligands (CpG and poly (I:C)).

Figure 17A:
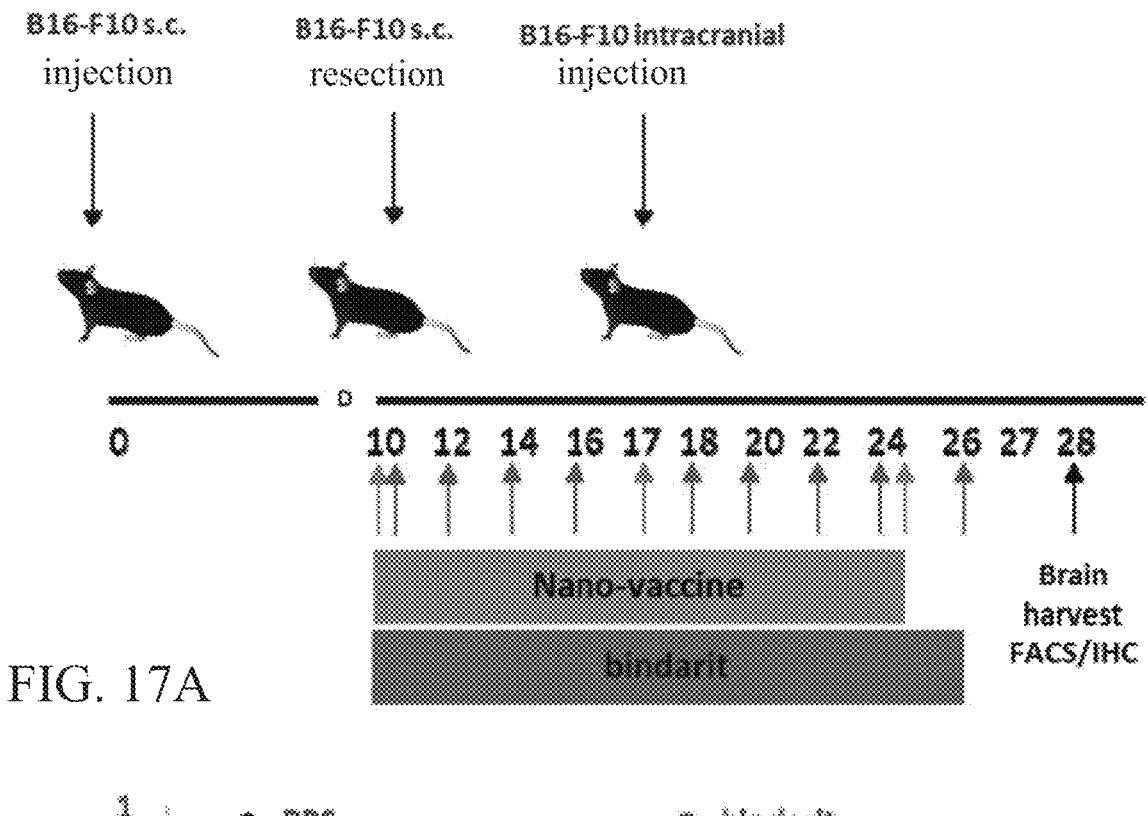
Figure 17B:
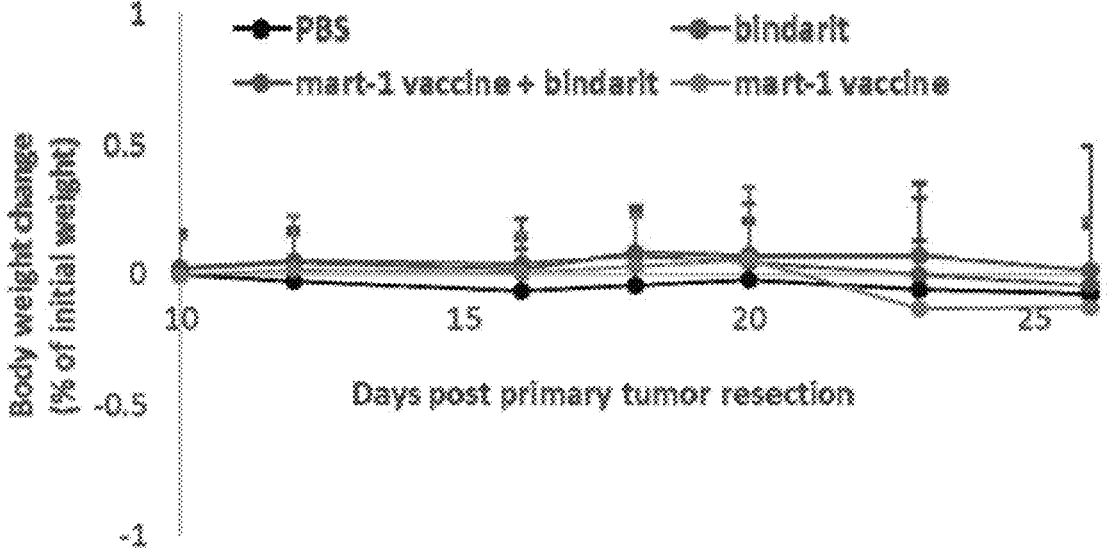
Figure 17C:
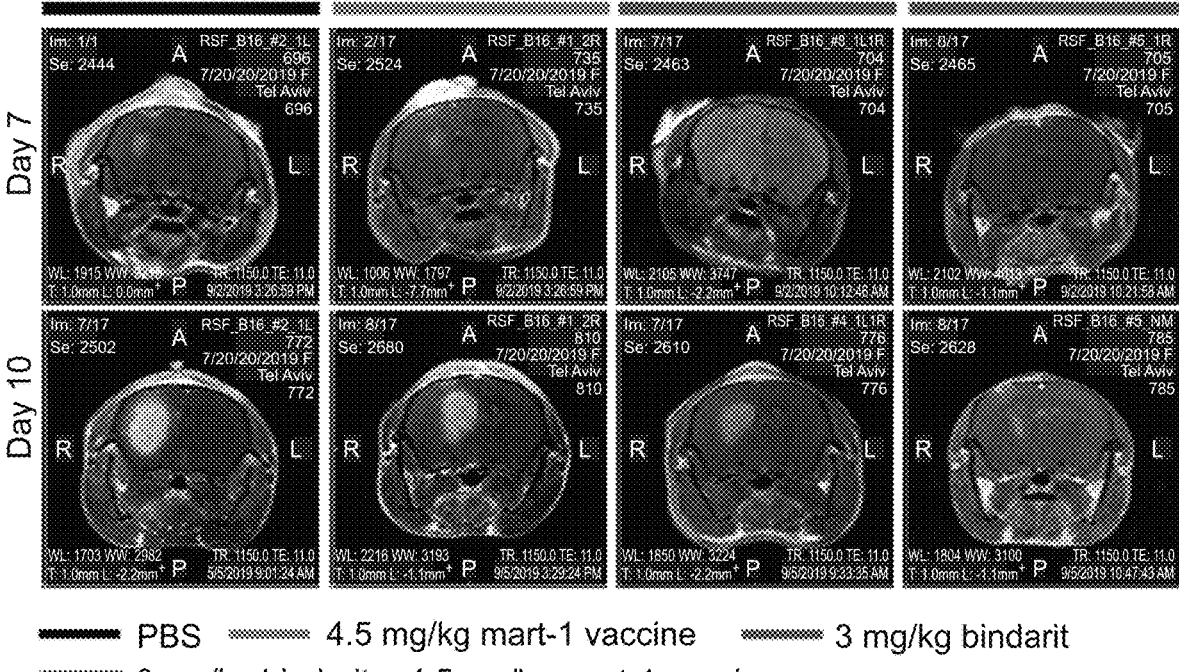
Figure 17D:
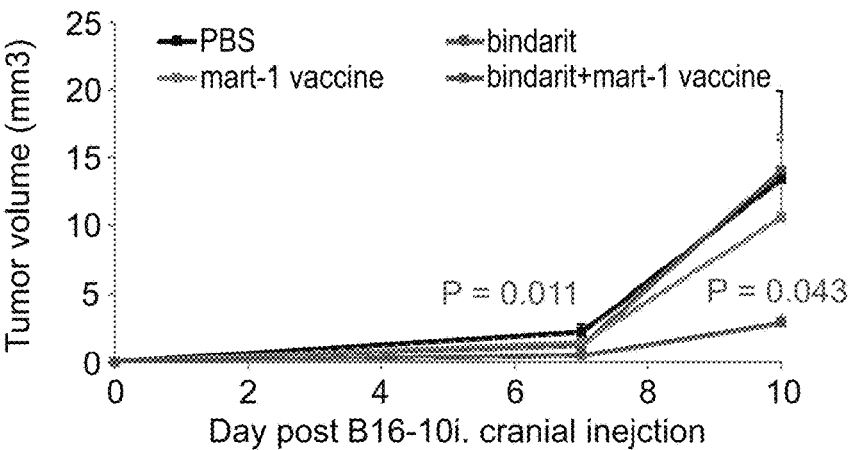

Briefly, B 16F10 melanoma cells were inoculated subcutaneously (100.000 cells), and tumors were resected when the average size 150-200 mm$^3$. Ten days post resection of the primary tumor, mice were randomized and injected i.v. with one dose of bindarit (3 mg/kg free drug) every other day and immunized with the intranasal administration of the nano-vaccine containing MART-1 peptides (4.5 mg/kg) once a week for three weeks. A week following primary tumor resection, B16F10 melanoma cells (15.000 cells) were injected intracranially and mice were continuously treated as previously described (FIG. 17A).

B16F10 brain tumors were monitored by Magnetic Resonance Imaging (MRI) at day 7 and 10 upon intracranially injection. At an advanced stage of tumor progression, the tumor size of the group treated with the combination of nano-vaccine+bindarit was significantly reduced compared to the PBS or the mono-treatment groups (FIGS. 17C-D), showing a synergistic effect of this dual therapy combination.

At day 10, the brains were harvested, fixed and stained for the relevant markers. In addition, cell suspensions were obtained for flow cytometry analysis and for further viability and cell cycle arrest assays. As shown in FIG. 18, the combination of nano-vaccine and Bindarit induced cell cycle arrest at phase G0/1, whilst mono-treatments did not affect tumor cell viability (FIG. 18).

Example 12

In Vivo Intervention Study Using Mannose-Grafted
Nano-Vaccine Platform (Co-Entrapping Gp100
Antigen Peptide and TLR Ligands) in D4M.3A
Melanoma Brain Metastases Mouse Model D4M.3A melanoma cells do not express MART-1 marker, and therefore gp100 peptide was entrapped within man-PLGA/PLA nanoparticles.

The man-PLGA/PLA nano-vaccine was synthesized using TPGS and PL (to increase nano-vaccine mucoadhesiveness), entrapping combinations of gp100:25-33 (MHC class I (EGSRNQDWL; SEQ ID NO: 7)) or gp100:44-59 MHC class II peptides (WNRQLYPEWTEAQRLD; SEQ ID NO: 8) and TLR ligands (CpG and poly (I:C)). An in vivo study was carried out in a second model of melanoma brain metastasis in order to validate the efficacy as monotherapy of intrasal-vaccine against gp100 melanoma peptides.

Briefly, D4M.3A melanoma cells were inoculated subcutaneously (1,000,000 cells) and the tumor was resected when the average size reached between 150-200 mm$^3$. Ten days post resection of the primary tumor, mice were randomized and injected intranasally with nano-vaccine containing gp100 peptides (4.5 mg/kg) once a week for three weeks. A week after primary tumor resection, D4M.3A melanoma cells (50.000 cells) were injected intracranially and mice were treated as illustrated in FIG. 19A.

D4M.3A brain tumors were monitored by MRI at day 8, 11 and 16 upon intracranial injection. Tumor size of the treated group was significantly decreased compared to the PBS group as illustrated in FIG. 19B. Body weight did not change significantly.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority documents of this application are hereby incorporated herein by reference in their entirety.

In addition, any priority documents of this application are hereby incorporated herein by reference in their entirety.

What is claimed is:

1. A polymeric nanoparticle comprising:

(i) at least one disease-associated antigen which is capable of producing a T-cell response, (ii) at least one adjuvant;

(iii) a dendritic cell targeting moiety which is attached to an outer surface of the nanoparticle comprising poly (lactic-co-glycolic acid) (PLGA), said dendritic cell targeting moiety comprising mannose (man), wherein 20% of the polymers of the nanoparticle are mannosylated, wherein said man is bound directly to said PLGA to form man-PLGA;

(iv) a polynucleotide agent; and (v) d-α-tocopheryl polyethylene glycol 1000 succinate (TPGS).

2. The polymeric nanoparticle of claim 1, wherein said polymers comprise poly (vinyl alcohol) (PVA).

3. The polymeric nanoparticle of claim 1, wherein said at least one adjuvant comprises a Toll-like receptor (TLR) ligand.

* * * * *